US006399585B1

(12) United States Patent
Larson et al.

(10) Patent No.: US 6,399,585 B1
(45) Date of Patent: Jun. 4, 2002

(54) IN UTERO TREATMENT OF CFTR-RELATED DEFICIENCIES

(76) Inventors: Janet E. Larson, 2136 Lakeshore Dr.; J. Craig Cohen, 2135 Lakeshore Dr., both of Mandeville, LA (US) 70448; Harmanjatinder S. Sekhon, 615 E. 27th Avenue, Vancouver, B.C. (CA), V5V2K7

( * ) Notice: Subject to any disclaimer, the term of this patent is extended or adjusted under 35 U.S.C. 154(b) by 0 days.

(21) Appl. No.: 09/065,380

(22) Filed: Apr. 23, 1998

Related U.S. Application Data

(63) Continuation-in-part of application No. 08/648,315, filed on May 15, 1996, now abandoned.

(51) Int. Cl.[7] ............... A01N 43/04; A61K 31/70; C12N 15/63; C12N 15/09; C12N 15/00
(52) U.S. Cl. ............ 514/44; 424/93.21; 435/455; 435/456; 435/69.1; 435/320.1; 435/325
(58) Field of Search ............. 514/44; 424/93.21; 435/455, 456, 69.1, 320.1, 325

(56) References Cited

U.S. PATENT DOCUMENTS

| | | |
|---|---|---|
| 5,240,846 A | 8/1993 | Collins et al. |
| 5,384,128 A | 1/1995 | Meezan et al. |
| 5,434,086 A | 7/1995 | Collins et al. |
| 5,585,362 A | 12/1996 | Wilson et al. |
| 5,621,007 A | 4/1997 | Gribkoff et al. |

OTHER PUBLICATIONS

Snouwaert, J. N. et al., Science, vol. 257(5073), pp. 1083–1088, Aug. 21, 1992.*
Sekhon, H.S., and J.E. Larson (1995). "In utero gene transfer in the pulmonary epithelium." Nature Med. 1:1201–1203.
Pier, G.B., M. Grout et al. (1996). "How mutant CFTR may contribute to *Pseudomonas aeruginosa* infection in cystic fibrosis." Am J Respir Crit car Med 154:S175–S182.
Pitt, B.R. et al. (1995). "Retrovirus mediated gene transfer in lungs of living fetal sheep." Gene Therapy 5:344–350.
McCray, P.B., et al. (1995). "Adenoviral–mediated gene transfer to fetal pulmonary epithelia in vitro and in vivo." J. Clin. Invest. 95:2620–2632.
Davies, J.C., et al. (1997). "CFTR gene transfer reduces the binding of *Pseudomonas aeruginas* to cystic fibrosis respiratory epithelium. " Am. J. Respir. Cell Mol. Biol. 16:657–663.
Fung, D.C.K., et al. (1995) (1995). "Mucus glycoconjugate complexes released from feline trachea by a bacterial toxin." Am. J. Respir. Cell Mol. Biol. 12:296–306.
Kolber, R. (1995). "RAC tiptoes into new territory: In utero gene therapy." J. of NIH Res. 7:37–39.
Mastrangeli, et al. (1993). "Diversity of airway epithelial cell targets for in vivo recombinant adenovirus–mediated gene transfer." J. Clin. Invest. 91:225–234.
MacLeod. R.J., et al. (1994). "Developmental differences of cystic fibrosis transmembrane conductance regulator functional expression in isolated rat fetal distal airway epithelial cells." Pediatric Research 35:45–49.
Zhou, L., R.W. Graeff et al. (1996). "Keratinocyte growth factor stimulates CFTR–independent fluid secretion in the fetal lung in vitro." Am. J. Physiol. 271:L987–94.
Larson, J.E., S.L. Morrow et al. (1997). "Reversal of cystic fibrosis phenotype in mice by gene therapy in utero." Lancet 349:619–620.
Zhou, L., C.R. Dey et al. (1994). "Correction of lethal intestinal defect in a mouse model of cystic fibrosis by human CFTR." Science 266:1705–1708.

\* cited by examiner

*Primary Examiner*—Jill D. Martin

(57) ABSTRACT

The present invention relates to lung cells having a novel phenotype, morphology, and immunoprotectant properties. The invention further relates to cell lines derived from such cells and methods for producing such cells, both in vivo and in vitro. The invention additionally relates to expression products of such cells and cell lines. The present invention also relates to the application methods that temporarily ameliorate CFTR deficiency to in utero therapy, with the surprising result that amelioration then extends beyond birth and beyond the duration of the temporary in utero effect to become long-lasting amelioration.

6 Claims, 34 Drawing Sheets

Figure 1A:
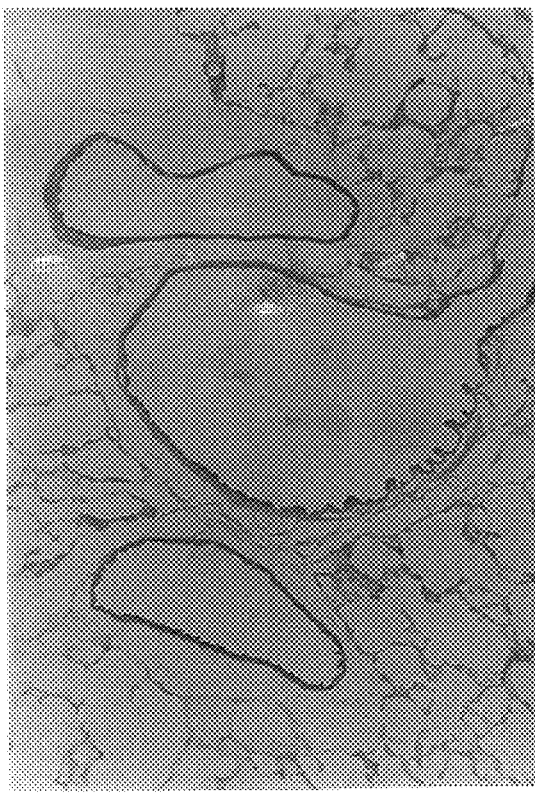

(34 of 34 Drawing Sheet(s) Filed in Color)

IN UTERO TREATMENT OF CFTR-RELATED DEFICIENCIES

CROSS REFERENCE TO RELATED APPLICATIONS

This application is a continuation-in-part of application Ser. No. 08/648,315, filed May 15, 1996, now abandoned.

GOVERNMENT SUPPORT

Certain work in connection with the present invention was developed with government support under U.S. Public Health Service Grant HD00880 and Louisiana Educational Quality Support Fund Grant 007P. Accordingly, the by government may have certain rights in the invention.

BACKGROUND OF THE INVENTION

1. Field of the Invention

The present invention relates to lung cells having a novel phenotype, morphology, and immunoprotectant properties. The invention further relates to cell lines derived from such cells and methods for producing such cells, both in vivo and in vitro. The invention additionally relates to expression products of such cells and cell lines.

2. Background of the Technology

Genetic information in living creatures is contained in deoxyribonucleic acid (DNA) which is the chemical that makes up genes. Formed from long chains of "nucleotide bases", genes are the building blocks of life. The nucleotide bases, guanine (G), cytosine (C), adenine (A), and thymidine (T), bond together into long chains that provide the recipe for what our bodies make. Genes dictate the production of chemicals (proteins) that make our bodies function and create our appearance, such as our sex and our hair, eye, and skin colors. Genes, however, can also be missing, defective, or not fully operational which can lead to serious medical problems. Certain medical problems that are genetic in origin are cystic fibrosis (a severe disease that commonly manifests itself in chronic lung problems), adenosine deaminase deficiency ("ADA deficiency", which results in a nearly nonfunctioning immune system in a patient), α1-antitrypsin deficiency ("AAT deficiency", which results in liver dysfunction and emphysema style malfunction in the lungs), among others.

The recipe, mentioned above, stems from the fact that genes "code" for, and "express", proteins within cells. That is, the cellular machinery within a cell reads the genetic code that is present within the cell and manufactures (expresses) the appropriate protein. The resulting proteins are used in a variety of different processes in the body. Such proteins can be used in "signaling" the cells to do something, used by cells to accomplish a task, or the like. Where a gene is missing or defective, the cells are incapable of properly functioning in signaling, accomplishing their task, or the like. Where a gene is underexpressed, i.e., makes too little protein, there may be insufficient quantities of the protein present in the body to provide proper function or the like. In other cases a gene may be "overexpressed", i.e., too much protein is made, which may lead to undesirable consequences. It is this latter case that is believed to play a role in certain cancers, for example, oncogenes are genes that become overexpressed and appear to play a role in the development of certain cancers.

Gene therapy is a therapeutic approach in which a disease or genetic defect in a patient is treated or corrected through providing a "foreign" gene that is either missing, defective, underexpressed, or will help treat the disease. The potentials of gene therapy are, therefore, enormous. In theory, many diseases can be treated or cured through the use of gene therapy.

There are many gene therapeutic approaches that are currently being studied, either preclinically, in animals, or clinically, in human patients. One of the earliest gene therapeutic approaches that was tried (in mid-1991) was the correction of ADA deficiency. ADA deficiency is an enzymatic deficiency. In ADA deficiency, patients are susceptible to virtually any infection or disease—a cold, for example, can potentially be fatal. Suffers from ADA deficiency are forced to live their usually very short lives in an isolation chamber (i.e., a bubble baby).

In the gene therapeutic approach for treating ADA deficiency, in a process known as "ex-vivo" gene therapy, particular immune cells from patients were taken from their bodies and a foreign ADA gene was inserted into the genetic material of the cells using a "retrovirus" (a virus that inserts itself into the DNA of a cell). Such "transduced" or "transgenic" cells were then capable of producing the protein adenosine deaminase. The transduced cells were reintroduced into the patients. It was recently reported that one of the patients, so treated, appears to be producing about 25% of the normal levels of ADA, while another of the patients appears to be producing only about 1% of the normal levels. Generally, in enzymatic type deficiencies, such as ADA deficiency, if one can restore approximately 10% of normal production of protein, the patient should experience generally normal function. Thus, it appears that success was achieved in one of the two patients. See *New York Times;* p. 422, (Oct. 20, 1995), the disclosure of which is hereby incorporated by reference.

Cystic fibrosis (CF) is a genetic disease that afflicts infants in approximately 1 of every 2000 or 9000 births, depending on race. In CF, patients experience severe "endocrine" misfunction. The endocrine system includes all of the cells and organs involved in the secretion of substances, particularly of hormones, in the body. One of the significant symptoms of CF, and a leading cause of death therefrom, is chronic lung problems, including, a thick mucous that fills the lungs, infections, and persistent coughing. In addition, the lungs of the patient with CF are susceptible to repeated bacterial infections which ultimately lead to lung damage and respiratory failure.

A gene, the CFTR gene, has been used in human clinical trials in an effort to restore lung function in patients suffering from CF. Some success has been achieved, however, as in many therapeutic procedures, where a foreign protein or gene is administered to a patient, the body often recognizes such materials as foreign and mounts an attack on the foreign materials, called an immune response.

An immune response is visible in situations where a cut becomes infected with bacteria, the cut swells, becomes red and inflamed, becomes warm, may have pus or the like. In this process, the body has recognized the presence of foreign bacteria and has mounted an attack on it. Further, the body has a system for remembering the foreign bacteria ("memory cells") so that, in the future, if exposed to the bacteria again, it can mount its attack more quickly.

The immune system, and the response that the immune system mounts, is very useful in protecting our bodies against infection and many diseases. However, the very system that assists us in staying healthy, is often an obstacle to the delivery of genes to a patient. When genes are attacked by the body's immune system, the function of the gene (the gene's ability to produce the desired protein) is often destroyed.

It has been proposed that prenatal fetuses (in utero, prior to birth) may not possess as significant an immune response to foreign genes. It is thought that mammals, at such a stage of development are "immunotolerant." Immunotolerant essentially means that the immune systems of such animals will not so readily attack foreign genes. This belief is founded on the principal that prenatal fetuses are exposed to multiple foreign genes from the "mother" in addition to the fact that the immune system in the infant is still developing.

In addition to their potential immunotolerance, prenatal fetuses offer yet another advantage over more mature mammals. This advantage is that, in theory, certain genetic defects that compromise the health of the infant upon birth can be treated prior to delivery. CF is an example; chronic lung infections can result in irreversible lung damage. Through providing the CF gene to an infant prior to their delivery from the uterus, the lung problems could potentially be avoided.

Thus, was suggested that prenatal infant mammals would be a good target for gene therapy. Indeed, based on this postulate, several groups have tried to deliver foreign genes to prenatal animals. Such groups injected foreign genes into the amniotic fluid surrounding a prenatal infant mammal. It was expected that the gene would be breathed in and swallowed by the infant as it begins "practicing" using such muscles. The groups initially observed positive results; the injected gene was expressed in certain tissues in the infant mammal. In contrast to the predictions related to the immunotolerance of the prenatal infants, however, each of the groups who have tried to deliver foreign genes to such infants, in utero, have observed a significant immune response to the foreign genes that were delivered. The immune response was such that the activity of the foreign gene was destroyed within a relatively short time after delivery. See McCray et al. "Adenoviral-mediated gene transfer to fetal pulmonary epitheliain vitro and in vivo" *J. Clin. Invest.* 95:2620–2632 (1995); Kolberg "RAC tiptoes into new territory: in utero gene therapy" *J. NIH Res.* 7:37–39 (1995), the disclosures of which are hereby incorporated by reference.

In co-pending U.S. patent application Ser. Nos. 08/550, 918 and 60/008,161 each filed on Oct. 30, 1995, we described the successful rat in utero delivery and long-term expression of two genes: the lac Z reporter gene (Lac Z) and the cystic fibrosis transmembrane conductance regulator gene (CFTR). We delivered the gene at a time when the lungs were developing and the budding bronchioles were lined with pleuripotential stem cells. Each of the genes were taken up by the cells and expressed for extended periods of time (i.e., for as long as we monitored the animals). No evidence of immune response was noted. In the case of the CFTR gene, moreover, we observed a phenotypic and morphological alteration of the cells. The altered cells appeared to secrete or excrete certain glycoconjugates and lipids.

In earlier work, Whitsett et al. (*Nature Genetics* 2:13–20 (1992)) prepared transgenic mice designed to over-express CFTR protein products. Mice were transduced with hCFTR gene under the control of a 5' transcriptional element of the human surfactant protein C gene, which contains lung specific promoter-enhancer elements. While Whitsett and colleagues observed expression of the CFTR gene in the mice, review of the photomicrographs and figures in the paper do not indicate phenotypic or morphological alterations to the lung cells of the animals. Secretion or excretion of mucous like glycoconjugates in response to in vivo incubation of lung tissues with dirhamnolipid (a toxin from *Pseudomonas aeruginosa*) has been described by Fung et al. *Am. J. Resp. Cell Mol. Biol.* 12:296–305 (1995).

In view of the phenotypic and morphological alterations and apparent excretory or secretory function that we observed in CFTR expressing rodent lungs, in contrast to the work described above, we expected that the cells might possess new function and lead to a better understanding of CF disease and lung immunology in general. For, in addition to the desirability of providing a method to conduct gene transfer in a prenatal infant to correct genetic defects in the infant prior to birth, it would be desirable to understand the function of genes in early fetal cellular development and differentiation. Moreover, owing to some of the potential constraints imposed in utero gene delivery and transfer, it would be desirable to develop therapeutics based upon such elucidation which can be administered to, and operative within, infant and adult patients alike.

BACKGROUND OF THE INVENTION

Cystic Fibrosis

Cystic fibrosis is manifested in a variety of ways, depending largely upon the particular variant gene present in an individual. The disease is described extensively in *Cystic Fibrosis: Current Topics* by J. A. Dodge (Contributor), D. J. H. Brock (Editor), J. H. Widdicombe (Editor) John Wiley & Sons 1996. Recent reviews include Rosenstein and Zeitlin (1998). Manifestations relate to the disruption of exocrine function of the pancreas but also to intestinal glands (meconium ileus), biliary tree (biliary cirrhosis), bronchial glands (chronic bronchopulnonary infection with emphysema), and sweat glands (high sweat electrolyte with depletion in a hot environment).

(Stern 1997) has roughly correlated the amount of functional CFTR produced and the phenotype. Pancreatic exocrine deficiency is at one extreme, with less that 1% of normal CFTR function, followed by progressive pulmonary infection (<4.5%); demonstrable sweat abnormality (<5%); congenital absence of vas deferens; no known abnormality (>10%).

The severity of pancreatic deficiency is also correlated with susceptibility to infection (Tummler, Bosshammer et al. 1997).

Target Organs

The severity of disease varies in different organs. CF disease severity in different organs and species may relate to the expression of an "alternative" plasma membrane Cl-conductance. For example, an alternative conductance has been detected in epithelia of organs from CF mice that exhibit a mild disease phenotype (airway, pancreas) but not in epithelia with a severe phenotype (small, large intestine). (Clarke, Grubb et al. 1994)

Many individuals with congenital bilateral absence of the vas deferens (CBAVD) have CF mutations on one or both CFTR genes. They usually have no respiratory or pancreatic abnormalities, and the sweat chloride is highly variable (Teng, Jorissen et al. 1997; Cuppens, Lin et al. 1998).

CFTR During Development

Gaillard and others studied the distribution of CFTR in normal fetuses ranging from 7 to 39 wk of gestation. CFTR gene expression begins very early in lung development and, with differentiation of the airways, becomes confined to differentiated bronchiolar epithelium. (McGrath, Basu et al. 1993); (Tizzano, O'Brodovich et al. 1994); (Gaillard, Ruocco et al. 1994); (McCray, Reenstra et al. 1992; McCray, Wohlford-Lenane et al. 1992)). By seven weeks, the protein is already present in the yolk sack and in the respiratory epithelium. By the first and second trimester, CFTR mRNA is expressed throughout the human lung epithelium (McCray, Reenstra et al. 1992; McCray, Wohlford-Lenane et al. 1992). Hence, these epithelia have the capability to perform important transport functions before they are fully differentiated.

CFTR is distributed in the developing airways along the cephalocaudal pattern of maturation and differentiation of epithelial cells (Gaillard, Ruocco et al. 1994; McGrath et al, 1993; Gaillard, Ruocco et al. 1994).

Lung Development

An interspecies comparison of the development of lung structure is provided in "Development of Lung Structure" by I. Y. R. Adamson in The Lung: Scientific Foundations, ed. by R. G. Crystal, J. B. West et al., Raven Press, Ltd. 1991

A classification of stages in lung development is based on Boyden, E. A. "Development of the Human Lung" in *Brennermatn's Practice of Pediatrics*, Vol. 4. Hagerstown, Md.: Harper & Row, 1972. Chap. 64.)

Pseudoglandular period (5 to 17 weeks.

Cut sections of lung apear as acinous glands, with elaborate branching of the airway and pulmonary vasculature.

Canalicular period (13 to 25 weeks).

The bronchi and bronchiolar lumnina enlarge. Each terminal bronchiole enlongates and divides into two respiratory bronchioles.

Terminal sac period (24 weeks to birth).

New respiratory bronchioles continue to appear and two types of pneumocytes, the epithelial lining cell, can be recognized. Surfactant is begins to be produced. Extrauterine survival becomes possible as the pulmonary and vasculature develops and the epithelial lining thins.

Alveolar period (late fetal to 8 years)

Alveoli increase 6 to 8 fold to reach adult numbers by 8 years.

The Gene

CFTR expression is regulated by multiple transcriptional and translational mechanisms. Several alternatively spliced isoforms have been identified of which at least some are functional and organ specific.

Therapy

Selected compounds that activate CPTR channels are listed in Table 2

TABLE 2

Selected compounds that activate CFTR channels

| CFTR ACTIVATORS | COMMENTS | REFERENCES |
| --- | --- | --- |
| heat-stable enterotoxin and guanylin | Guanylin is an endogenous intestinal peptide. | (Chao, de Sauvage et al. 1994) |
| genistein and tyrphostin 47 | Acts through tyrosine kinase inhibition. | (Sears, Firoozmand et al. 1995) |
| anthracene-9-carboxylic acid | Favors outward Cl— current. | (Zhou, Takai et al. 1997) |
| phenylimidazothiazoles, bromotetramiole etc. | Phosphatase inhibitors | (Becq, Verrier et al. 1996); |
| pyrophosphate | Binds to NBD domains. | (Carson, Winter et al. 1995) |
| fluoride | Slows channel closure. | [Berger et al. 1998 |
| xanthines, particularly 1,3, or 7 alkyl substituted derivatives. | Unlike other CFTR activators, xanthine activation is not coupled to cyclic AMP levels. | (Chappe, Mettey, et al. 1998) |

The Protein

CFTR is a member of a ubiquitous superfamily of related ATP-binding proteins, known as ABC transporters or "traffic ATPases" (Bianchet, Ko, et al. 1997). Most members are involved in active transport of small hydrophilic molecules across the cytoplasmic membrane. All these proteins share a conserved domain of some two hundred amino acid residues, which includes an ATP-binding site. They are found in both prokaryotes and eukaryotes. Members of the ABC transporter superfamily are mutated to cause diseases that include hyperinsulinemia, adrenoleukodystrophy, Stargardt disease and multidrug resistance, as well as cystic fibrosis.

The CITR channel consists of two motifs, each containing a membrane-spanning domain (MSD) and a nucleotide-binding domain (NBD), linked by a regulator domain. One MSD-NBD motif is sufficient to form a Cl- channel Ostedgaard, Rich et al. 1997). A model graphically describing a likely relationship for all of these domains is presented by Ackerman and Clapham (1997). In this model, 12 transmembrane segments span the membrane forming a pore, while the NBD1 and NBD2 domains are tethered to the pore on the intracellular side. The R, or gating domain, is tethered to the pore and to NBD1, forming a "ball and chain" structure that functions as a phorphorylation-regulated stop valve (Ma, Tasch et al. 1996). For the Cl- channels to open, they must be phosphorylated and then exposed to a hydrolyzable nucleoside triphosphate, such as ATP (Lohmann, Vaandrager et al. 1997). Cellular phosphatases rapidly dephosphorylate the channels, inactivating them (Gadsby D C, Nairn A C. Trends Biochem Sci Nov. 19, 1994;(11):513–518).

Protein kinase A (PKA) is necessary for phosphorylation of CFTR (McDonald, Matthews et al. 1995); nevertheless, PKA alone is not sufficient to open the CFTR chloride channel in the presence of MgATP. Additional phosphorylation by protein kinase C (PKC) is required for acute activation of CFTR by PKA (Jia, et al. 1997).

Physiological Activity

CFTR is well known as a non-rectfying chloride channel, regulated by ATP and phosphate, and this function often eclipses perception of the protein's collateral abilities (Jiang and Engelhardt, 1998). Nevertheless, CFTR comprises a complex structural and regulatory system. In these collateral roles, CFTR protein may also transport ATP (Sugita, Yue et al. 1998; Cantiello, Jackson et al, 1998); regulate outwardly rectifying chloride channels (ORCC) and epithelial sodium chloride channels (ENaC) (Ismailov, Awayda et al. 1996; Stutts, Rossier et al. 1997; Briel et al 1998); mediate vesicular trafficking (Bradbury, Cohn et al. 1994); mediate secretion of the endogenous cAMP-linked hormones VIP and secretin (Peters, van Doorninck et al 1997); associate with potassium channels (Ho, 1998); interact with the actin cytoskeleton (Cantiello, 1996); bind a *Pseudomonas aeruginosa* lipopolysaccharide-core oligosaccharide ligand for epithelial cell ingestion (Pier, Grout et al. 1996) and affect glycosylation. The constitutive pathway for secretion of glycoconjugates and proteins from microvesicles is intact in CF, but regulated secretion from secretory granules is defective. CF exocrine epithelia do not respond to cholinergic or adrenergic stimulation (Mills, Dorin et al. 1995; Pereira, Dormer et al. 1995).

CFTR also shows permeability to large organic anions, but only from the intracellular side of the membrane. ATP hydrolysis is required to maintain asymmetric permeability. Loss of this assymetric permeability to large organic anions may contribute to the pleiotropic symptoms seen in cystic fibrosis (Linsdell and Hanrahan 1998).

Ion Channels

The level of hydration at the surface of many tissues, particularly the lung, is partially determined by CFTR, and partially by complimentary ion channels, notably the epithelial sodium channel (ENaC) of the apical membrane. To appreciate the complex interactions that occur, it is necessary to consider the aggregate effect of all types of ion channels. About 30% of cellular energy expenditure is stored in a cellular cross-membrane sodium/potassium ion gradient. Ion channels are transmembrane protein tunnels that act as switches to relieve the ion gradient and thus release the stored energy. They are more efficient than enzymes, and they allow the flow of up to 10 million ions/second/channel. A few thousand of each type of channel/per cell is general sufficient. They are usually classified as sodium, potassium, calcium, or chloride channels. Conductance is a measure of ion flow and it is expressed as the charge/second/volt. The passive flow of ions through channels is influenced by both a chemical and an electrical gradient. The two forces are balanced at the Nernst potential. The transmembrane potential of a cell is a weighted average of the Nernst potential of each open ion channel. Current passing through an ion channel is measured with a patch-clamp technique. In this technique, an electrode pressed against the cell membrane forms a sealed 1 to 3 um2 area of membrane within which all flowing ions are captured. The subject of ion channels is reviewed by Ackerman and Clapham (1997).

Membrane Hydration

One result of the interaction of ion channels is the capability of normal airway epithelia to either absorb salt and water (driven by active Na transport) or secrete liquid (driven by active Cl transport). Active transport of Na drives liquid absorption in two steps: (1) Na enters the cell through the ENaCs; and (2) Na is pumped from the cell by the Na/K/ATPase on the basolateral membrane. CFTR at least partially determines the normal secretion/absorption balance by at least three of its functions: conduction of Cl- ions, inhibition of ENaC. and stimulation of alternative Cl- channels such as outwardly rectifing chloride channels (ORCCs). Thus, CFIR mutations that both drastically affect its ability to move Cl- effectively itself and also eliminate its ability to regulate other channels cause the most severe disease. The channeling and regulation functions of CFTR are not necessarily tightly coupled; one can be eliminated while the other is preserved. (Schwiebert, Morales et al. 1998).

It is possible to supplant each of the CFTR functions that determine membrane hydration with CFTR-sparing drugs. Drugs that inhibit complementary ion channels, particularly ENaC, can be use to supplant the regulatory function of CFTR over ENaC. Amiloride and triamterene bind to ENaC and block conduction (Barbry, Champigny, et al. 1996). Epithelial Na+ channel activity is tightly controlled by several distinct hormonal systems, including corticosteroids and vasopressin. For example, synthesis of ENaC is positively regulated by aldosterone, and the aldosterone antagonist spironolactone can be used to reduce the number of ENaC channels (Haris and Rado 1996). CFTR regulation of alternative ion channels, such as ORCCs, can be supplanted with purinergic receptor agonists, for example UTP (Knowles, M. R., Olivier, K. N., et al 1995). This is because CFTR regulates ORCCs by facilitating the release of ATP out of cells (Sugita, Yue et al. 1998). Once released from cells, ATP stimulates ORCCs by means of a purinergic receptor P2Y2 (Fulmer, Schwiebert et al. 1995). Finally, CFTR Cl- channel function in mutant CFTR channels can be recovered by several means (see ## MISSING MARKER: "table mutant mechanisms" ##).

Alternative Cl- Channel Activators

Activators of alternative Cl- channels that could spare CFTR function extend beyond ATP and UTP: Ca(2)-ATPase inhibitor 2,5-di-(tert-butyl)-1,4-hydroquinone(Chao, Kouyama et al. 1995); 1-ethyl-2-benzimidazolone (1-EBIO) (Devor, Singh et al. 1996); psoralen (Devor, Singh, et al 1997); UDP (Lazarowski, Paradiso, et al 1997); UDP binds to a receptor distinct from P2Y2 (Lazarowski, Paradiso, et al 1997).

Schwiebert, Cid-Soto et al. (1998) have explored the possibility of manipulating ClC-2 chloride channels by pharmacotherapy to relieve the symptoms of CF.

Aerosolized uridine triphosphate (UTP) induces Cl- (and liquid) secretion in CF airway epithelia via non-CFTR Cl- channels. Short-term aerosolized UTP is well tolerated by normal subjects and patients with CF, and pilot studies in normal subjects show that aerosolized UTP is an effective stimulator of mucociliary clearance (Knowles, M. R., Olivier, K. N., et al 1995).

Purinergic Receptors

Purinergic receptors have a significant role in the present invention, and a brief description of these receptors follows. Nomenclature, agonists, and tissue distribution of purinergic receptors are reviewed by Heilbronn, Knoblauch et al (1997). An extended description is also provided in P2 purinoceptors; localization, function and transduction mechanisms, Ciba Foundation Symposium 198. Ed. by D. J. Chadwick and J. A. Goode, pub. John Wiley & Sons (1996). Parr et al (1994) describe the use of the human purinergic (P2U) receptor to bypass the CFTR Cl- secretory pathway. ATP and UTP bind to the receptor, and in airway epithelia, the cellular response is to activate an alternative, non-CFTR-dependent Cl- conductance. Another response to purinergic reception is the secretion of mucus by goblet cells. Other tissues with known P2U receptor function include hepatic biliary cells and thyroid tissue (Heillbronn and Knoblauch, 1997). P2Y2 receptors, UTP-P2Y4 receptors and unidentified ATP-specific receptors are said to be present in human tracheal gland cells (Merten, Saleh et al. 1998). The P2U receptor is described in U.S. Pat. No. 691,156 issued to Boucher et al. Nov. 25, 1997. Purinergic receptor agonists have been disclosed in U.S. Pat. No. 5,641,500 issued Jun. 24, 1997 to Trepel et al., with assertions of improved therapeutic features such as increased resistance to hydrolysis. Examples of these compounds include, but are not limited to, ADP, AMP, AMP-PNP, $\alpha,\gamma$ methylene ATP, and ATP$\gamma$S.

Currently, clinical tests on the use of UTP to treat CF symptoms are being conducted. Thus far, ATP has been avoided to avoid the bronchoconstrictor effects of its adenosine moiety. Clinical trials on the use of amiloride and UTP together are also being conducted (Boucher 1994).

Besides the direct effect of purinergic receptors on alternative ion channels, they have other physiological effects that are relevant to the present invention. For example, extracellular ATP promotes cellular proliferation in renal inner medullary collecting duct cells and this occurs through purinergic receptors (Ishikawa, Higashiyama et al. 1997).

Actin filaments directly interact with CFTR and regulate its channel activity (Cantiello 1996; Ismailov, Berdiev et al. 1997; Brezillon, Zahm et al. 1997).

Recently, Wersto et al described the use of a fluorescent dye, dihydrorhodamine 6G (dR6G), to stain cells expressing functional CFTR Cl- permeability. Transfer of the CFTR gene into CFTR- cells increased staining by the dye. The staining pattern tracks expected physiological activity. cAMP stimulates dR6G staining and cAMP antagonists inhibit staining. Staining is ATP- dependent and inhibited by Cl- removal or the addition of 10 mM SCN-. dR6G fluorescence distinguishes amended cells after gene therapy (Wersto, Rosenthal et al. 1996).

Mutants

Selected mutants are discussed below to provide a sense of the spectrum of phenotypes that can result from various mutations in the CFTR gene.

Five mechanisms by which mutations disrupt cystic fibrosis transmembrane conductance regulator function have been suggested by (Kerem and Kerem 1995). They are listed in Table 3, along with possible corrective treatments for each mechanism.

1995; Clarke, Grubb et al. 1994; Colledge, Abella et al 1995). The CFTR homozygote shows defects in the airway and intestinal epithelia similar to those in the corresponding

TABLE 3

FUNCTIONAL MECHANISMS OF CFTR DEFICIENCIES

| DEFECTIVE MECHANISM | EXAMPLES | REFERENCES | POSSIBLE THERAPIES |
|---|---|---|---|
| production | W1282X, R553X, R1162X, G542X | | aminoglycosides |
| processing | ΔF508 | Guay-Broder, C., Jacobson, K. A., et al.1995; Arispe, Ma et al 1998; Rubenstein, Egan et al. 1997; Rubenstein and Zeitlin 1998; Brown, Hong-Brown et al. 1996; Sato, S., Ward, C. L., et al. 1996; U.S. Pat. No. 5674898 | 8-cyclophenyl-1,3-dipropylxanthine; 1,3-diallyl-8-cyclohexylxanthine phenylbutyrate; butyrate; chemical chaperones: glycerol, TMANO |
| regulation | mutations at multiple phosphory-lation sites in membrane domains, first NBD | Becq, Verrier et al. 1996 | phenylimidazothiazoles genistein, milrinone |
| conduction | R117H | Carson, Winter et al. 1995; U.S. Pat. No. 5686114 | inorganic pyrophosphates including etidronate (also stimulates G551S and ΔF508) |
| reduced synthesis | A455E | U.S. Pat. No. 5366977 | 8-cyclopentyl-1,3-dipropylxanthine, xanthine amino congener |

A biochemical arrest in processing the ΔF508-CFTR mutant protein, the predominant mutation within the human population, prevents CFTR from exiting the endoplasmic reticulum (ER) where it is synthesized (Zhang, Kartner et al. 1998). Although ER-retention mechanisms recognize conformational changes in the mutant protein, they do not necessarily affect other CFTR properties. Both ΔF508-CFrR as well as CFTR function as cAMP-regulated chloride channels in native endoplasrnic reticulum membrane (Pasyk and Foskett 1995). Moreover, retention within the ER of ΔF508 is conditional. A CFTR-like Cl- conductance appears after incubation of CF-affected airway epithelial cells at 25–27° C. (Egan, Schwiebert et al. 1995). Also, treatment with "chemical chaperones" results in the appearance of a fully glycosylated and mature form of the ΔF508 CFTR protein at the plasma membrane (Brown, Hong-Brown et al. 1996; Welch and Brown 1996; Sato, S., Ward, C. L., et al1996). Other suggestions for rescue of ΔF508 CFTR protein include phenylbutyrate (Rubenstein, Egan et al. 1997; Rubenstein and Zeitlin 1998). Intragenic suppressor mutations in NBD1 (for example R553 and R555K) allow ΔF508 to escape from the ER and function as Cl- channels on the cell surface (Teem, Carson et al 1996).

Mutations in CFTR can be associated with elevated sweat chloride concentrations in the absence of the CF phenotype. A 6.8 kb deletion (D14a) and a nonsense mutation (S1455X) in the CFTR genes of a mother and her youngest daughter are associated with isolated elevated sweat chloride concentrations. Detailed clinical evaluation of both individuals found no evidence of pulmonary or pancreatic disease characteristic of CF. mutations in CFTR can be associated with elevated sweat chloride concentrations in the absence of the CF phenotype (Mickle, Macek Jr et al. 1998).

Animal Models

Lansdell, Delaney et al (1998) have conducted a detailed comparison of the mouse and the human CFTR. They conclude that although human and murine CFTR have many properties in common, some important differences in function are observed. These known differences could be considered in analyzing any results obtained from an animal model of cystic fibrosis. Several groups have constructed transgenic mouse models of CF, including a model of the predominant human mutation Δ508 (Dickinson, Dorin et al.

human tissues. Most of the mutant mice demonstrate meconium ileus pathology. Three models exhibit a very high level of fatal intestinal obstruction. (Zhou, Dey et al. 1994) injected the human CFTR gene into cftr- mouse fertilized oocytes. The mice survived and showed functional correction of ileal goblet cell and crypt cell hyperplasia and cAMP-stimulated chloride secretion.

Delaney et al, created mice (Delaney, Alton et al. 1996) carrying the missense mutation G551D and they reflect the human genotype/phenotype of the mutation. They produce normal CFTR at low levels, do not die soon after birth, and are fertile. These mice were used to study the development of lung disease. Unlike humans, they do not show any gross lung pathology, probably because of inter-species differences in ion channel distribution.

Unlike humans, male CF mice are usually fertile. This has been attributed to the presence in mice of an alternative ion channel (Leung, Wong et al. 1996).

Large animal CF models have also been developed, including a primate model. The nucleotide sequence of the coding region of rhesus CFTR is 98.3% identical to human CFTR and the amino acid sequence is 98.2% identical and 99.7% similar. Flanking introns are about 91.1% identical to human introns (Wine, Glavac et al. 1998).

Infection

Most of the morbidity and mortality caused by CF is due to chronic infection of the airways. Bacteria commonly isolated from CF sputum include *Staphylococcus aureus, Haemophilus influenzae, Pseudomonas aeruginosa* (FitzSimmons 1994) . Other pathogens such as *Burkholderia (Pseudomonas) cepacia, Stenotrophomonas (Xanthomonas) maltophilia, B. gladioli, Aspergillus fumigatus,* and nontuberculous mycobacteria are also problematic in some patients.

Genetic Therapy

Twenty clinical trials of gene therapy for cystic fibrosis have been initiated using viral and non-viral vectors for gene transfer (Marcel and Grausz 1997). Vectors that have been studied in attempts to develop gene therapy for CF include adenoviruses, adeno-associated viruses (AAV), and liposomes (MacVinish, Goddard et al 1997).

Yeast artificial chromosomes represent a promising technology for transferring large amounts of DNA (Ripoll, Cowper et al 1998).

Knowles, M. R., Paradiso, A. M. et al (1995) have proposed a method to measure the biological efficacy of gene transfer of the normal CFTR cDNA into CF respiratory epithelia.

Recently adenoviral gene transfer vectors devoid of all viral coding sequences was used to obtain regulated gene expression with decreased toxicity using genomic DNA for gene transfer (Schiedner, Morral et al. 1998).

Synthetic non-viral vectors have large DNA capacities, and they are relatively non-toxic and non-immunogenic. Recent publications on the design and application of non-viral vectors include (Boasquevisque, Mora et al. 1998); (Byk, Dubertret et al. 1998; Escriou, Ciolina et al. 1998); (Murphy, Uno et al. 1998). An aerosolized vector suitable for use with CF patients is of particular interest (Eastman 1998).

Viral systems being developed for use as vectors for ex vivo and in vivo gene transfer include retroviruses, adenoviruses, herpes-simplex viruses and adeno-associated viruses. (Robbins, Tahara et al. 1998; *Gene Therapy Protocols* (*Methods in Molecular Medicine*) by Paul D. Robbins (Editor) Humana Press, 1997).

DOTAP cationic liposome mediated CFTR gene transfer to the nasal epithelium of patients with cystic fibrosis has been shown to be safe and efficacious (Porteous, Dorin et al. 1997).

(Knowles, Noone et al. 1998) have announced a study to evaluate the safety and efficacy of a lipid-DNA complex for producing CFTR gene transfer and correcting the chloride ion transport defect in the nasal epithelium of patients with cystic fibrosis.

Davies has succeeded in correcting the abnormal binding of *P. aeruginosa* to CF respiratory epithelial cells by transfection with CFTR/liposome complexes (Davies, Stern et al. 1997).

Johnson et al. have assessed the variables affecting the efficiency and efficacy of adenovirus-mediated gene transfer to cystic fibrosis airway epithelia (Johnson, Pickles et al. 1996)

In vivo transfer of purified CFTR protein via phospholipid liposomes into the apical membrane of nasal epithelia of CFTR knockout mice has been demonstrated (Ramjeesingh, Huan, et al. 1998).

SUMMARY OF THE INVENTION

As discussed above, in accordance with the present invention, we have demonstrated, where others have failed, that it is possible to conduct gene transfer in a prenatal infant to correct genetic defects in the infant prior to birth. This objective is achieved through the direct delivery of a foreign gene into the amniotic fluid surrounding a prenatal infant mammal inutero. Depending upon the developmental age of the infant when the delivery of the gene is accomplished is essentially determinative of the tissue or tissues in which the gene will be taken up in the cells and expressed therein. In particular, however, we have demonstrated the invention's extreme benefit in connection with the delivery of foreign genes to the lungs of prenatal infant mammals.

Moreover, the present invention allows, through careful selection from amongst several factors, delivery of genes to cells in prenatal infant mammals in a manner that maximizes expression of the gene and minimizes the potential for an immune response in the infant mammal against the foreign gene. Through this work, we have identified a novel lung cell that has altered phenotype and morphology form other lung cells. Further, such cells excrete or secrete glycoconjugates and/or lipids (and particularly, neutral lipids) that appear to protect or "immunoprotect" the cells, and the lung in general, from opportunistic infections, such as bacterial infections. "Glycoconjugates" as used herein refer to agents which include glycoproteins and glycolipids, as well as potentially other glcosylated agents. Thus, the excretory or secretory products of the cells appear directly involved in immunoprotection of cells and are referred to herein as "immunoprotectant factors". As will be appreciated, the mode operation of the "immuno-protectant factors" could be through bacteriostatic, bacterialcidal, immune stimulatory, antireplicatory, or through other modes or processes. Generally, the term "immunoprotectant factors" is used to described any mode in which cells or tissues are protected from opportunistic infections.

Such immunoprotectant factors may be absent in patients suffering from cystic fibrosis disease (CF) and would assist in explaining the susceptibility of CF patients to chronic lung infections. Further, as will be discussed in greater detail below, such immunoprotectant factors are expected to be useful for the treatment of far more than the chronic lung infections in CF. Further, the factors are expected to find application in mitigating a variety of bacterial, viral, and other infections.

The present invention encompasses the following specific subject matter:

In accordance with a first aspect of the present invention, there is provided a cell population derived from a population of pleuripotential stem cells in a portion of a mammal's developing respiratory epithelium, pleuripotential stem cells having been transfected with a viral vector comprising the hCFTR gene and undergone expression of the gene prior to differentiation.

In a preferred embodiment, the viral vector is an adenoviral vector. In another preferred embodiment, the transfection of the pleuripotential stem cells is accomplished in vivo. In another preferred embodiment, the transfection of the pleuripotential stem cells is accomplished in vitro. In another preferred embodiment, the cell population secretes glycoconjugates and lipids that are immunoprotectant to the cell population and mitigate bacterial infection, such as infection with *Pseudomonas aeruginosa*.

In accordance with a second aspect of the present invention, there is provided a cell population derived from a population of pleuripotential stem cells in a mammal's developing epithelium, the pleuripotential stem cells having been transfected with a viral vector comprising the hCFTR gene and undergone expression of the gene prior to differentiation.

In a preferred embodiment the viral vector is an adenoviral vector. In another preferred embodiment, the transfection of the pleuripotential stem cells is accomplished in vivo. In another preferred embodiment, the transfection of the pleuripotential stem cells is accomplished in vitro. In another preferred embodiment, the cell population secretes glycoconjugates and lipids that are immunoprotectant to the cell population and mitigate bacterial infection, such as infection with *Pseudomonas aeruginosa*. In another preferred embodiment, the developing epithelium comprises respiratory tissues. In another preferred embodiment, the developing epithelium comprises the gut.

In accordance with a third aspect of the present invention, there is provided a method of generating cell populations secreting immunoprotectant factors in a prenatal infant, the infant being surrounded by amniotic fluid in utero. In the method, a gene construct comprising an hCFTR gene is delivered into the amniotic fluid at a time when the infant possesses a population of pleuripotential stem cells in the infant's developing epithelium the gene construct being delivered in a manner designed to transfect the pleuripotential stem cells with the hCFTR gene, wherein, upon differentiation, at least a portion of the pleuripotential stem cells form cell populations secreting immunoprotectant factors.

In a preferred embodiment, the gene construct comprises a viral vector. In another preferred embodiment, the viral vector is an adenoviral vector.

In accordance with a fourth aspect of the present invention, there is provided an isolated sample of glycoconjugates and lipids secreted by a cell population derived from a population of pleuripotential stem cells in a mammal's developing epithelium, the pleuripotential stem cells having been transfected with a viral vector comprising the hCFTR gene and undergone expression of the gene prior to differentiation.

In a preferred embodiment, the viral vector is an adenoviral vector. In another preferred embodiment, the transfection of the pleuripotential stem cells is accomplished in vivo. In another preferred embodiment, the transfection of the pleuripotential stem cells is accomplished in vitro. In another preferred embodiment, the cell population secretes glycoconjugates and lipids that are immunoprotectant to the cell population and mitigate bacterial infection, such as infection with *Pseudomonas aeruginosa*. In another preferred embodiment, the developing epithelium comprises respiratory tissues. In another preferred embodiment, the developing epithelium comprises the gut.

In accordance with a fifth aspect of the present invention, there is provided a method of generating a secretory cell population, the secretory cell population being capable of secreting factors that immunoprotect the secretory cell population from opportunistic infections. In the method, a population of pleuripotential stem cells are transfected with a gene construct comprising the hCFTR gene in a manner designed to cause expression of the hCFTR gene, wherein, upon expression of the hCFTR gene and upon development and differentiation of the pleuripotential stem cell population, the secretory cell population is formed.

In a preferred embodiment, the gene construct comprises a viral vector. In another preferred embodiment, the viral vector is an adenoviral vector. In another preferred embodiment, the transfection of the pleuripotential stem cells is accomplished in vivo. In another preferred embodiment, the transfection of the pleuripotential stem cells is accomplished in vitro. In another preferred embodiment, the factors comprise glycoconjugates and lipids. In another preferred embodiment, the factors that are immuno-protectant to the cell population and mitigate bacterial infection, such as infection with *Pseudomonas aeruginosa*.

In accordance with a sixth aspect of the present invention, there is provided a secretory cell population that is derived from a pleuripotential stem cell population after transfection with, and expression of, a gene construct comprising the hCFTR gene and development and differentiation of the pleuripotential stem cell population.

In a preferred embodiment, the gene construct comprises a viral vector. In another preferred embodiment, the viral vector is an adenoviral vector. In another preferred embodiment, the transfection of the pleuripotential stem cells is accomplished in vivo. In another preferred embodiment, the transfection of the pleuripotential stem cells is accomplished in vitro. In another preferred embodiment, the secretory cell population secretes factors comprising glycoconjugates and lipids. In another preferred embodiment, the factors that are immunoprotectant to the secretory cell population. In another preferred embodiment, the factors mitigate bacterial infection, such as infection with *Pseudomonas aeruginosa*.

In accordance with a seventh aspect of the present invention, there is provided a pleuripotential stem cell differentiation factor comprising a gene corresponding substantially to hCFTR gene.

In accordance with an eighth aspect of the present invention, there is provided a method to treat opportunistic infections in a mammal, comprising administering an isolated immunoprotectant factor selected from the group consisting of glycoconjugates and lipids in a suitable carrier to affected cells and/or tissues.

In a preferred embodiment, the opportunistic infection is associated with a disease. In another embodiment, the disease is selected from the group consisting of *Pneumocystis carinii* pneumonia (PCP), cystic fibrosis (CF), acute respiratory distress syndrome (ARDS), necrotizing enteral colitis, SCIDS, ADA, immunosuppressed and diarrheal disease. The immunoprotectant factors can be derived from secretory cell populations as described above.

In a ninth aspect of the present invention, there is provided a composition for protecting cells from opportunistic infections comprising an agent selected from the group consisting of glycoconjugates and lipids, wherein the agent is substantially similar or identical to a second agent isolated from a secretory cell population that is derived from a pleuripotential stem cell population after transfection with, and expression of, a gene construct comprising the hCFTR gene and development and differentiation of the pleuripotential stem cell population.

BRIEF SUMMARY OF THE INVENTION

Our laboratory transiently expressed cftr in utero and permanently corrected the lethal phenotype of the cftr−/− mouse. Some of the results were disclosed by Larson, Morrow et al. (1997). An in utero gene therapy did not permanently replace the cAMP-dependent chloride channel and continuous functioning CFTR was not required for the correction of the lethal intestinal obstruction of the cftr−/− mice. The first animals rescued by in utero CFTR lived for greater than one year old. Their untreated littermates do not survive into adulthood (>45 days of age). These results suggested that the rescue of the knockout mouse was due to a temporary requirement of CFTR for normal epithelial development in the intestines.

We have devised a way to apply methods that temporarily ameliorate CFTR deficiency to in utero therapy, with the surprising result that amelioration then extends beyond birth and beyond the duration of the temporary in utero effect to become long-lasting amelioration.

Possible means for the brief amelioration includes, but is not limited to, transgenic supplementation of the cftr gene, pharmaceutical stimulation of CFTR, in vivo transfer of purified CFTR protein into the apical membrane of nasal epithelia, and rescue or stimulation of latent CFTR protein molecules. For the purposes of the present invention, latent CFTR protein molecules are understood to be CFTR protein molecules that are from a mutant CFTR gene, functionally defective in any way, retained within the endoplasmic reticulum, or present in insufficient functional quantity. The present invention also includes, but is not limited to, methods for sparing CFHR function such as: pharmaceutical manipulation of alternative ion channels; transgenic manipulation of the expression of alternative ion channels; pharmaceutical manipulation of complimentary ion channels, for example the ENaC channel; and transgenic manipulation of complimentary ion channels, such as the ENaC channel.

One mode of the present invention comprises in utero treatment of an animal to temporarily mitigate the condition of CFTR deficiency by transgenic therapy, with the surprising result that the animal subsequently is relieved of many or all of the symptoms of cystic fibrosis. The treatment may comprise transfer of the CFTR gene by viral vector, liposome or other medium. Many examples of methods of genetic transfer are mentioned herein, and any of these as well as other methods of gene transfer not specifically mentioned, can be used to implement in utero gene therapy with long-lasting improvement on the symptoms of cystic fibrosis.

The present invention also may comprise drug therapy, such as with ATP, UTP, or other purinergic ligands; chemical chaperones, choride conductance stimulators such as xanthines and fluoride; inorganic pyrophosphates as disclosed in U.S. Pat. No. 5,686,114, issued to M. J. Welsh, Nov. 11, 1997, and complimentary channel regulators such as amiloride, triamterene and spironolactone. Other possible therapeutic agents are discussed herein and tabulated in Table 2 and Table 3; one of those listed could be utilized in the present invention. In addition, U.S. Pat. No. 5,620,676 issued to Jacobson; et al Apr. 15, 1997 discloses novel adenosine triphosphate (ATP), xanthine and uracil analogs, and these also could be used in the present invention.

Any compounds not explicitly mentioned herein could be utilized in the invention if its in utero use is sufficient to at least temporarily ameliorate the CFTR deficiency present in a patient. The inventors provide examples of dosages and times of treatments; and other ways to vary these conditions are known to skilled workers. Pharmaceutically acceptable carriers are materials useful for the purpose of administering the medicament, which are preferably sterile and non-toxic, and may be solid, liquid, or gaseous materials, which are otherwise inert and medically acceptable, and are compatible with other active ingredients. The pharmaceutical compositions may contain other active ingredients as preservatives. Pharmaceutical dosage forms and drug delivery systems are described by H. C. Ansel, N. G. Popovich and L. V. Allen, Jr. in *Pharmaceutical dosage Forms and Drug Delivery Systems,* 6th ed. Williams and Willkins (1995).

Relief from or alleviation of symptoms may comprise resistance to infection by any organism, but especially by those organisms known to infect CF patients, for example *Staphylococcus aureus, Haemophilus influenzae, Pseudomonas aeruginosa, Burkholderia (Pseudomonas) cepacia, Stenotrophomonas (Xanthomonas) maltophilia, B. gladioli, Aspergillus fumigatus* and nontuberculous mycobacteria, and most especially by *Pseudomonas aeruginosa;* changes in histological staining of tissue, including but not limited to, the stains mentioned herein; gastrointestinal problems such as obstructions and the like; improved respiratory function; and improved function of exocrine glands of the intestine or bronchus. Other symptoms not explicitly mentioned may also be relieved.

A surprising aspect of this invention is the possiblity that over-dosing of the cftr-treatment and/or other in utero therapy targeted to temporarily mitigate cftr deficiency may result in an overcorrection. The over-correction is manifested as hyperplastic growth within the lung. Thus, the effective dose may be determined by any means appropriate for detecting hyperplastic tissue. Description of the use of such histological techniques is provided in Advanced Histopathology by Gordon W. H. Stamp, N. A. Wright, Springer Verlag, 1990; and a Textbook of Histology--by Bloom and Fawcett, 12th Edition Chapman & Hall, 1994. In particular, we have shown that the application of H&E stain to lung sections reveals the extent of hyperplasia. Thus, use of the H&E stain on respiratory tissue, as well as other means for detecting hyperplasia, would allow a person skilled in the art to optimize the therapeutic dose and timing of its administration.

As used herein, the term "effective dose" is denoted to mean a predetermined amount sufficient to ameliorate a CFTR deficiency in utero, with the amelioration extending past the subsequent birth of the treated subject. Manifestations of CFTR deficiency are usually described as cystic fibrosis, but other terms are used, for example congenital absence of vas deferens (CAVD).

Another mode of the present invention is to apply our observations for diagnostic/prognostic purposes, and for monitoring the progress of therapy. These observations include the use of stains to monitor the conditions of tissue. In addition to the histological texts previously mentioned, Molecular Probes, Inc. of Eugene, Oreg., USA, has published a comprehensive manual by R. P. Haugland that describes the use of fluorescent stains: *Handbook of Fluorescent Probes and Research Chemicals,* 6th ed (1996). In particular, histological stains include the use of means to detect changes in intracellular Ca++ after application of the therapy of the present invention. Means of detecting changes in intracellular Ca++ would include particularly the use of Ca++ specific stains and the use of Ca++ specific sensors, including but not limited to, the one described by Shalom et al (Shalom, Strinkovski et al. 1997). The Shalom sensor is based on a pulled micropipet, filled with a conducting porous sol-gel glass which has been doped with the fluorescent Calcium Green™ Ca2+ indicator. Such sensors are potentially capable of measuring Ca2+ concentrations as low as $10^{(-8)}$ M, in confined volumes, with a three-dimensional resolution which exceeds approximately 0.1 micron. Other techniques for measuring Ca++ and Ca++ flux are described in Methods in Cell Biology, vol. 40; ed. R. Nuccitelli, Academic Press (1994). Methods described in this text include microelectrode techniques, including calcium-specific electrodes (Chapter 4, Baudet et al) vibrating electrodes (Chapter 5, Smith et al), and patch clamp methods (Chapter 6, Leech and Holz); fluorescene techniques for imaging Ca++ (Part III); and the use of aequorin for Ca++ imaging (Part IV). Fluorescence techniques for Ca++ imaging include the use of a variety of indicator for Ca++, for example Calcium Green-1™, Calcium Green-2™, Calcium Green-5N™ fluo-3, indo-1, rhod-2, fura-2, fura red, indo-1, fura(-2)dextran and indo(-1)dextran. Appropriate histological techniques also include the use of ligands to stain purinergic receptors. Thus, use of these and similar physiological stains would allow a person skilled in the art to optimize the dose and timing of a therapy targeted to mitigating a CFTR deficiency in utero, particularly when used in conjunction with a stain for hyperplasia.

BRIEF DESCRIPTION OF THE DRAWING FIGURES

The file of this patent contains at least one drawing executed in color. Copies of this patent with color drawing (s) will be provided by the Patent and Trademark Office upon request and payment of the necessary fee.

Figure 1B:
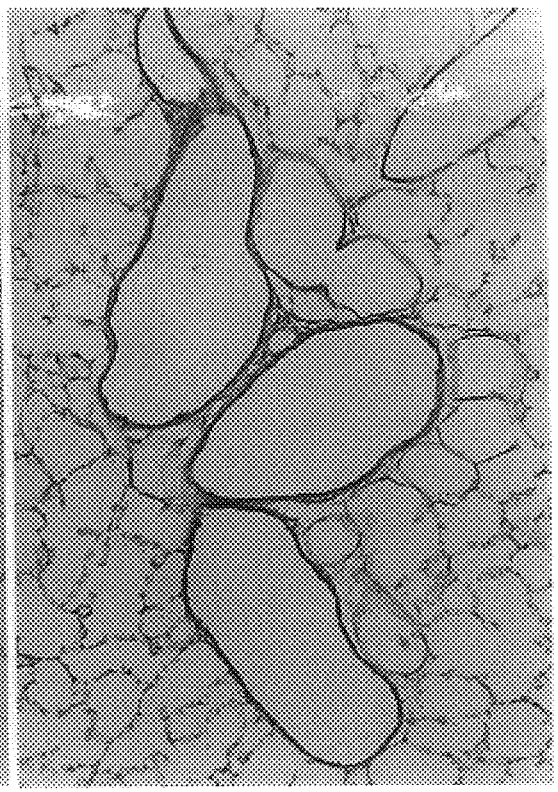

FIGS. 1A–B a pair of photomicrographs showing the histochemical localization of β-galactosidase in the bronchioles of seven day old rat pups. FIG. 1a is from a seven day old control rat pup previously injected with saline into the amniotic fluid at 16 days of gestation (10× magnification). FIG. 1b shows the high levels of β-galactosidase expression in the bronchioles of a seven day old rat pup injected with $10^8$ pfu ml–1 amniotic fluid of a replication defective adenoviral vector (AD5.CMVlacZ) at 16 days gestation (10×magnification).

Figure 2A:
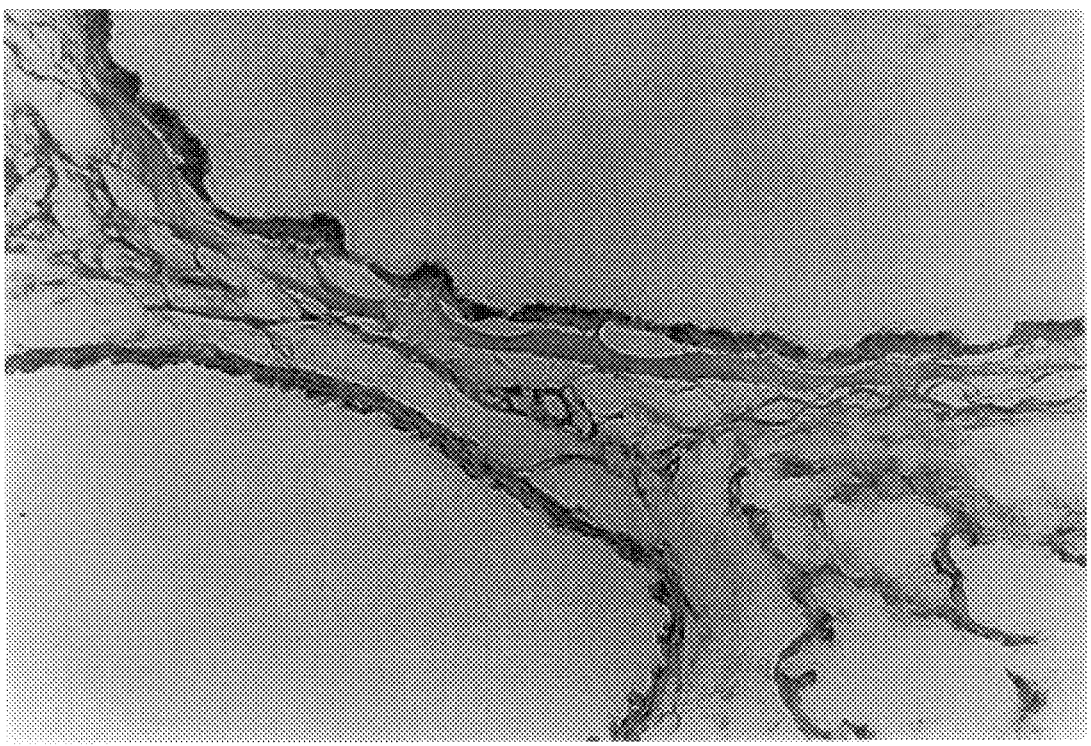
Figure 2B:
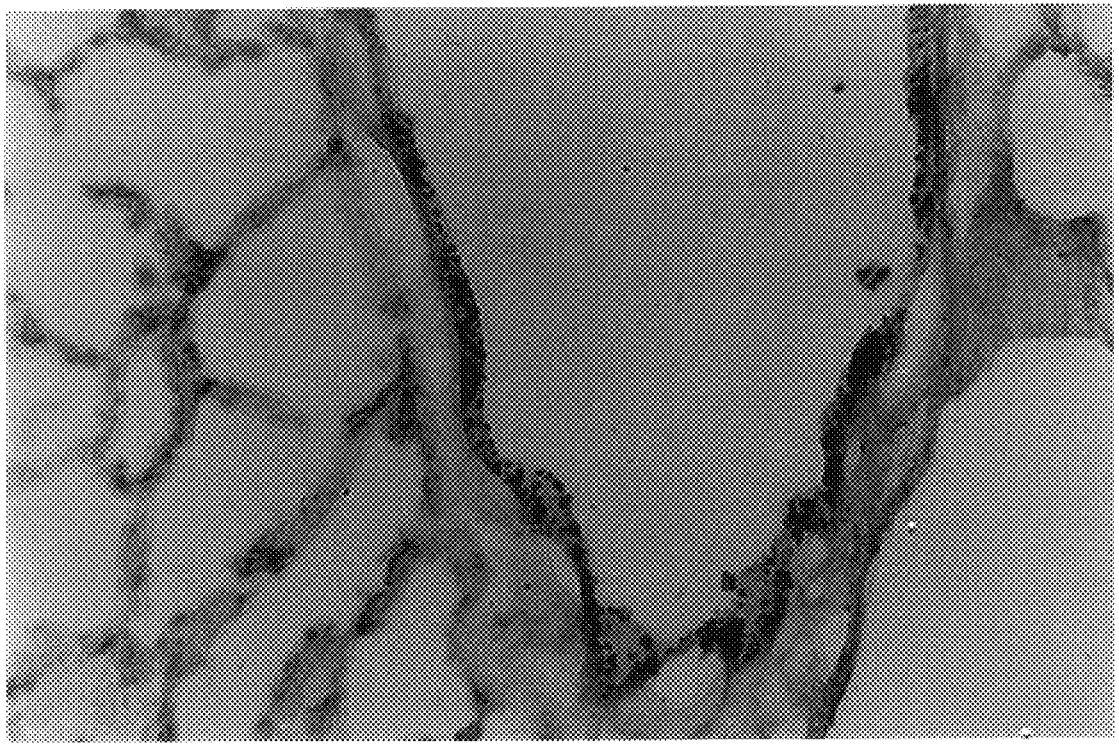

FIGS. 2A–B is a pair of photomicrographs showing the immunohisto-chemical localization of β-galactosidase in the bronchi of seven day old rat pups. FIG. 2a shows the results from a saline injected control animal (20×magnification). FIG. 2b shows the results from an animal injected with $10^8$ pfu ml–1 amniotic fluid of a replication defective adenoviral (AD5.CMVlacZ) at 16 days gestation (20×magnification).

Figure 3A:
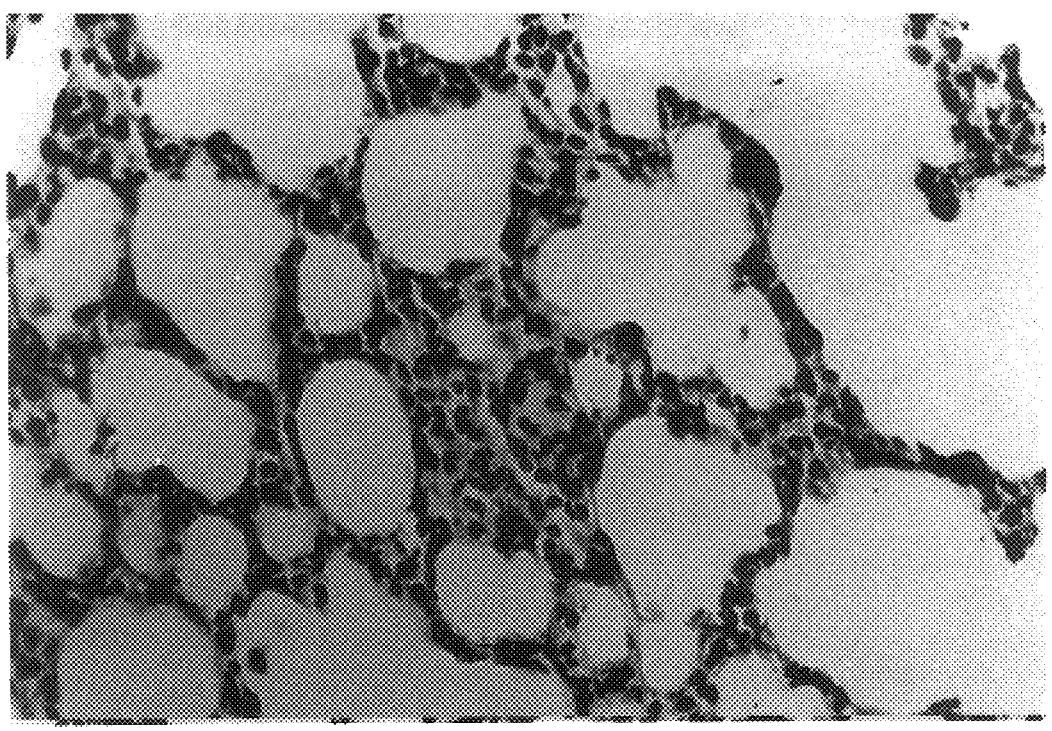
Figure 3B:
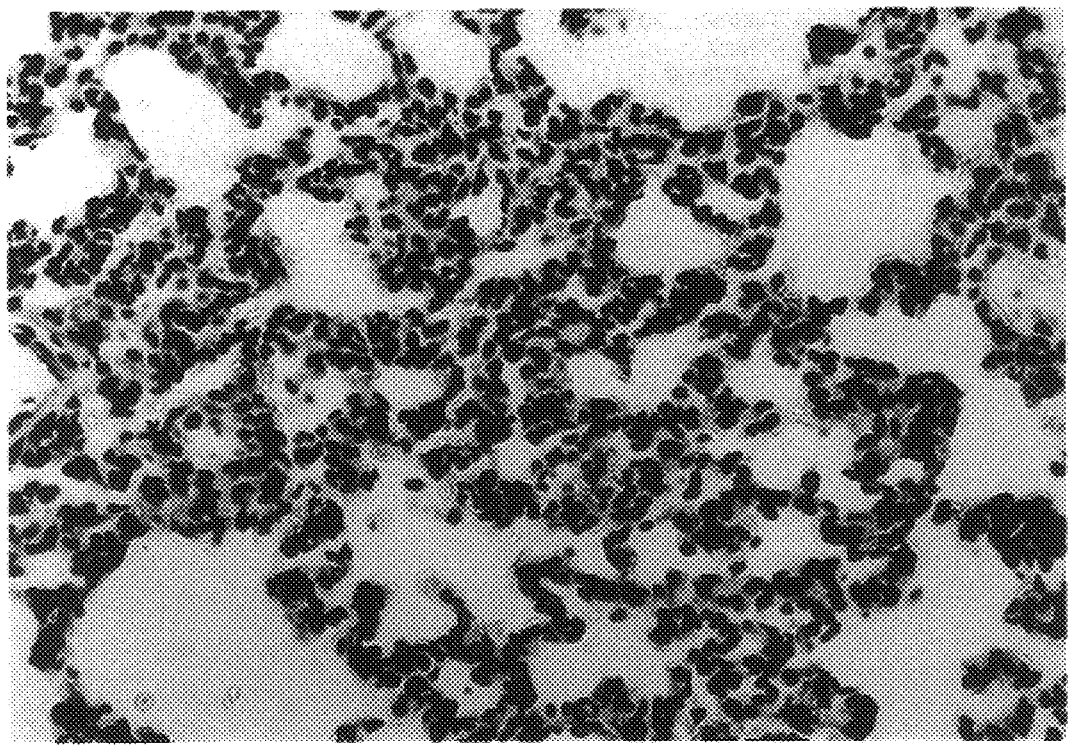

FIGS. 3A–B is a pair of photomicrographs showing hematoxylin and eosin stained tissues from the lungs of five day old rat pups injected with either LacZ or a CFTR gene through injection of $10^8$ pfu ml–1 amniotic fluid of a replication defective adenoviral vector at 17 days gestation. The lung tissues were parallel processed at ten days after infection. FIG. 3a is from a pup infected with LacZ adenoviral vector (AD5.CMVLacZ). FIG. 3b is from a pup infected with a CFTR adenoviral vector (Av1CF2). Each of the Figures are shown at 10×magnification.

Figure 4A:
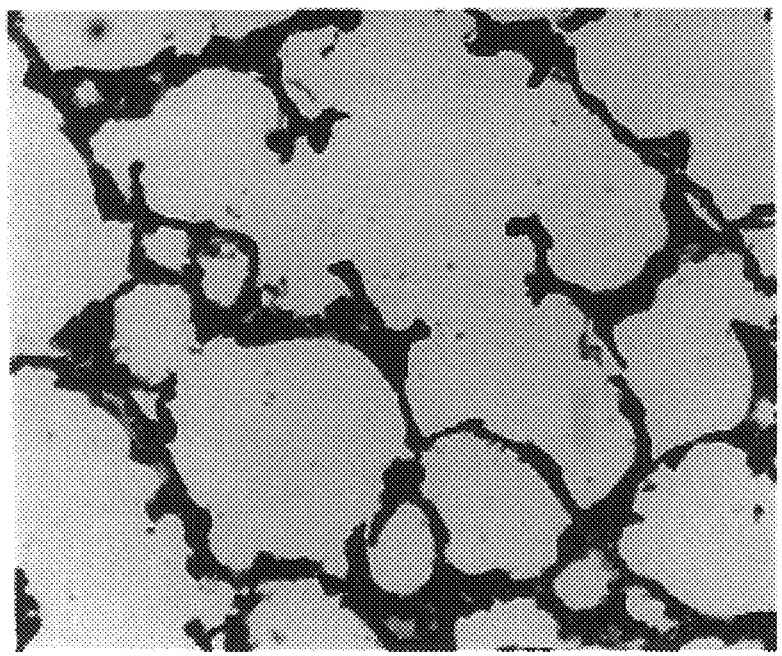
Figure 4B:
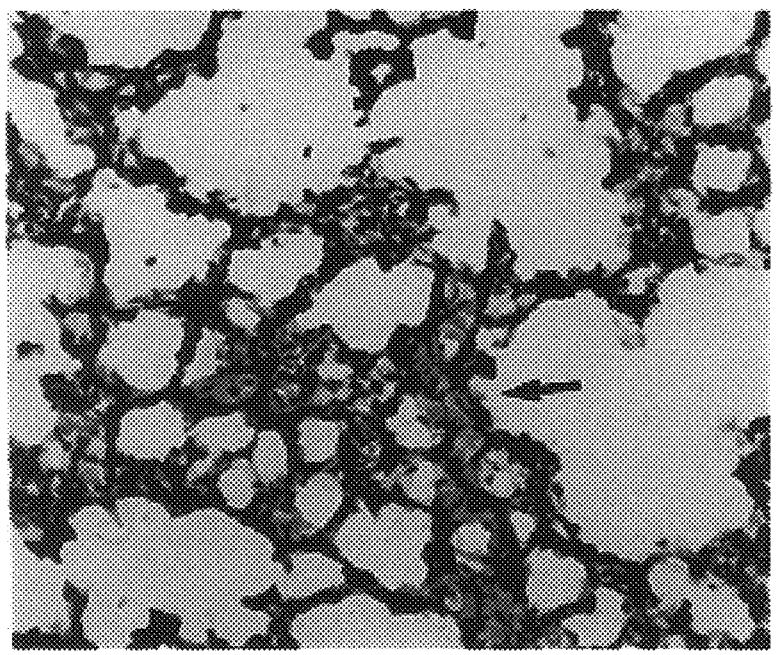

FIGS. 4A–B is a pair of photomicrographs showing the immunohisto-chemical localization of CFTR in rats injected with $10^8$ pfu ml–1 amniotic fluid of a replication defective LacZ or hCFTR adenoviral vector at 17 days gestation. The lung tissues were parallel processed at ten days after infection with hCFTR-specific monoclonal antibodies and stained with hematoxylin. FIG. 4a is from a pup infected with LacZ adenoviral vector (AD5.CMVLacZ). FIG. 4b is from a pup infected with a CFTR adenoviral vector (Av1CF2). Each of the Figures are shown at 20×magnification.

Figure 5A:
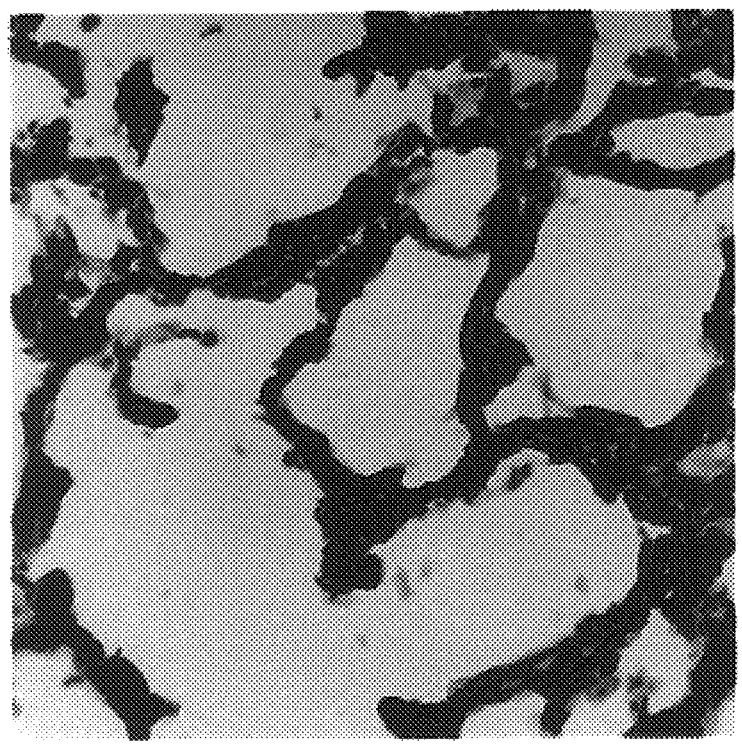
Figure 5B:
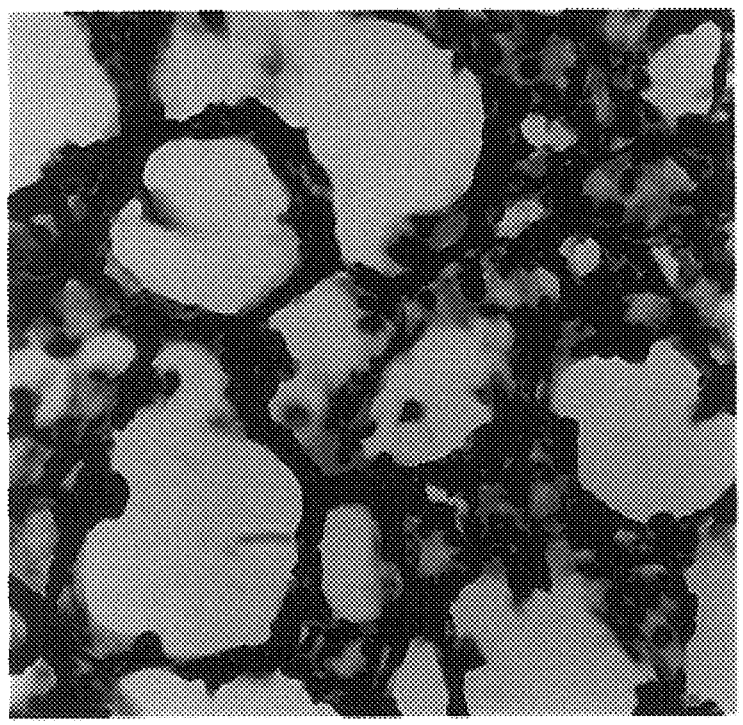
Figure 5C:
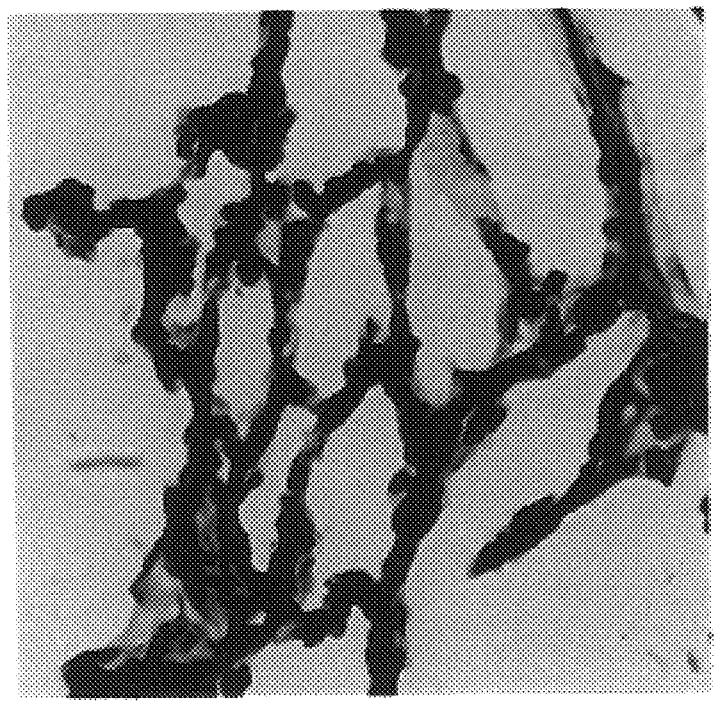
Figure 5D:
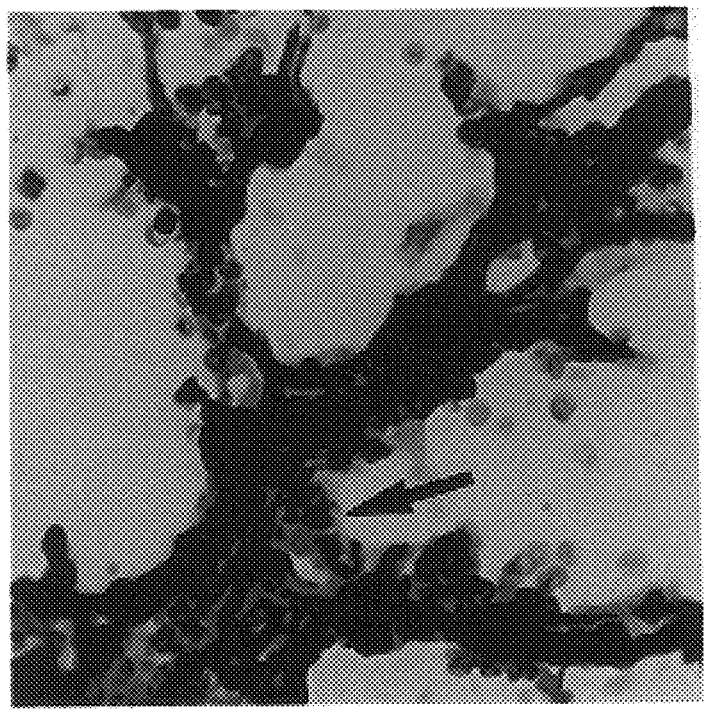

FIGS. 5A–D is a series of photomicrographs showing the expression of CFTR in 12 and 22 day old rats which were treated with $10^8$ pfu ml–1 amniotic fluid of a replication defective LacZ or hCFTR adenoviral vector at 17 days gestation. FIG. 5a is from a 12 day old pup infected with a LacZ adenoviral vector (AD5.CMVLacZ). FIG. 5b is from a 12 day old pup infected with a CFTR adenoviral vector (Av1CF2). FIGS. 5c and 5d are from a 22 day pup. Each of the Figures are shown at 20×magnification.

Figures 6A, 6B:
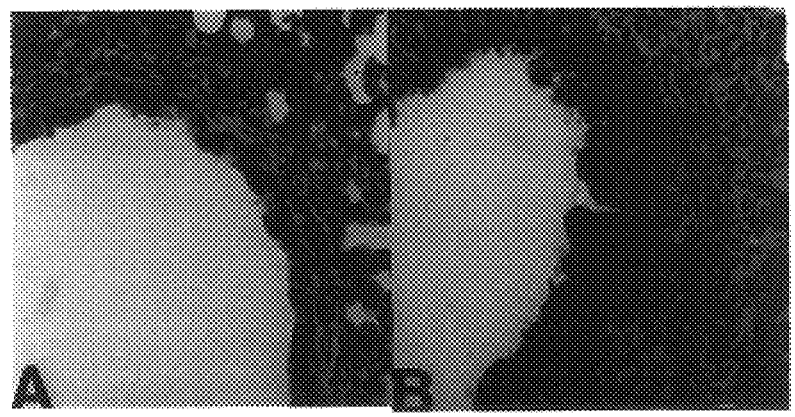
Figures 6C, 6D:
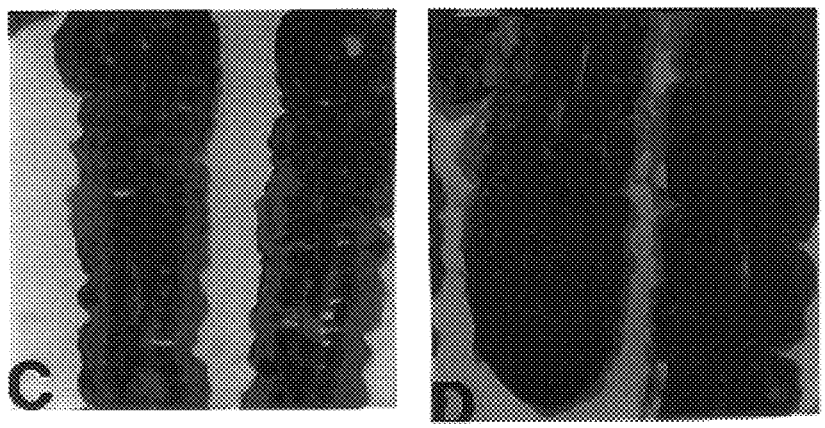
Figure 6E:
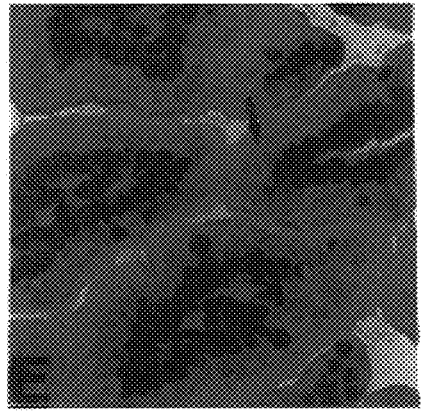

FIGS. 6A–E is a pair of photomicrographs showing tissues parallel processed and stained for glycoconjugates with alcian blue/periodic acid schiff (PAS). Tissues were obtained from 5 day old rats treated with $10^8$ pfu ml–1 amniotic fluid of a replication defective LacZ or hCFTR adenoviral vector at 17 days gestation. FIG. 6a is from a pup infected with a LacZ adenoviral vector (AD5.CMVLacZ). FIG. 6b is from a pup infected with a CFTR adenoviral vector (Av1CF2). Each of the Figures are shown at 20×magnification.

Figure 7A:
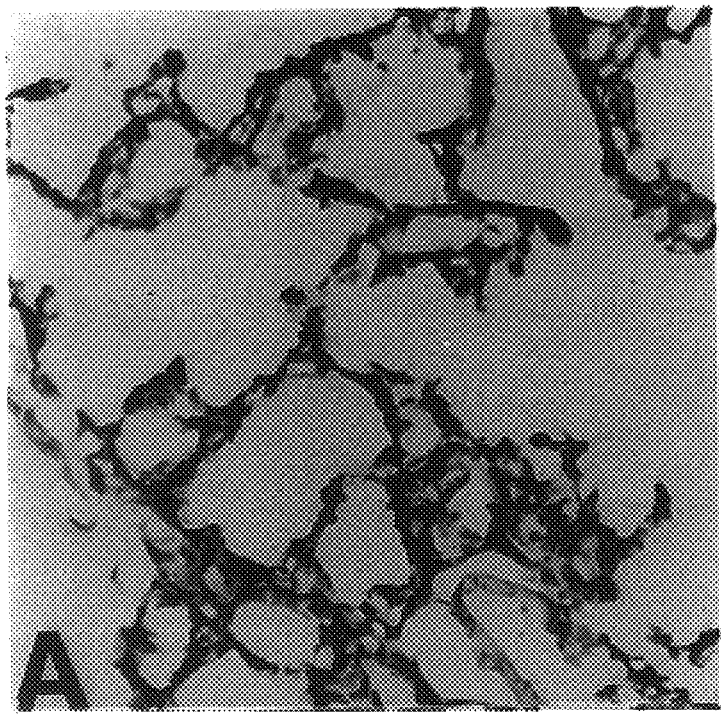
Figure 7B:
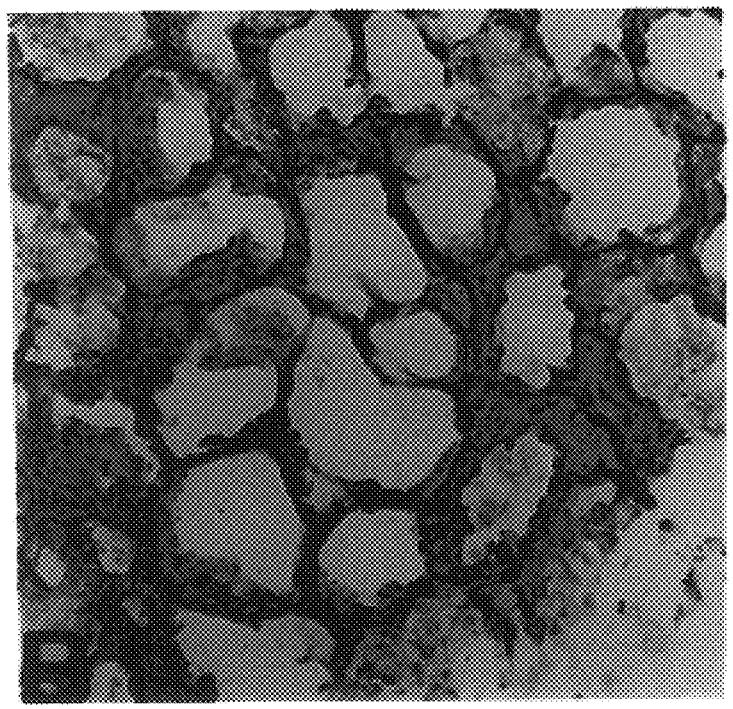

FIGS. 7A–B is a pair of photomicrographs showing tissues parallel processed and stained for lipids with Oil red O. Tissues were obtained from 5 day old rats treated with $10^8$ pfu ml$^{-1}$ amniotic fluid of a replication defective LacZ or hCFTR adenoviral vector at 17 days gestation. FIG. 7a is from a pup infected with a LacZ adenoviral vector (AD5.CMVLacZ). FIG. 7b is from a pup infected with a CFTR adenoviral vector (Av1CF2). Each of the Figures are shown at 20×magnification.

Figure 8A:
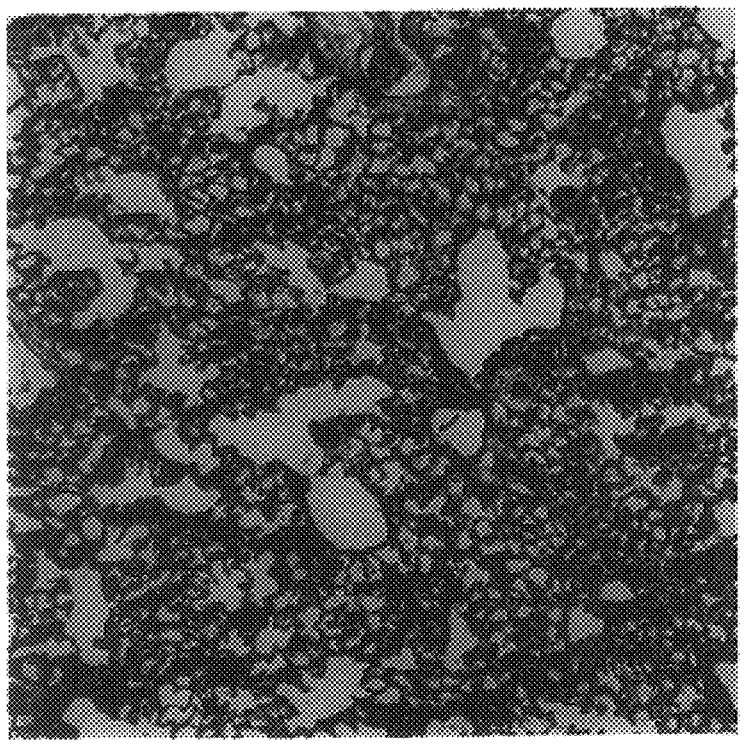
Figure 8B:
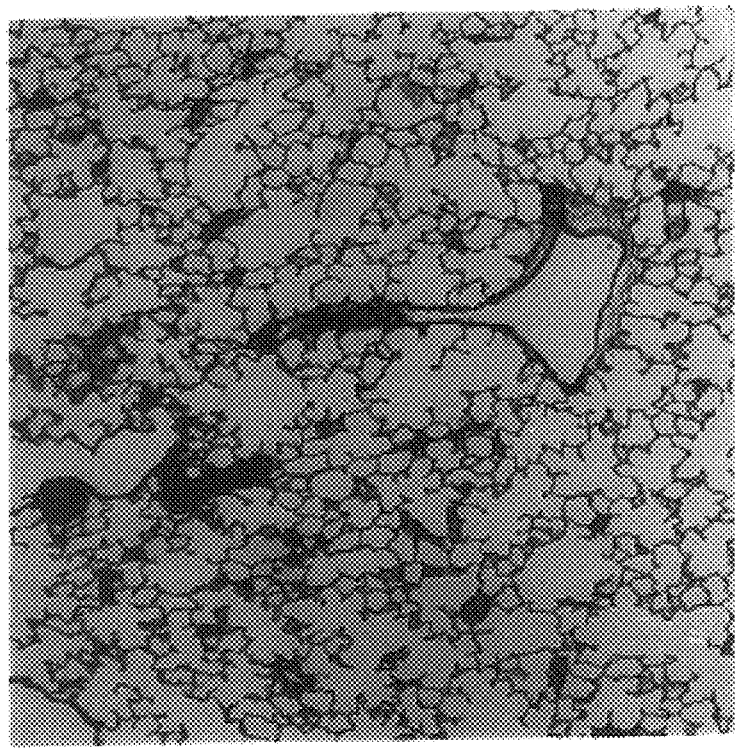
Figure 8C:
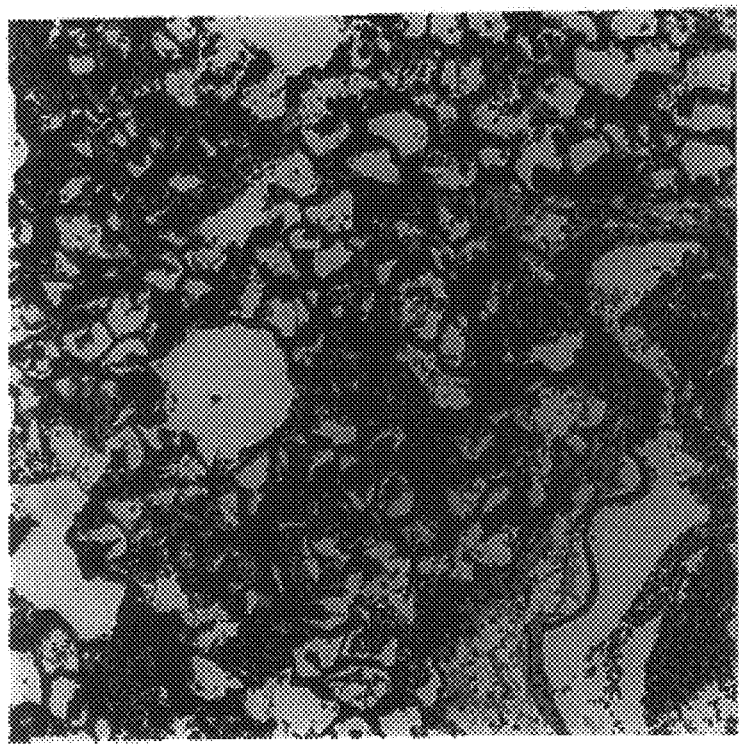
Figure 8D:
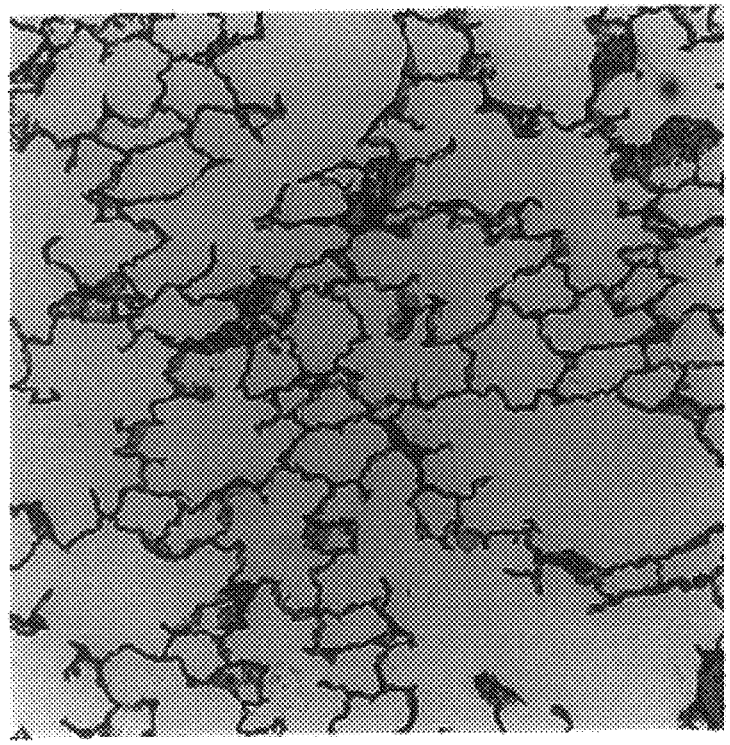

FIGS. 8A–D is a pair of photomicrographs showing hematoxylin and eosin stained tissues from the lungs of three month old rat pups infected with either a LacZ or hCFTR gene through infection with $10^8$ pfu ml$^{-1}$ amniotic fluid of a replication defective adenoviral vector at 17 days gestation. The pups were challenged by an intratacheal injection of *Pseudomonas aeruginosa* and sacrificed 6 hours later. FIGS. 8a and 8c are from a pup infected with Lac Z adenoviral vector (Ad5.CMVLacZ), shown at 4× and 10×magnification, respectively. FIGS. 8b and 8d are from a pup infected with a CFTR adenoviral vector (Av1CF2), shown at 4× and 10×magnification.

Figure 9:
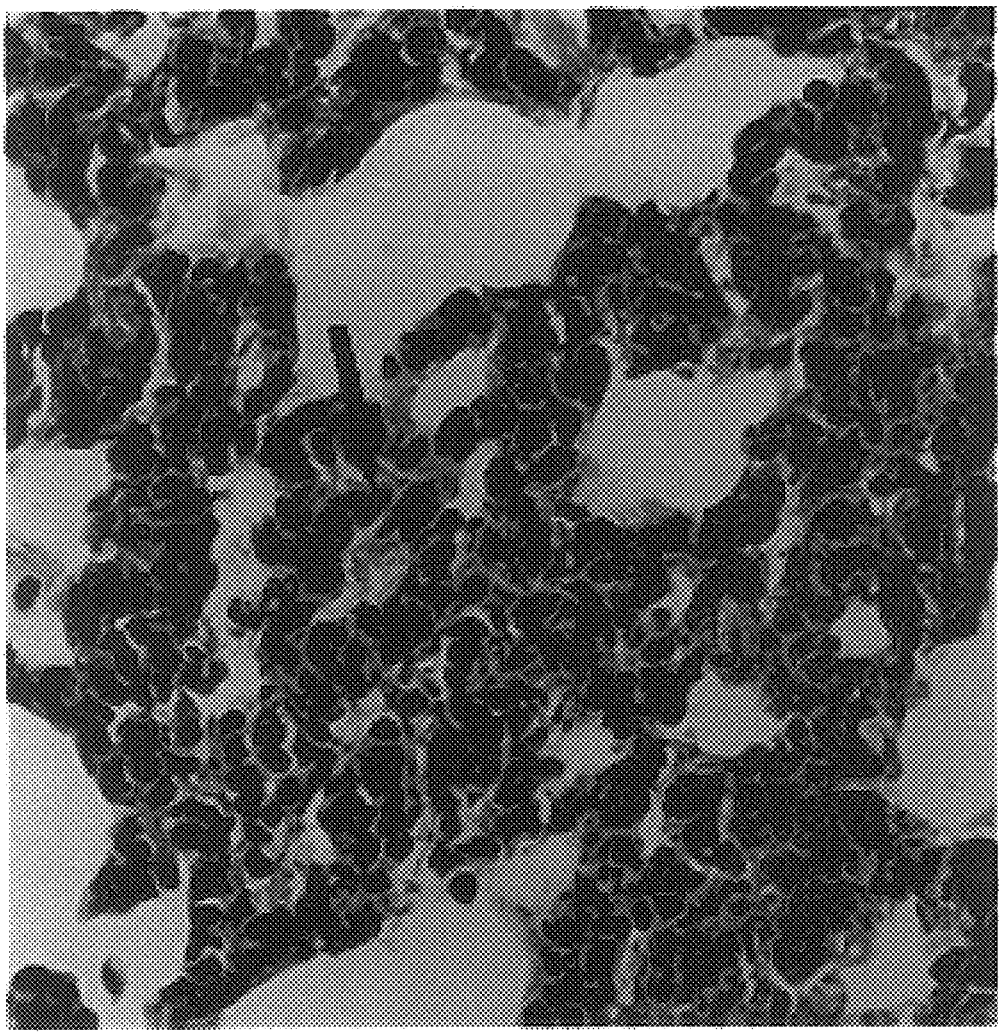

FIG. 9 is a photomicrograph showing tissues stained for glycoconjugates with periodic acid schiff (PAS). Tissues were obtained from a 12 day old rat treated with $10^8$ pfu ml$^{-1}$ amniotic fluid of a replication defective hCFTR adenoviral vector (Av1CF2) at 17 days gestation. The Figure is shown at 40×magnification.

Figure 10A:
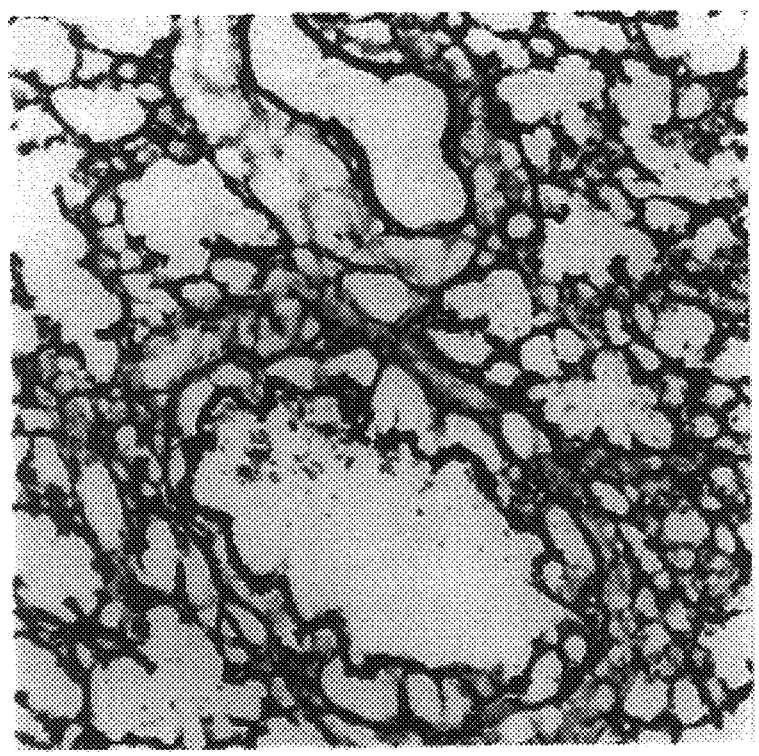
Figure 10B:
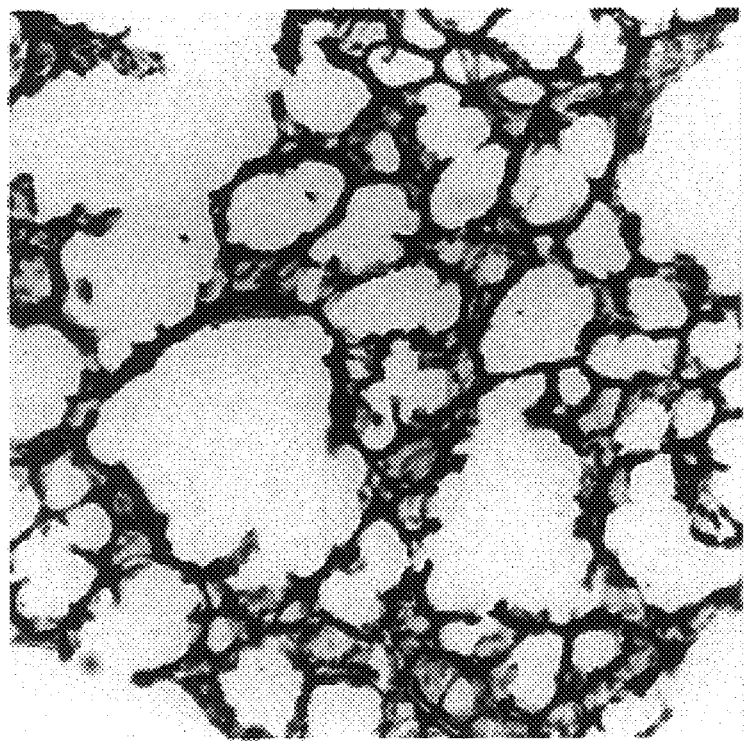
Figure 10C:
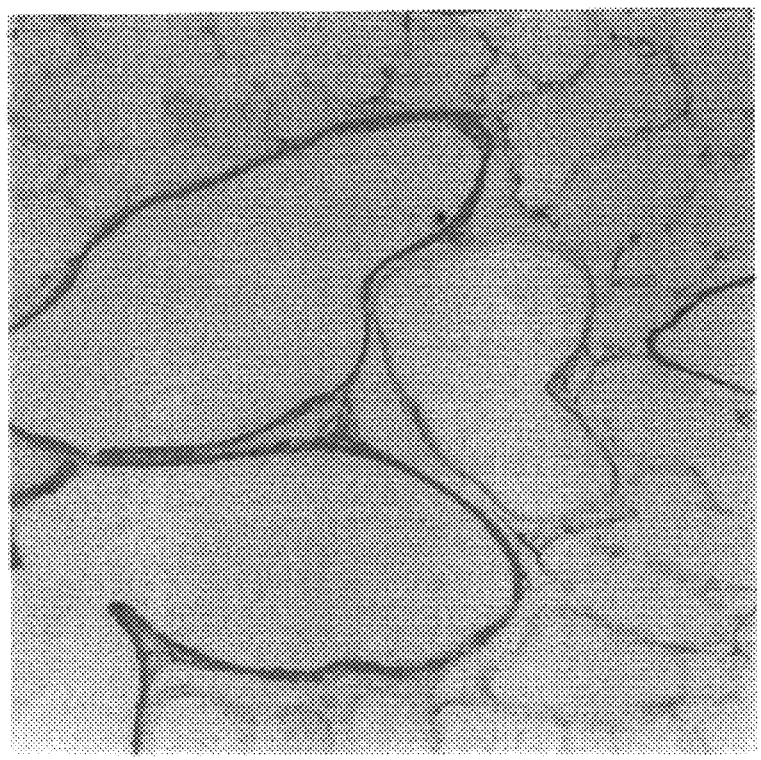
Figure 10D:
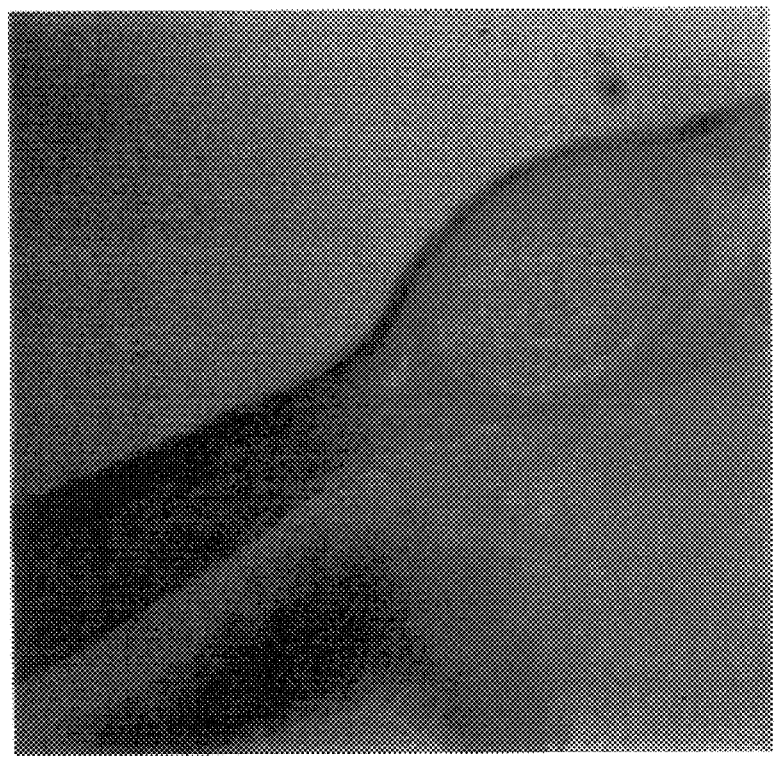
Figure 11A:
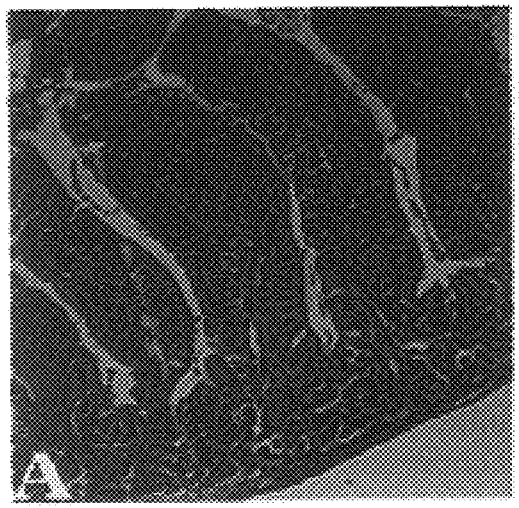
Figure 11B:
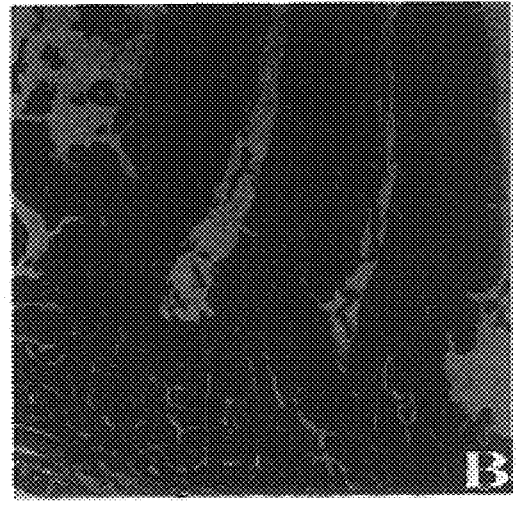
Figure 11C:
Figure 11D:
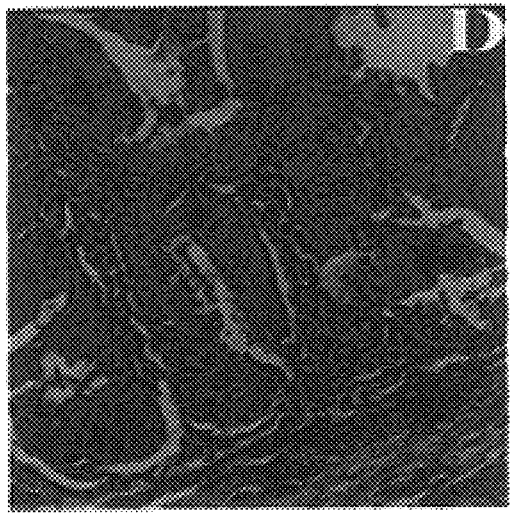

FIGS. 10A–D is a series of photomicrographs showing the distribution of CFTR-induced cells and cells expressing the LacZ transgene. Tissues were taken from the lungs of 7 and 12 day old rat pups infected with either a LacZ or hCFTR gene through infection with $10^8$ pfu ml$^{-1}$ amniotic fluid of a replication defective adenoviral vector at 17 days gestation. FIGS. 10a and 10b are from a pup infected with a CPTR adenoviral vector (Av1CF2) and immunohisto-chemically stained with a monoclonal antibody for CFTR, shown at 10× and 20×magnification, respectively. FIGS. 10c and 10d are from a pup with Lac Z adenoviral vector (Ad5.CMVLacZ) and immunohistochemically stained with Xgal for β-galactosidase, shown at 10× and 20×magnification, respectively.

FIGS. 11A–D Alcian Blue/Periodic Acid Schiff stain of intestines from normal heterozygote and in utero cftr-treated cftr–/– mice. The intestines from animals greater than 75 days of age was fixed and paraffin blocks section for staining with Alcian Blue/PAS and microscopic analysis at 40× (Panels A and B) and 250×(Panels C and D). Panels A and C, normal cftr+/–; Panels B and D, in utero cftr-treated, cftr–/–.

FIGS. 12A–D SNA-positive glycoconjugates in the lungs from untreated and in utero cftr-treated heterozygous and knockout mice. Lungs from fetuses treated at 15–16 days gestation with either Ad5.CMVlacZ (Panels A and C) or Av1CF2 (Panels B and D) were fixed and embedded in paraffin blocks, then stained by immunohistochemistry with the lectin SNA. Panel A and C, cftr–/–; Panels B and D, cftr+/–.

Figure 13A:
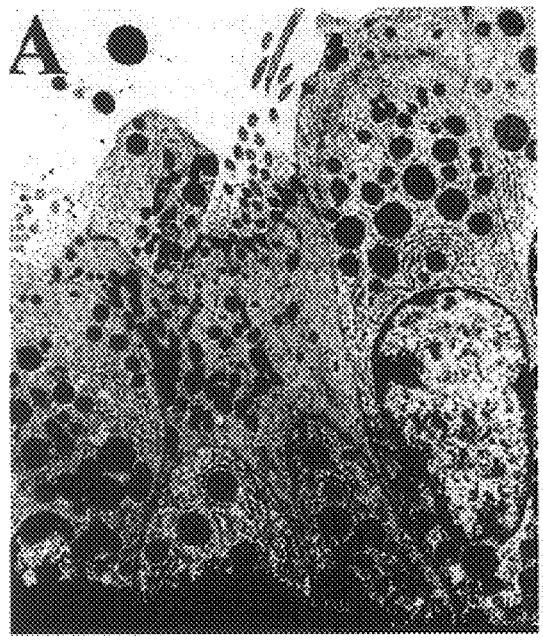
Figure 13B:
Figure 13C:
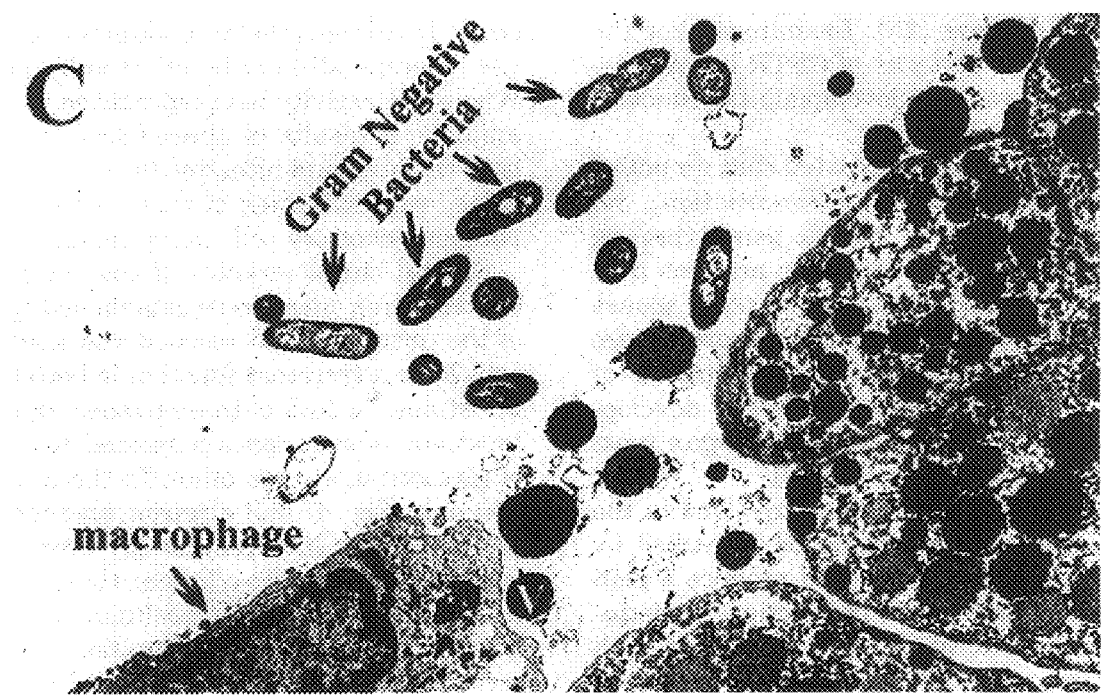

FIGS. 13A–C Electron microscopic examination of lungs from the untreated and in utero cdtr-treated cftr–/– mice. Lungs from a 40 day old untreated cftr–/– mouse (Panel A) and from a >75 day old in utero cftr-treated cftr–/– mouse (Panels B and C) were fixed and mounted in plastic for sectioning. Vesicles are indicated by the letter V. Magnification=7500×.

Figure 14:
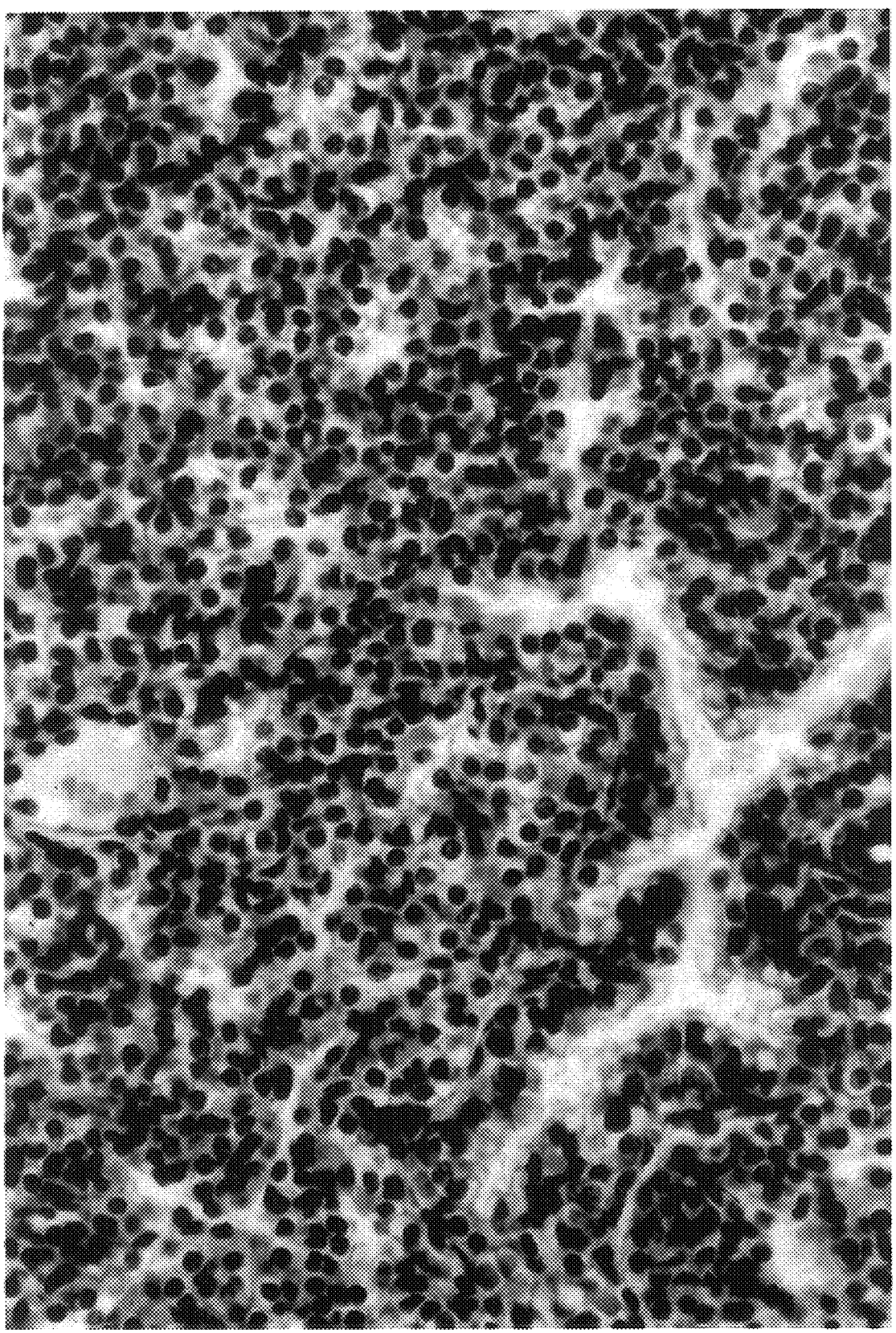

FIG. 14 shows H&E stained lung sections from cftr-treated mice.

Figure 15:
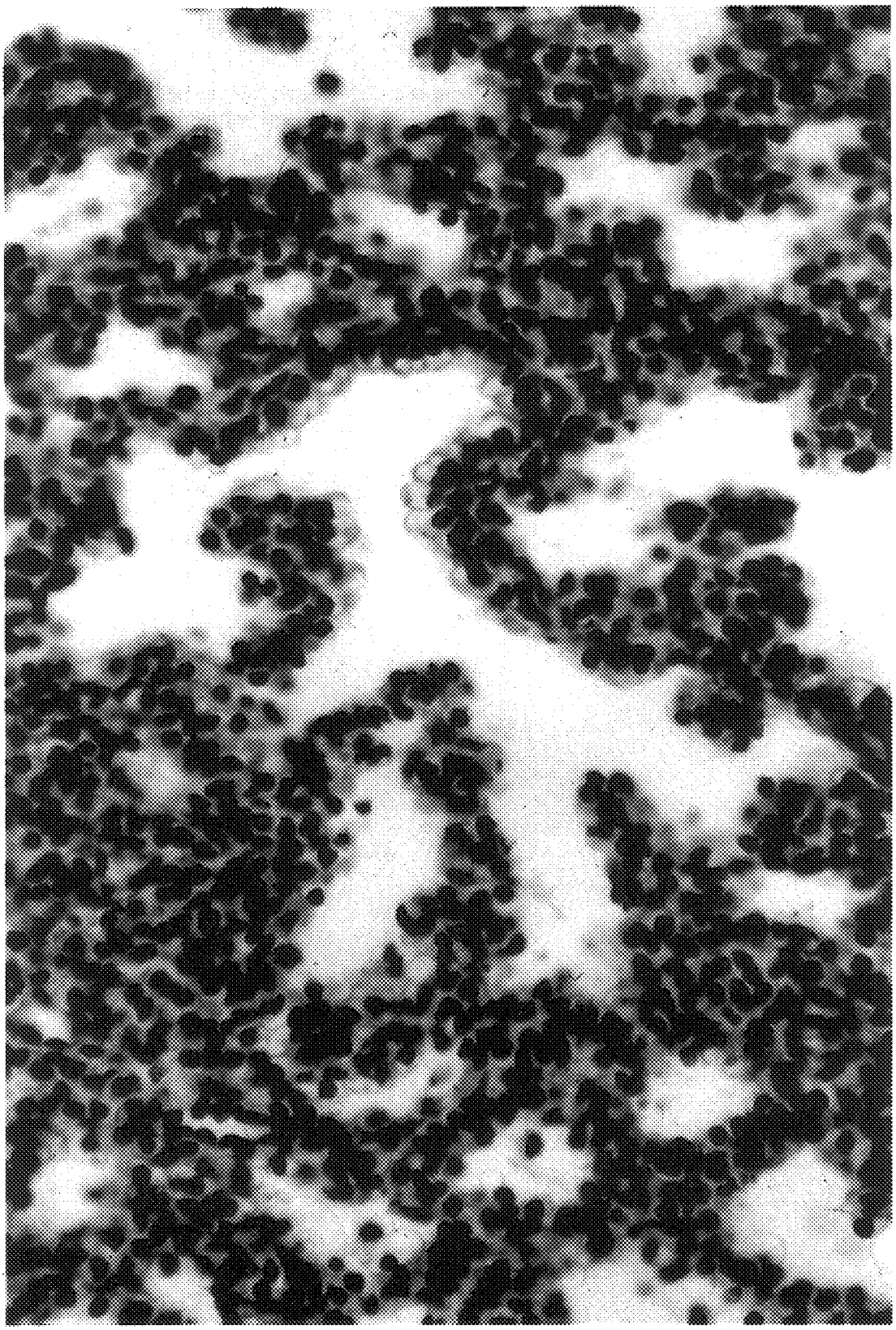
Figure 16A:
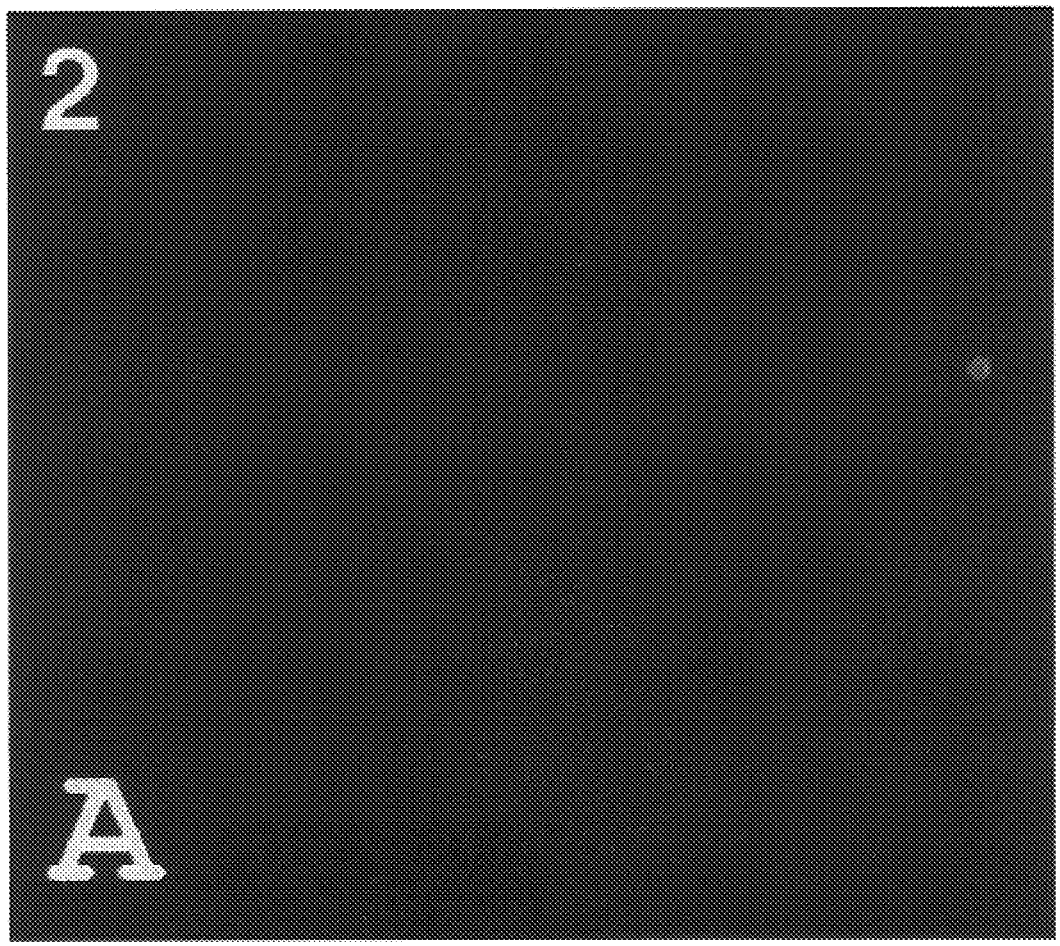
Figure 16B:
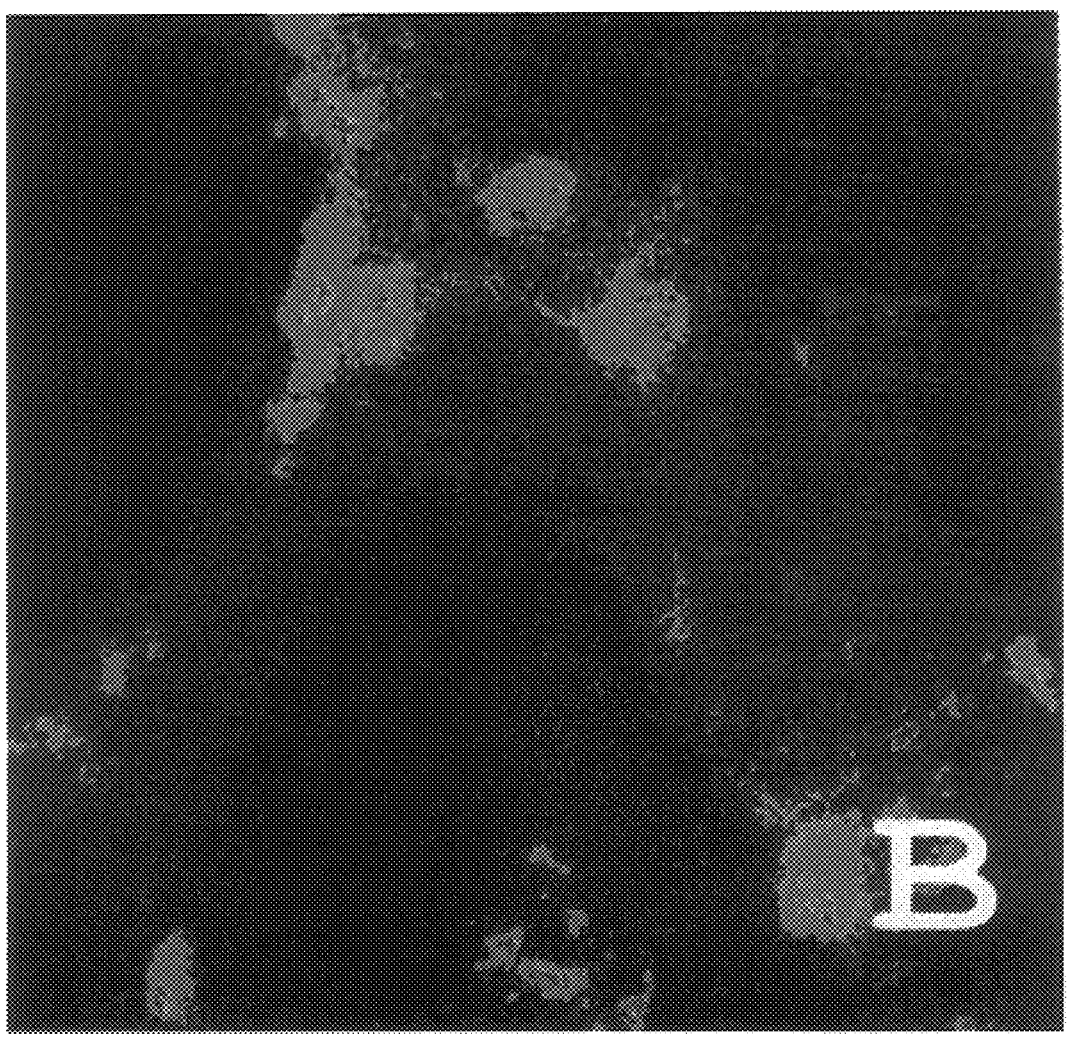
Figure 16C:
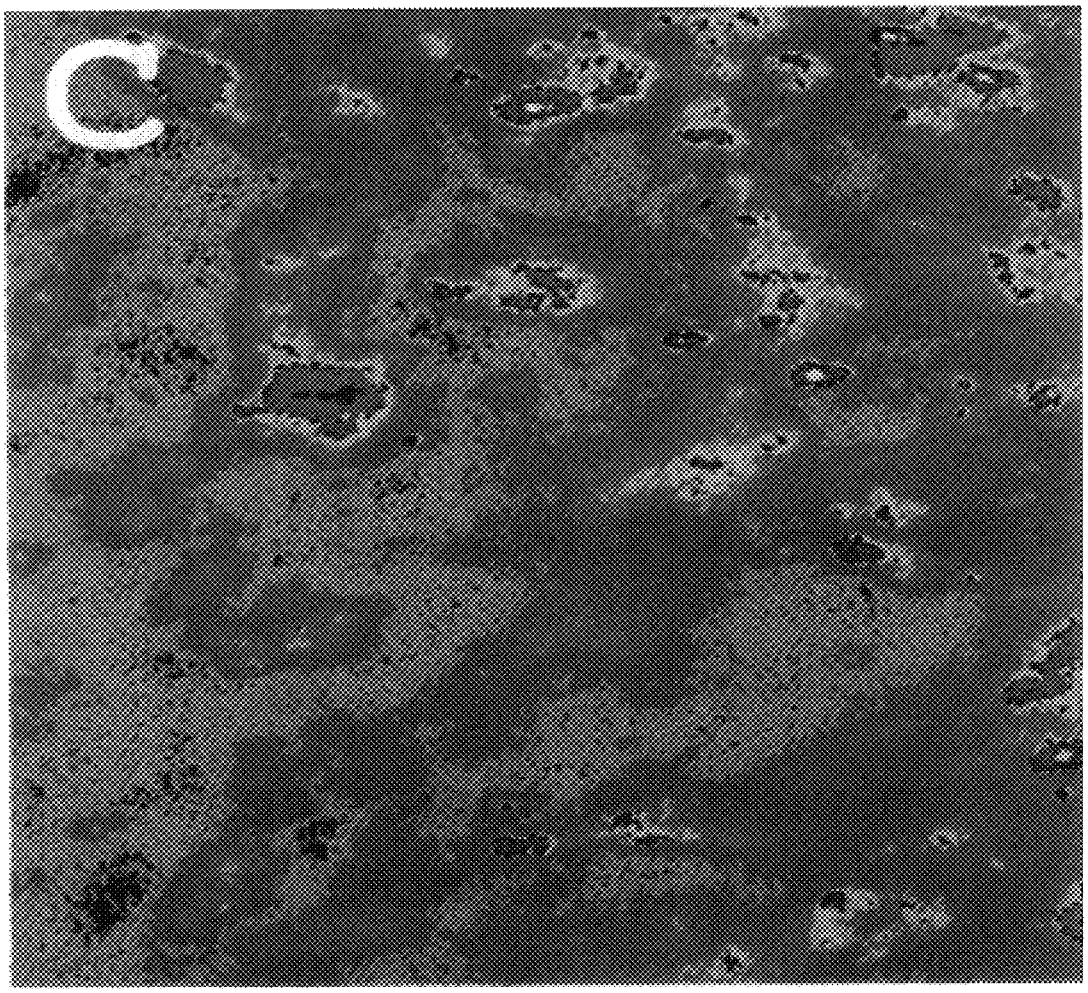
Figure 16D:
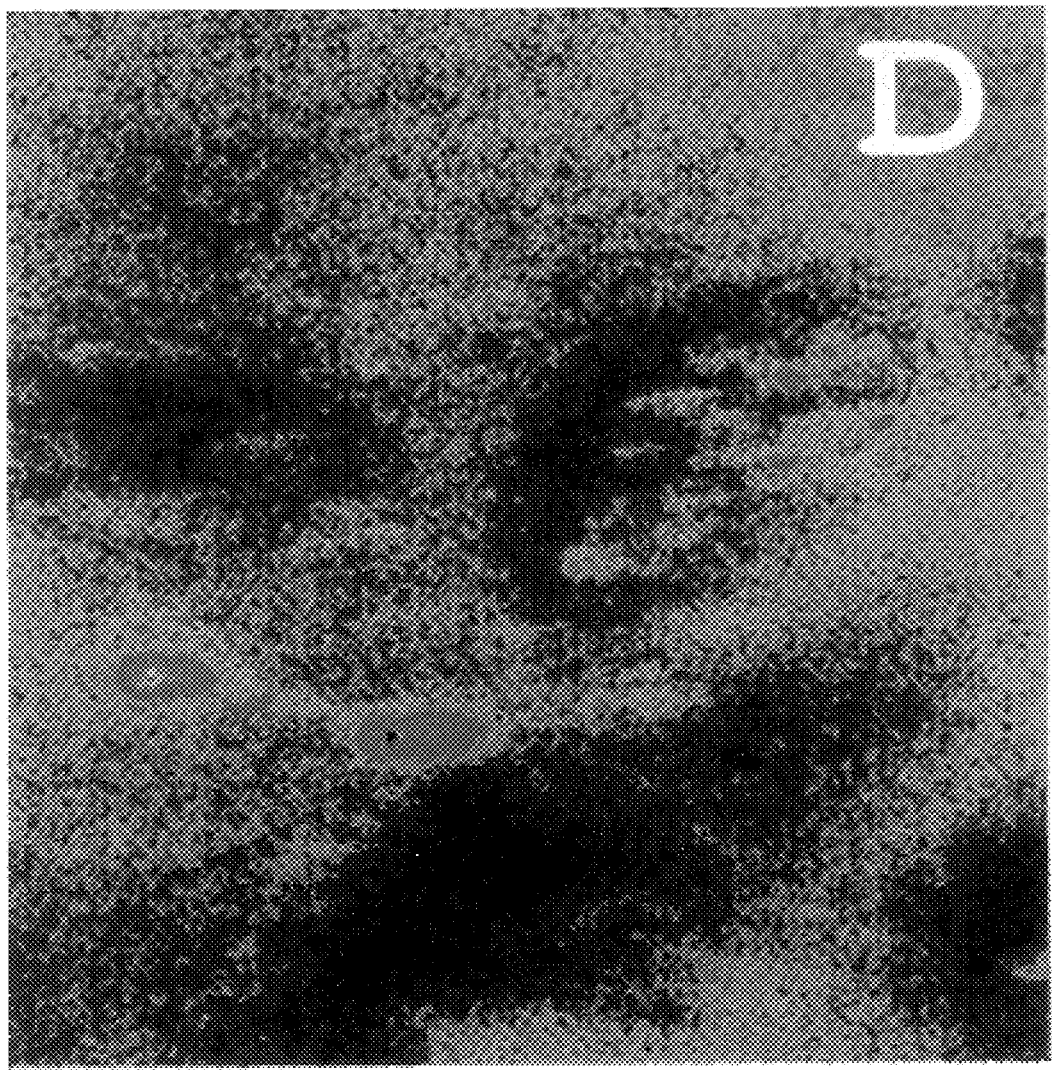
Figure 17A:
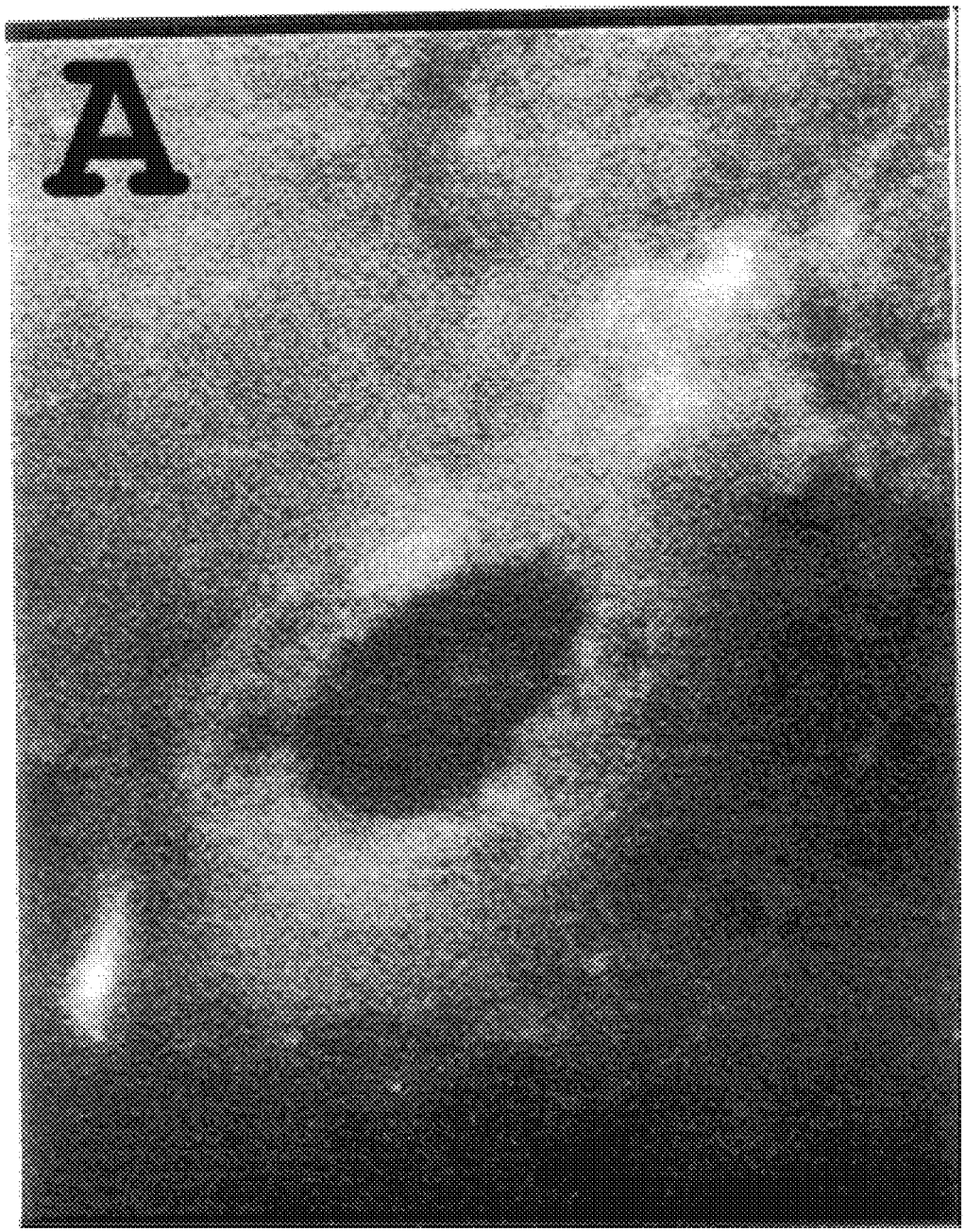
Figure 17B:
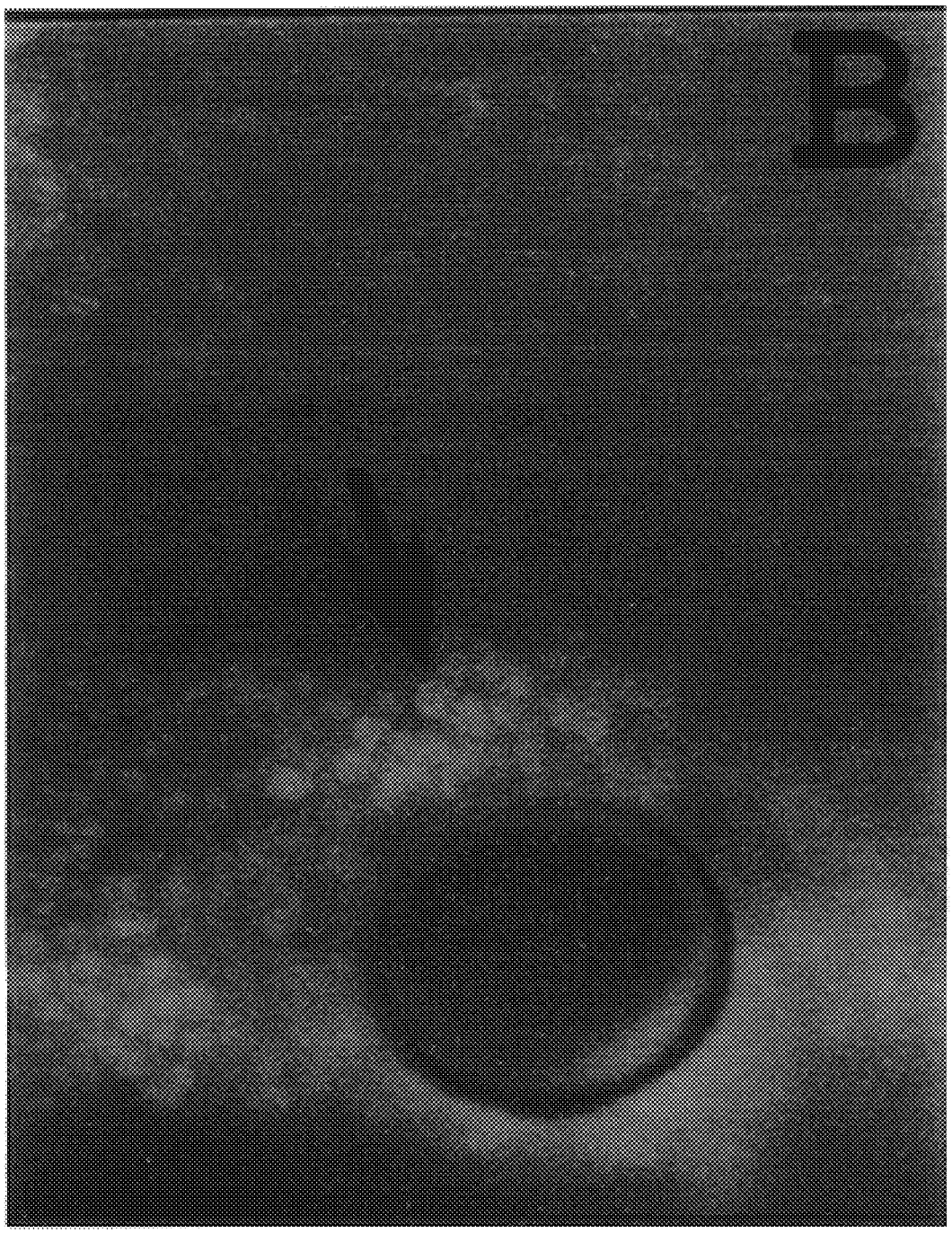
Figure 17C:
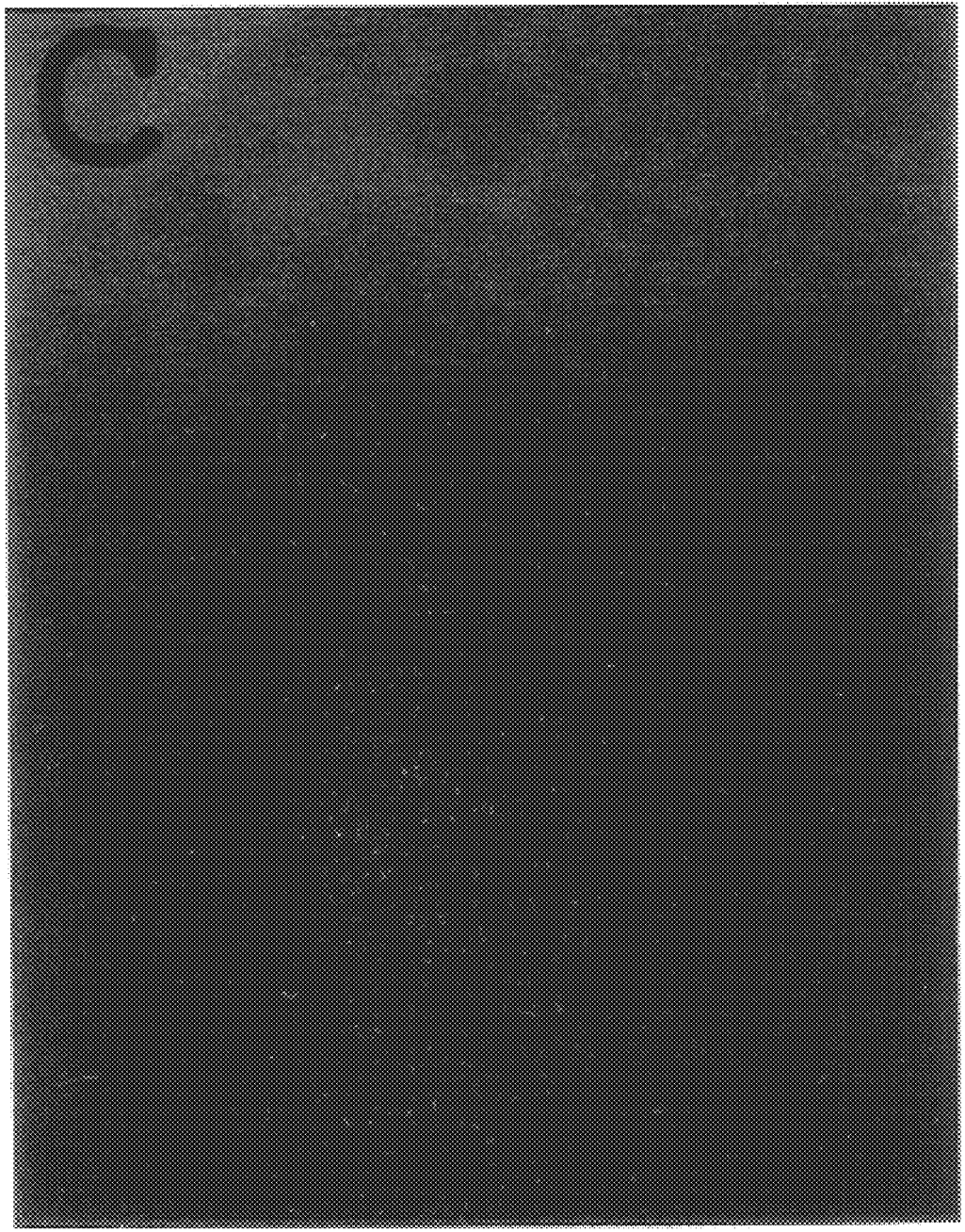
Figure 17D:
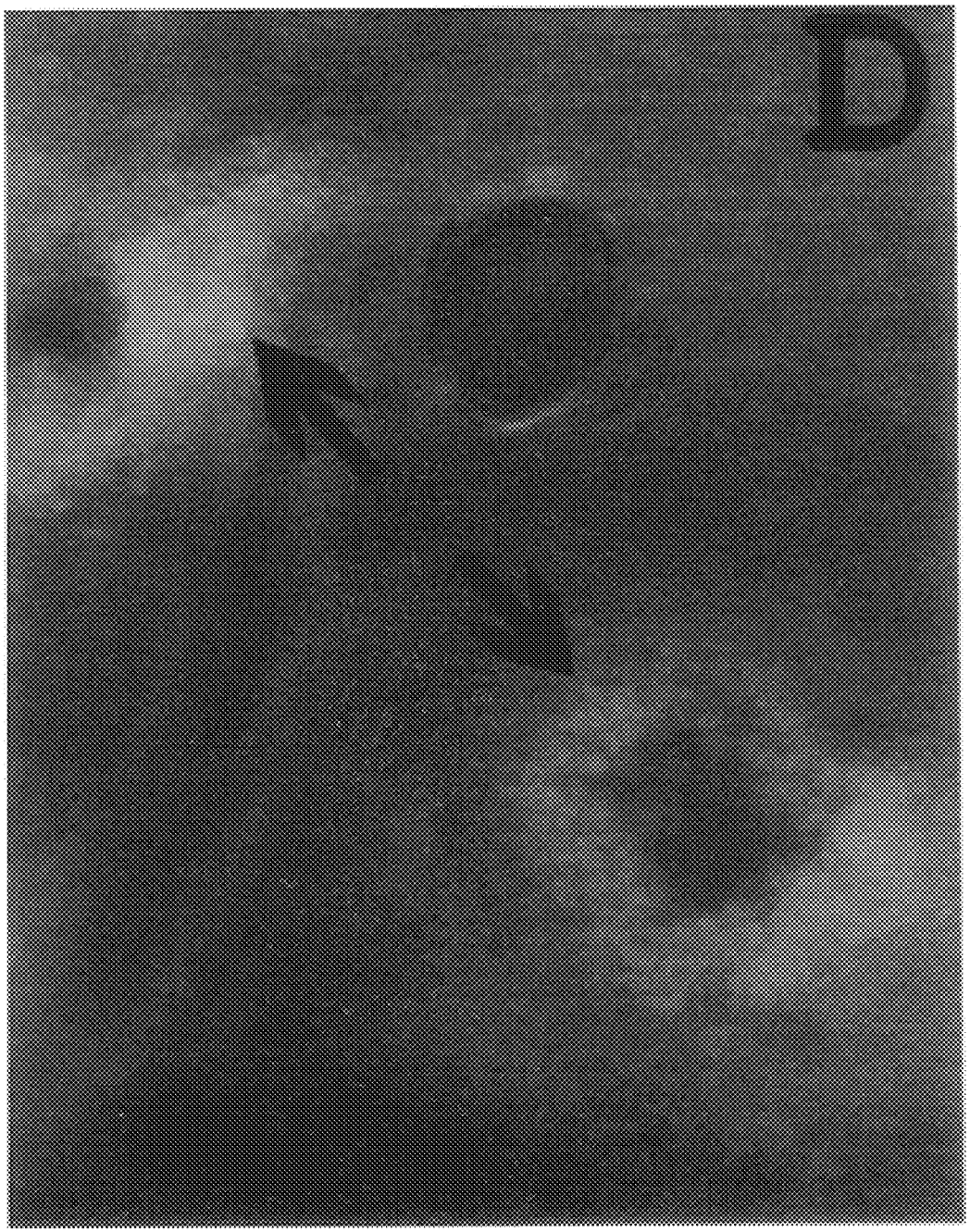
Figure 18A:
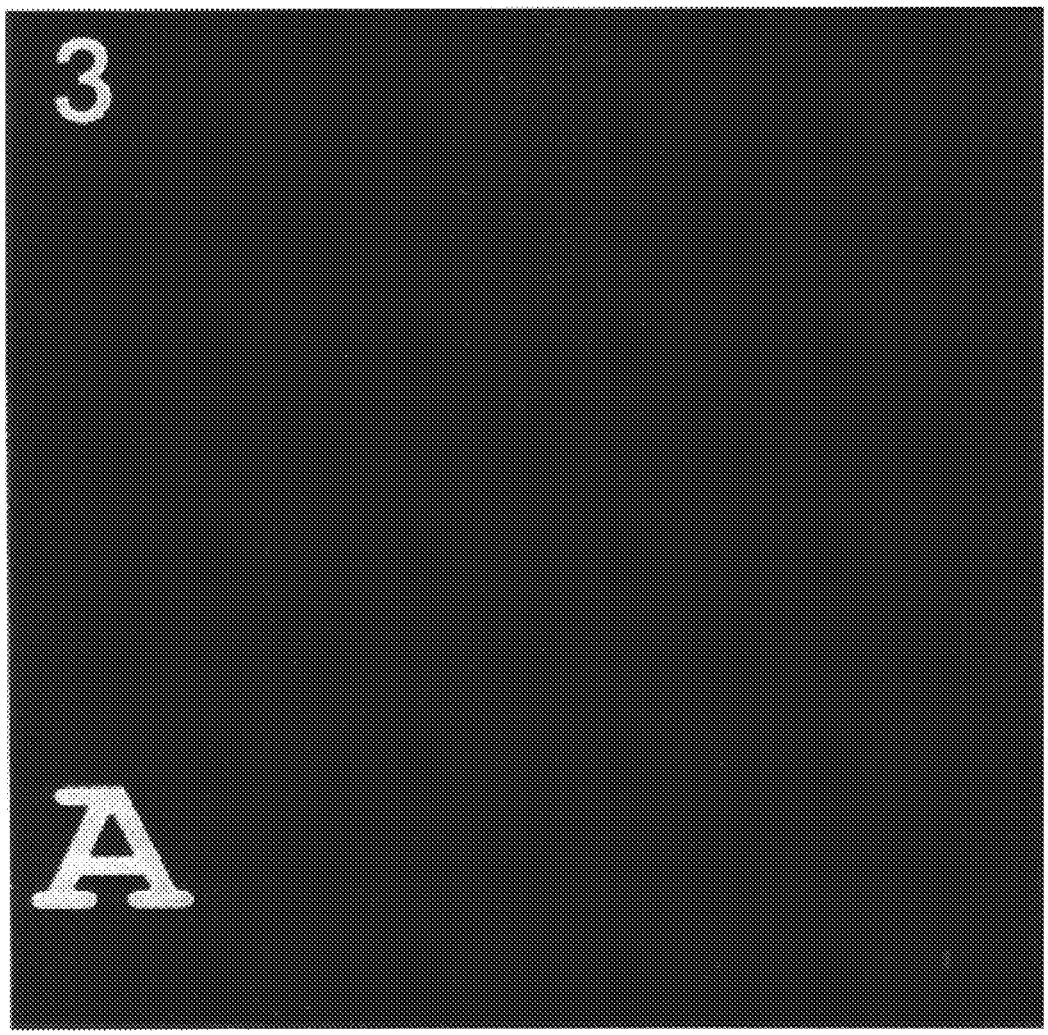
Figure 18B:
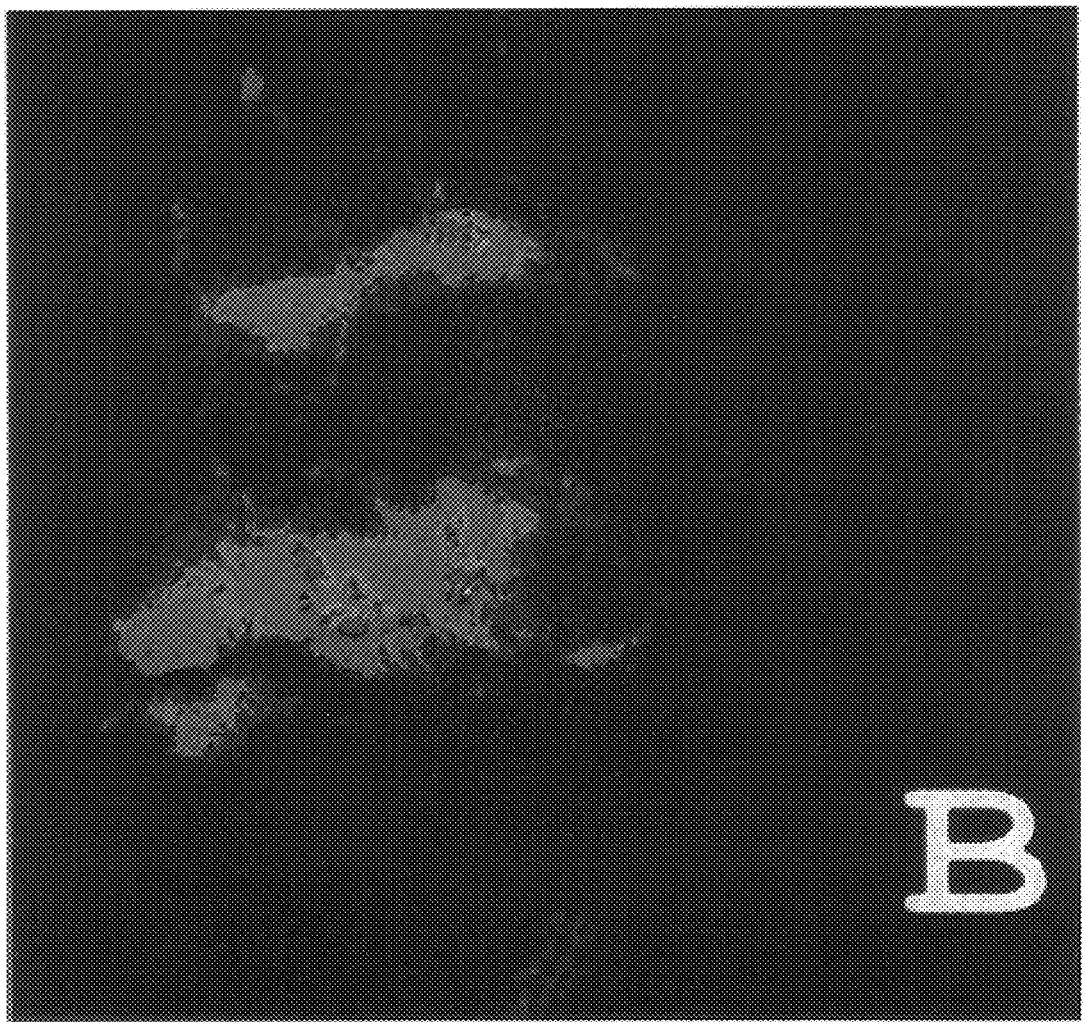
Figure 18C:
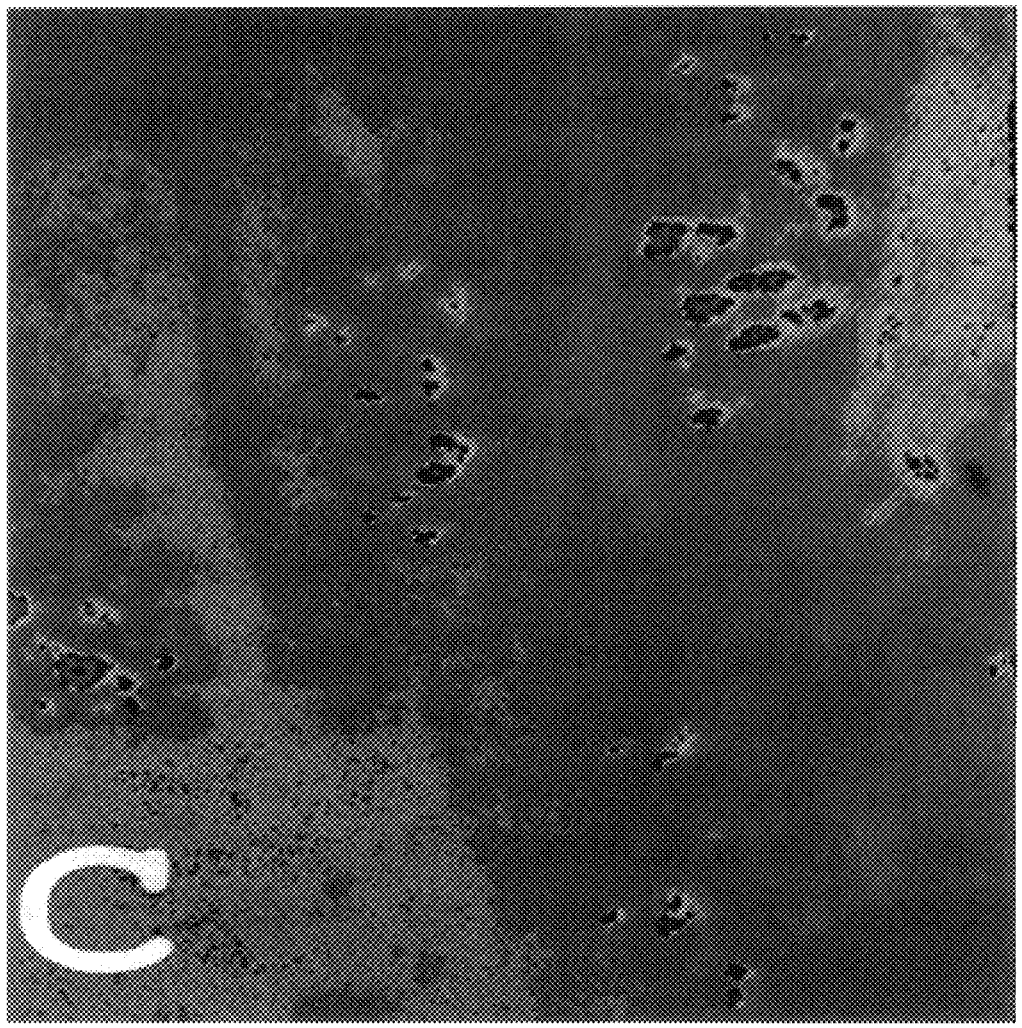
Figure 18D:
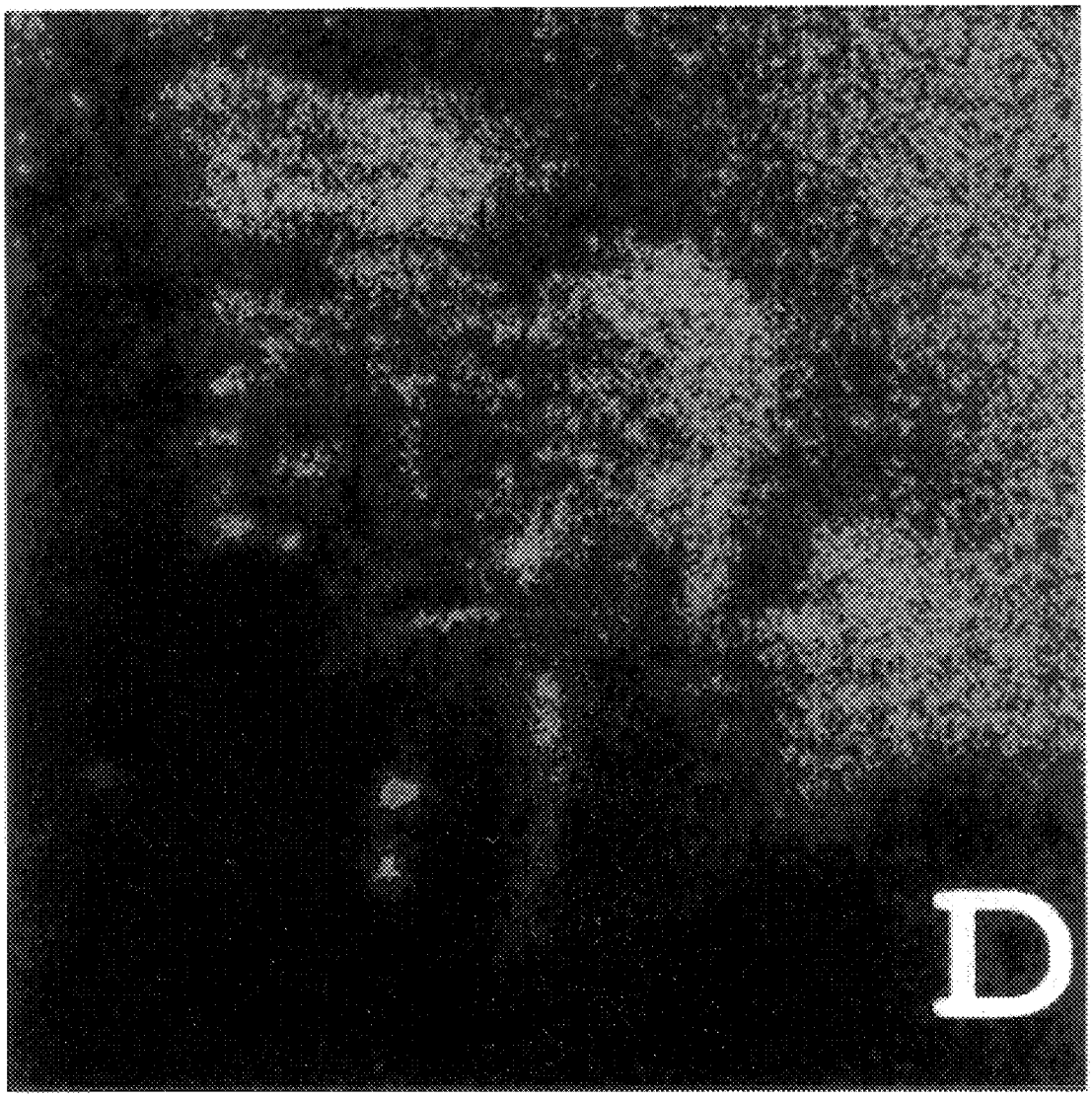

FIG. 15. shows H&E stained lung sections from mice treated with the lacZ vector.

FIGS. 16A–D Intracellular calcium stores in the intestines from rescued knockout mice. The intestines from cftr–/– (Panel A), in utero cftr-treated cftr–/– (Panel B), cftr +/– (Panel C), and in utero cftr-treated cftr+/– (Panel D) were cross sectioned and stained with Calcium Green' for intracellular calcium. All samples were examined by confocal microscopy. Magnification=100×

FIGS. 17A–D Intracellular calcium stores in the airways from rescued knockout mice. The airways from cftr+/– (Panel A), in utero cftr-treated cftr+/–(Panel B), cftr–/– (Panel C), and in utero cftr-treated cftr–/– (Panel D) were cross sectioned and stained with Calcium Green' for intracellular calcium. All samples were examined by confocal microscopy. Magnification=100×

FIGS. 18A–D. UTP receptors in the intestines from rescued knockout mice. The intestines from cftr–/– (Panel A), in utero cftr-treated cftr–/– (Panel B), cftr +/– (Panel C), and in utero cftr-treated cftr+/– (Panel D) were cross sectioned and stained with Rhodamine Green-UTP. AU samples were examined by confocal microscopy. Magnification=100×

Figure 19A:
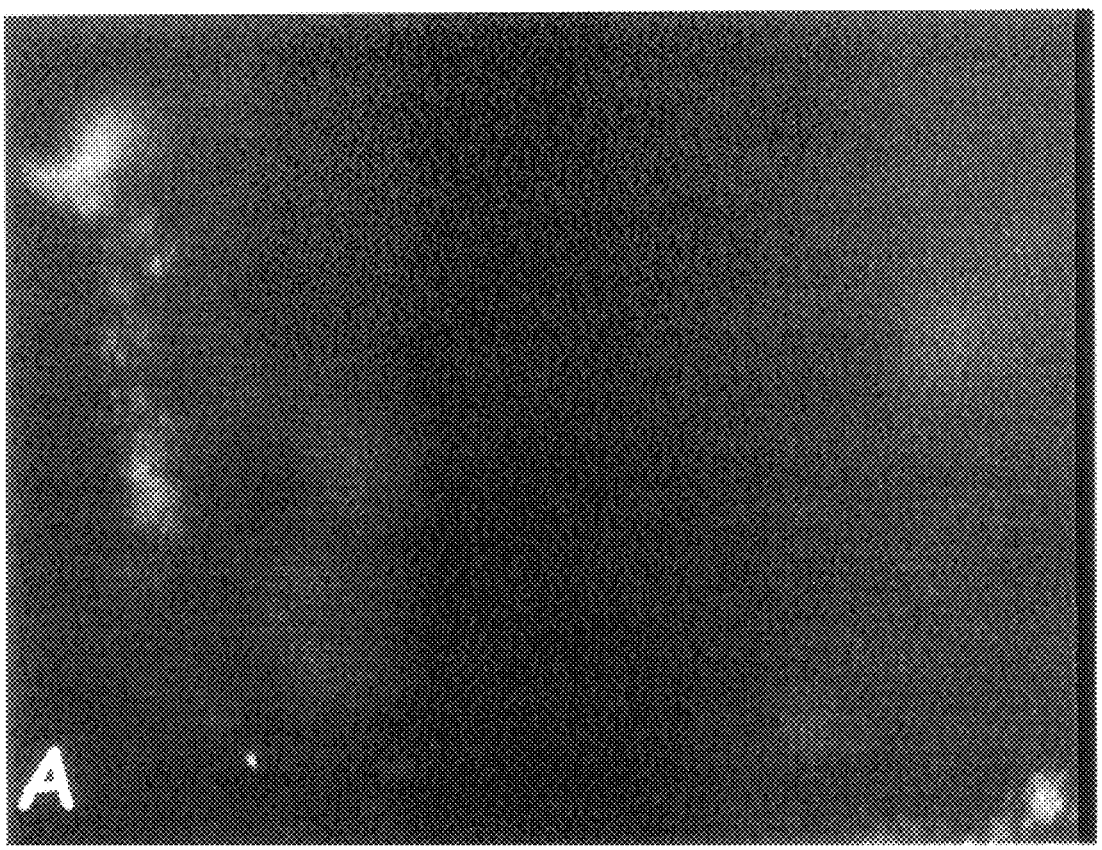
Figure 19B:
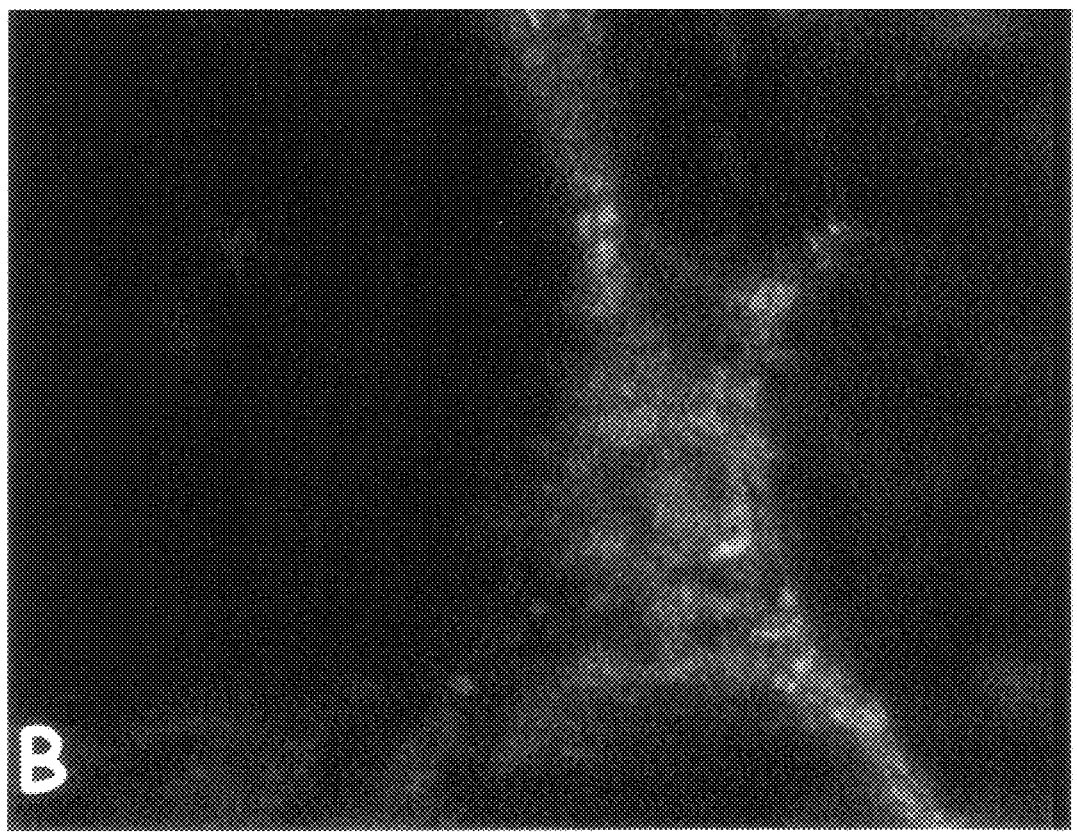

FIGS. 19A–B. Intracellular calcium stores in the intestines from knockout mice after in utero ATP rescue, shown in Panel A. UTP receptors in ATP-treated intestines, shown in Panel B.

DETAILED DESCRIPTION OF THE PREFERRED EMBODIMENTS

Introduction

The CFTR Gene and Gene Therapy

Unless provided directly, citations herein are provided in the section entitled "Incorporation by Reference", below. The Cystic Fibrosis Transmembrane Conductance Regulator (CFTR) gene was cloned without the subsequent knowledge of the structure and function of the protein (1). Since that time the function of the protein product of the CFTR gene (the "CFTR protein") was established as a cAMP regulated chloride channel. Considerable effort has focused on the correlation between specific mutations (of which there are over 400) and the phenotypic patterns of the Cystic Fibrosis (CF) disease. The goal of these efforts was to correlate the known structure and function of the protein with the clinical manifestations of the disease.

Many functions of the CFTR protein have been found that do not appear directly related to the disease. For example, CFTR protein has been shown to regulate other secretory channels (2), mediate vesicular trafficking (3), and affect glycosylation (4,5). The two nucleotide binding domains (NBD1 and 2) of the CFTR protein share structural homology with conserved sequences of G-proteins (6). CFTR mRNA and the CFTR protein show temporal and tissue specific expression during development (7,8,9,10,11). The protein is present early in the yolk sack, and is in the developing respiratory epithelium starting at seven weeks gestation. CFTR mRNA, as localized by in situ hybridization, is expressed throughout the lung epithelium in the first and second trimesters (10). Although there has been no CFTR mRNA detected in the fetal submucosal glands (8), the protein has been localized in the serous acini in the fetus (9).

Multiple organ systems are affected in CF disease. However, the most lethal pathology is the mucous plugging, chronic inflammation, and brohchiectasis that result in respiratory failure and cor pulmonale (12). Although thickened mucous secretions can be explained by defective secretion of lung liquid and hyperabsortion of sodium by the respiratory epitheluim, many of the symptoms of the disease cannot be explained by CFTR's chloride channel function alone. The association of CF with chronic pulmonary infections due to *Pseudomonas aeruginosa* as well as other organisms remains particularly puzzling (13,14,15,16).

Of the more than twenty clinical trials for targeting single-gene deficiencies that are approved by the NIH Recombinant DNA Advisory Committee (the RAC), sixteen are aimed at replacing the CFTR gene (17). Each of these protocols is utilizing adenoviral infections as the gene delivery construct. The consistent observation from the above-mentioned protocols and from other work in the field is that recombinant adenoviral constructs appear limited in both safety and efficacy due to host inflammatory responses and the transient expression the the recombinant gene. Many laboratories have shown that each of the above problems (inflammatory response and transient expression of the vector) were mediated by the immune response in the host (18). For example, when the vector was administered at low concentrations, the uptake and expression the transgene is inefficient. Higher concentrations, however, resulted in acute inflammatory responses and dose-dependent systemic reactions in the treated individuals (18,19,20). These trials showed the difficulty of judging successful therapy when the ultimate functions of the protein are unknown.

The transfer of genes to the developing fetus is attractive. Immune tolerance to a transgene may prolong expression. Several groups, including ourselves, have shown high-efficiency adenoviral-mediated transfer in the fetus. Sustained transgene expression was shown in fetal lung explants in culture (22) and in neonatal animals (23). We reported sustained expression, with no inflammatory response, of an adenoviral-mediated in-utero transfer of the LacZ reporter gene into the developing pulmonary epithelium (24).

In utero gene transfer adds an additional dimension to gene therapy; it allows the possibility of including developmental programming into the experiments. Thus, knowledge of normal cellular development, and in connection with the CFTR gene, lung development, is critical to the success of the experiments and understanding experimental results.

In early gestation the internal surface of the lung is structurally simple and an ideal target for somatic gene transfer. The transfer of genes into the growing lung would be particularly useful in the prenatal correction of a variety of genetic defects, such as cystic fibrosis, which has devastating pulmonary complications. In addition, in utero gene therapy has the potential to immunotolerize the individual, and thereby avoid the immune reactions now seen with the current generation of many gene constructs, such as adenoviral vectors, in current use in gene therapy.

As was mentioned previously, we have surprisingly discovered that it is possible to conduct gene transfer in a prenatal infant to correct gene defects in the infant prior to the birth of the infant through direct exposure of the infant to a gene within the amniotic fluid surrounding the infant in utero. We are aware of certain work by others that has been published within the last year where the general process of delivering a gene into the amniotic fluid surrounding an infant mammal has been suggested and attempted. However, the prior work has failed because, contrary to the expected immunotolerance of prenatal infants, the delivered genes has been inactivated through moderate to severe immune responses in the infants. The extent of the immune response has ranged from simple inactivation of the gene following a short lived expression of the gene in the infant to death of the infant.

In contrast, in our studies, we have attained exceptionally high levels of expression of genes in targeted tissues for extended periods of time without any evidence of an immune response against the delivered gene. We expect that certain factors contributed to our success where others have failed. Such factors include (i) the careful selection of the time of delivery of the gene into the amniotic fluid surrounding the infant so as to correspond to the optimum growth phase of cells in the tissue sought to be targeted as well as correspond to a time when the targeted tissue will achieve contact with the amniotic fluid containing the gene, (ii) the careful selection the anesthesia used, if any, (iii) the careful selection of the site within the uterus where the gene is delivered in the amniotic fluid to allow ample quantities of the gene to reach the particular tissue of interest, and (iv) the careful control of the dose of the gene delivered.

Our work indicates that while each of these factors contribute to the successful introduction of a gene to a targeted tissue, no single factor is necessarily more significant than another. Rather, each of the factors are important to consider in the design and optimization of delivery of any particular gene in any particular targeted tissue of an infant. Such considerations will be elaborated in more detail below and it will be appreciated that those of ordinary skill in the art will be capable of modifying particular gene and target strategies without undue experimentation.

Our work has revolved, in particular, around the delivery of foreign genes into the lungs of prenatal infant mammals. This experimental bias is based on our interest in disease of the lung, such as cystic fibrosis (CF). However, as mentioned above, it will be appreciated that those of ordinary skill in the art will be able to apply the teachings of our fundamental work to the delivery of numerous genes to numerous targeted tissues in prenatal infants without undue experimentation. We will, however, begin with a discussion of delivery of genes to the lungs of an infant mammal in utero.

Mammalian Lung Development

To assist with an understanding of the present invention, it is beneficial to understand mammalian lung development. As will be appreciated, lung development in mammals follow relatively simple paths. The lungs begin as an invagination from the ventral esophagus. The large conducting airways develop first from the endoderm of the diverticulum. Ten Have-Opbroek "The development of the lung in mammals: An analysis of concepts and findings" Am. J. Anat. 162:201–219 (1981), the disclosure of which is hereby incorporated by reference. The airways continue to branch distally, and the lung can be followed developmentally by counting generations of branches. Hislop et al. "Development of the acinus in the human lung" Thorax 2 9:90–94 (1974), the disclosure of which is hereby incorporated by reference. The early epithelial cells lining the airways are columnar and are called primitive fetal cells because they appear to be pleuripotential. Adamson *Development of Lung Structure* in Crystal et al. "The Lung: Specific Foundations" pp. 663–666 (Raven Press, Ltd., New York (1991)), the disclosure of which is hereby incorporated by reference. After 20 weeks gestation in the human infant (as compared to 14 days in the rodent), the primitive airways are lined by a combination of columnar and cuboidal multipotential stem cells. The columnar cells are the precursors for the secretory and ciliated epithelium (conducting airways), and the cuboidal cells are the precursors of the respiratory epithelium. Ten Have-Opbroek "The development of the lung in mammals: An analysis of concepts and findings" Am. J. Anat. 1 6 2:201–219 (1981). Like growth, epithelial cell differentiation occurs first in the trachea and then moves distally. Rapid proliferation occurs distally at the branching tips and differentiation occurs after proliferation has diminished. Ten Have-Opbroek "The development of the lung in mammals: An analysis of concepts and findings" Am. J. Anat. 1 6 2:201–219 (1981); Kaufman et al. "Cell proliferation in the mammalian lung" *Int. Rev. of Exp Path.* 1 2:131–191 (1980), the disclosure of which is hereby incorporated by reference.

Rat lung development is relatively immature when compared to humans. At birth, their lungs are in a terminal sac stage that is comparable to that of a 28 week gestation human. Rats do not develop alveoli until five days after birth. Ten Have-Opbroek "The development of the lung in mammals: An analysis of concepts and findings" Am. J. Anat. 1 6 2:201–219 (1981). Like growth, epithelial cell differentiation occurs first in the trachea and then moves distally. Rapid proliferation occurs distally at the branching tips and differentiation occurs after proliferation has diminished. Ten Have-Opbroek "The development of the lung in mammals: An analysis of concepts and findings" Am. J. Anat. 1 6 2:201–219 (1981); Kaufman et al. "Cell proliferation in the mammalian lung" *Int. Rev. of Exp. Path.* 1 2:131–191 (1980), the disclosure of which is hereby incorporated by reference.

Rat lung development is relatively immature when compared to humans. At birth, their lungs are in a terminal sac stage that is comparable to that of a 28 week gestation human. Rats do not develop alveoli until five days after birth. Ten Have-Opbroek "The development of the lung in mammals: An analysis of concepts and findings" Am. J. Anat. 1 6 2:201–219 (1981). Given our data obtained on fetal breathing movements in the rat, we determined that 16–17 days after gestation was an appropriate time for infection of the lungs. In addition, the lungs at that stage in development possess a largely undifferentiated columnar epithelium. As such, rapid growth is still occurring and the epithelial cell population doubles from 20% to 40% of all cells in the rat lung between 17 days and 20 days gestation. Adamson et al. "Sex related differences in cellular composition and surfactant synthesis of developing fetal rat lungs" *Am. Re. Respir. Dis.* 1 2 9:130–134 (1984), the disclosure of which is hereby incorporated by reference.

In the developing airways, CFTR distribution follows the cephalocaudal pattern of maturation and differentiation of the epithelial cells (9). CFTR protein and mRNA are not polarized to one domain of the epithelial cells in the more immature lungs. During the terminal saccular phase of development CFTR mRNA and protein shifts to the more apical distribution of the ciliated cells. This distribution bears similarity to that seen in the adult lung (7,9). Differentiation of the airways correlates with CFTR expression and becomes confined to the differentiated bronchiolar epithelium, the presumed site for cAMP-mediated chloride secretion.

Summary of Experimental Results

Previously, we infected rat fetus at 16–17 days gestation targeting the undifferentiated multipotential stem cells of the lung epithelium with a replication defective vector encoding the LacZ gene (24). We found that LacZ expression was maintained in the epithelium during a time when the lung volume increased approximately 20-fold, alveolarization occurred, and the epithelial cells differentiated. The animals were injected at a gestational age when their major air passages were formed as blind tubules lined by columnar and cuboidal epithelium. β-galactosidase was expressed in fully differentiated cells. We have now demonstrated that recombinant infection of multipotential stem cells maintains expression throughout differentiation. Further, we have now demonstrated the feasibility of in utero gene transfer of the CFTR gene to mammalian lung and other tissues. We have now studied the function of rat lungs in animals that were subjected to in utero gene transfer of the CFTR gene through the use of histochemical methods. In connection therewith, we have studied the resistance of rat lung tissues, genetically modified in accordance with the present invention, to bacterial infection. We have demonstrated that cells in the in utero gene therapeutically modified lungs are secretory and producing glycoconjugates and lipids. Using an intrapulmonary *Pseudomonas aeruginosa* challenge we have demonstrated that the parenchyma modified by hCFTR and its secreted products are involved in a primary line of host defense to bacterial infection in the lung.

SUMMARY OF EXPERIMENTAL EXAMPLES

In utero delivery and subsequent over expression of CFTR at the same gestational age in Sprague-Dawley rats resulted in permanent phenotypic and functional changes in the lung and intestinal epithelium. These animals were shown to have enhanced resistance to lung bacterial infection (Pseudomonas) over 90 days after the transgene was no longer detectable. Thus, permanent changes in the lung and intestines of the rat and the mouse were identified in the absence of continued expression of the transgene postnatally.

Transfer to the developing epithelium was accomplished by direct injection of a first generation, replication-defective adenovirus into individual amniotic sacs of rodent fetuses. At the time of infection, rodent lung and intestine development was comparable to that of a 10–20 week gestation human (Sekhon and Larson 1995). The major airways had formed allowing the virus to target multipotential columnar and cuboidal stem cells. Further differentiation and growth occurred after the infection. During this period of development, endogenous CFTR is highly expressed in these cell types. Columnar cells are the precursors of the secretory and ciliated epithelium of the conducting airways and cuboidal cells are the precursors of the respiratory epithelium (Ten Have-Opbroek, 1981). Differentiation of the alveolar epithelium to surfactant-producing type II cells started 3–4 days following infection. The alveoli in these lungs do not develop until ten days after infection (five days after birth).

CFTR expression, however, is not required to ameliorate of CFTR deficiencies in utero with amelioration continuing beyond birth of the treated subject. Amelioration of CFTR deficiency without cftr gene expression is shown by further experiments demonstrating the effectiveness of ATP in ameliorating the deficiencies in cftr−/− mice. The mice that were used are not capable of expressing cftr, even in a defective form. Thus, the amelioration of CFTR deficiency that we have observed following in utero treatment with ATP cannot be due to CFTR expression. Instead, the amelioration is due to activation of CFTR-sparing functions within the subject. Mechanisms of CFTR-sparing include, but are not limited to, interaction of ATP with purinergic receptors. ATP interaction is shown by restoration of UTP binding purinergic receptors and by the changes in Ca++ localization that we have observed in ATP-treated animals.

Long-lasting amelioration of in utero CFTR deficiency by the widely different mechanisms that we have employed indicates that any method to temporarily ameliorate CFTR deficiency, is likely to be useful when applied to in utero therapy. Thus, one skilled in the art would be able to successfully adapt any method of temporary CFTR amelioration to in utero therapy of a mammal in need of long-lasting amelioration with reasonable expectation of success and without undue experimentation.

In the present invention, the characterization of lungs and intestines from cftr−/− mice is used to identify changes in cell structure and function resulting from transient expression of the cftr gene in utero. These in utero cftr-dependent alterations demonstrate this gene's essential role in the differentiation of secretory cells. Evidence is presented to show that gene dosage of cftr is directly related to normal production of mucus and lung function.

The novel in utero therapeutic methods and results described herein are applicable to a wide range of organisms that have a deficiency in CFTR. These organisms include, but are not limited to, mammals such as mice, rats, other rodents, sheep, cows, horses, non-human primates, and humans. Diverse animal models exist and sufficient knowledge of each of these models allows predictable adjustment of technology developed with one or more mammalian models to other mammalian models, without undue experimentation. We have already noted herein, for example, that mice have alternative ion channels that modify the effect of CFTR deficiency in a way that differs predictably from the human model. Thus, with the present knowledge of interspecies differences, the technology that we have developed using the mouse model can be transferred and adjusted to another mammal by one skilled in the art, without undue experimentation. A skilled worker can accomplish such an adjustment by considering the known interspecies differences, including, but not limited to, the cited example of knowledge of the type and tissue distribution of ion channels within the instant species.

Monitoring Therapeutic Effectiveness

Moreover, our technology also includes novel means to monitor the effectiveness of the therapy. The capability to monitor therapeutic effectiveness is particularly useful during the process of adjusting for species differences.

Monitoring capabilities include a method of optimizing the dosage of a treatment for CFTR-deficiency by testing a sample of fetal tissue that has been affected by CFTR-deficiency from a fetus for hyperplasia, wherein if lung spaces that are occupied by gasses in a CFTR sufficient mammal are occupied by hyperplastic cells, the dosage is too high; and wherein if lung spaces occupied by gasses in a CFTR sufficient mammal are not occupied by hyperplastic cells, the dosage is not too high.

Another method of monitoring effectiveness of treatment for cftr-deficiency is to measure changes in intracellular Ca++ concentrations, wherein if the intracellular Ca++ level increases above that seen in the tissue from an untreated mammal, the treatment is effective; and if the intracellular Ca++ level does not increase, the treatment is ineffective.

Another method of monitoring effectiveness of treatment for CFTR-deficiency is to measure the amount of ligand that binds to purinergic receptors of the fetus, wherein if the amount of the bound ligand increases above that seen in an untreated animal, the treatment is effective; and if the amount of the bound ligand does not increase above that seen in the untreated animal, the treatment is ineffective.

The present invention also includes a kit for in utero treatment of a CFTR-deficient mammal comprising a container holding an agent, and instructions for administering the agent to the mammal in utero.

Gene Therapy of CFTR Deficient Mice: Experimental Procedures in Utero Gene Transfer.

Female heterozygous UNC knockout X C57bl/6 mouse 5th generation backcross mice were mated with either heterozygous and previously rescued homozygous knockout mice. At 15–16 days gestation animals were anesthetized as in Example (II)(C)(2) and the fetuses surgically exposed for injection. Virus ($10^9$ particles/ml of amniotic fluid) was injected into the amniotic fluid. Normal delivery of the animals was allowed to take place.

In Utero ATP Treatment

Female heterozygous UNC knockout X C57bl/6 mouse 5th generation backcross mice were mated with either heterozygous and previously rescued homozygous knockout mice. At 15–16 days gestation animals were anesthetized as in Example (II)(C)(2) and the fetuses surgically exposed for injection. 20 ul of a 20 mM ATP in sterile physiological saline was injected into the amniotic fluid. Normal delivery of the animals was allowed to take place.

Viruses

Virus preparations were grown in S 49 cells and purified by centrifugation to equlibrium in CsCl. Viruses used were Ad5.CMVlacZ, an adenovirus recombinant carrying the lacZ gene with a cytomegalovirus promotor, and Av1CF2 (Mittereder, Yei et al. 1994; Yei, Mittereder et al. 1994; Yei, Mittereder et al. 1994; Wilmott, Amin et al. 1996; generously provided by Genetic Therapy Inc., Gaithersburg, Md.), an adenovirus containing the human cftr gene with a *Rous sarcoma* virus promotor.

Histologic Examination

All tissues were fixed in paraformaldehyde for 12–18 hours and embedded in paraffin for thin sectioning. Alcian blue and periodic base Schiff stains were performed as described in Everson Pearse (1985). Lung sections were stained with SNA (*Sambicus nigra;* elderberr bark) lectin conjugated to biotin (obtained from E-Y Laboratories) and developed by the method of Castells et al. (1991).

Confocal Maicroscopic Examination of Tissues

All tissues were sectioned and washed in phosphate buffered saline. Stock solutions (1 mM) of stains obtained from Molecular Probes were used. Two microliters/ml of either CaGreen-AM. (Molecular Probes) or Rhodamine green-UTP (Molecular Probes) was added to the tissue, then incubated for 1–2 hrs All samples were examined on a Noran Odyssey CLSM with a Nikon Diaphot inverted microscope. The software used for the imaging was Noran's Intervision running on a SGI Indy workstation.

Electron Microscopic Examination of Tissues.

Isolated lungs were dissected and immersion fixed with gentle agitation in 100 ml of 0.1M sodium cacodylate buffered 2.5% glutaraldehyde at ambient temperature. Tissue slices were further fixed overnight in fresh fixative, then rinsed three times for 30 min each in chilled 0.1 M cacodylate buffer.

Washed tissue blocks were cut into 1 mm cubes and post-fixed in 1.0% osmium tetroxide/0.1M cacodylate buffer, en bloc stained using 0.5% aqueous uranyl acetate, dehydrated in acetone, and infiltrated and embedded in Polybed 812 (Polysciences). Thin sections were cut on a Reichert-Jung Ultracut E ultramicrotome equipped with a diamond knife (Diatome) and collected on 150 slotted mesh copper grids, then post-stained with lead citrate. Sections were examined in a JEOL 1210 transmission electron microscope (Japanese Electron Optics Laboratory) at 60 kV. Images were recorded on Kodak 4489 EM film.

Observations Related to cftr Deficient Mice

EXAMPLE 1

Rescue from the Lethal CF Phenotype by in Utero is Gene Therapy

The partially inbred strain of the heterozygotic cftrm1Unc129×C57Bl/6 knockout mouse (5th generation backcross) were mated. Progeny were treated in utero at 15–16 days gestation with either Av1CF2(containing human cftr: provided by Gene Therapy Inc., Gaithersburg, Md.) or Ad5.CMVlacZ (expressing beta-galactosidase,) as control. The treated animals were also compared to untreated (no surgery) animals. The fetuses were treated at a mouse developmental stage that is comparable to 10–20 week human fetal development. Treatment at this stage results in optimal uptake of the virus and transgene expression in both the rat and mouse fetus (See Example (II) (C) (I)). Twenty-one animals in 8 independent experiments over 12 months were rescued by in utero intervention with cftr. Rescued cftr−/− mice now have several progeny who themselves have been rescued in the same way.

No functioning cAMP regulated chloride channels are present in the rescued mice. Thus, continuous function of CFTR is not required for reversal of the obstructive intestine phenotype of the knockout mice.

EXAMPLE 2

Reversal of Abnormal Intestine Morphology in the cftr−/− Mouse.

Intestines from treated cftr−/− and untreated cftr+/− mice older than 75 days, were fixed, embedded in paraffin, and examined following Alcian Blue-PAS staining.

Intestines from the rescued knockout mice did not exhibit the pathology previously described for untreated knockout mice (Snouwaert and Brigman, et al., 1992). Intestines from the cftr+/− mice (FIG. 11, Panel A and C) and those of in utero cftr-treated cftr−/− mice (Panel B and D) showed similar intestine histology. No goblet cell hypertrophy, no crypt dilitation, and a normal amount of PAS positive secretions were seen in the cftr-treated cftr−/− mice. Thus, correction of the dysfunctional secretory cell pathology by in utero cftr-treatment rescues cftr− mice from the lethal CF phenotype, and this occurs with only a temporary replacement of the cAMP-dependent chloride channel.

EXAMPLE 3

Mucous Secretions in the Lung After in Utero Rescue

Changes in secretory function in the lungs of rescued mice were also attributable to the rescue process. Lectins were used to evaluate changes in the mucous of tissue from adult mice long after transgene expression had ceased. Four classes of mice were examined: knockout untreated, knockout treated, heterozygote and heterozygote treated lungs Table 4.

TABLE 4

Lectin staining of lung sections from normal and in utero cftr-treated cftr−/− and cftr+/−

| Lectin | Carbohydrate Specificity | Specificity | Result |
| --- | --- | --- | --- |
| SNA (EBL) | [](2,6)sialic acid | Affinity to Pseudomonas in mucus | Increased surface staining in knockout and altered cellular location in rescued knockout |
| UEA | Fucose | Possibly increased in CF[2] | Increased surface staining in knockout and altered cellular location in rescued knockout |
| MAA | [](2,3)sialic acid | Affinity to Pseudomonas in mucus[1] | No differences in cellular location; possible increase in surface staining in untreated knockout |
| MPA | N-Acetylgalactosamine | Clara and Type II cell differentiation | No differences observed |
| RCA | Lactose and Galactose | Type I cell differentiation | No differences observed |
| WGA | N-Acetylglucosa | Goblet cells[3] | No differences |

[1]Ramphal et al, 1989; Plotkowski et al, 1993; Lambin et al, 1991,
[2]Carnoy et al, 1993,
[3]Mazzuca et al, 1982

Figure 12A:
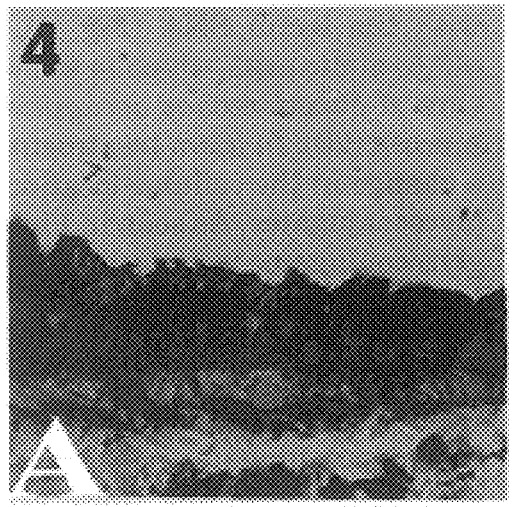
Figure 12B:
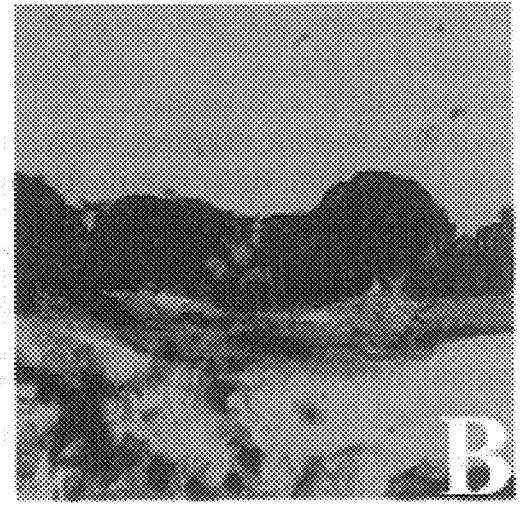
Figure 12:
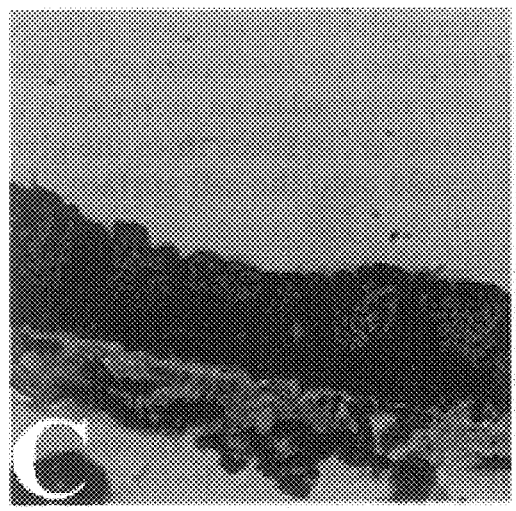
Figure 12D:

Data presented in FIG. 12 compares the airways of the same four classes of mice: A) knockout untreated, B)

heterozygous untreated (control), C) knockout treated and D) heterozygous treated mice. Staining with the lectin SNA (EBL) exemplifies changes in the secretory cells of the airway epithelium. SNA is specific for (2,6) sialic acid and is known to mediate adherence of *Pseudomonas aeruginosa* to the respiratory mucosa (Plotkowski, Bajolet-Laudinat et al. 1993). In utero treatment with cftr resulted in a change in the cellular location of SNA stain. As seen in panel A, SNA is localized to the surface epithelium in the knockout untreated animals and is increased as compared to controls (panel B). The SNA stain is relocated into intracellular granules after in utero treatment with cftr. Cells containing these granules were present throughout the airways of the rescued cftr−/−lungs. This glycoconjugate also increased in heterozygotes that had been subjected to in utero cftr-treatment (Panel D).

A lectin specific for fucose, UEA, revealed similar changes Table 4. Lectins WGA, HPA, MPA and RCA, revealed no qualitative or quantitative differences between the experimental groups. RCA stained only the parenchyrna and very little in the airways, while WGA stained both the airway and lung parenchyma diffusely. MAA staining in the homozygous knockout animals increased slightly as compared to the other groups, but no changes in cellular location occurred.

EXAMPLE 4
Electron Microscopic Examination of Lungs

Fixed and stained lung tissue from the rescued (age 75 days to >1 year) and untreated (age 35–40 days) knockout mice were examined with an electron microscope. As shown in FIG. 13, significant differences were found between treated and untreated tissues. The ultrastructural features typical of Clara cells were evident in the small airways of untreated, cftr−/− mice. The Clara cells of untreated, cftr−/− mice contained distinctive secretory granules, a large amount of smooth endoplasmic reticulum and a small amount of rough endoplasmic reticulum in a basal location near the nucleus (Panel A). In place of typical Clara cells, rescued mice had Clara-like cells with a significant increase in vesicles, dilated smooth endoplasmic reticulum (Panel B), and no rough endoplasmic retciculum. We conclude that transitory exposure to cftr in utero altered development of the secretory cells in the lungs of the cftr−/− mice.

A singular adventitious observation that further distinguishes treated and untreated mice is shown in the electron micrograph of FIG. 13, Panel C. This micrograph shows intact immature vesicles at the site of a bacterial infection. Maturation (condensation is demonstrated by small dark vesicles near the apical surface) of the secretory granules has occurred. Intact immature vesicles in the airways may represent release either by exocytosis or by cell lysis. An alveolar macrophage is also present at site of infection and could have facilitated cell lysis (Panel C). Release of these vesicles was not observed in lungs from uninfected, rescued knockout mice

EXAMPLE 5
Dose-dependent Lethality of cftr in Utero.

The data presented in FIG. 11 and FIG. 12 are problematic. CF is characterized by an increase in mucus and an increase in secretory (goblet) cells. Likewise, expression of cftr in utero in the normal, heterozygous mice is characterized by an increase in SNA and UEA-positive secretory materials. Thus, the rescue process seems to actually mimic the well known CF syndrome. Thus, normal lung development may require expression of cftr over a narrow temporal and concentration range, while excessive, deficient or temporally misplaced expression may result in pathologic changes in lung tissue.

A negative effect of excessive CFTR expression is consistent with the survival statistics of the in utero cftr-treated mice. Many of the in utero cftr-treated newborns appeared cyanotic and died within two to three days following delivery. Respiratory insufficiency of some type was a potential cause of the high neonatal mortality rate in these cyanotic mice.

Deceased fetuses were collected and genotyped when they were not destroyed by their mothers. The mothers did destroy a large number, but thirty-four in utero cftr-treated animals lost during the first five days of life were genotyped. Seventy percent were cftr+/+. Only 9% were homozygous knockouts (cftr−/−) and the remaining 21% were heterozygotes. In contrast, of the control (Ad5.CMV lacZ-infected) mice that died during the perinatal period, only 23% were homozygous normal, 73% heterozygous, and 4% were homozygous knockouts.

Since consumed pups resulted in an incomplete data set, it was difficult to draw conclusions from these data alone. For completeness, we allowed the animals to survive well into to adulthood (>75 days of age) before examining the effects of perinatal death on the expected Mendelian ratio of the surviving populations.

The survivors did not conform to the population that would be expected from Mendelian genetics. Both untreated (no surgery) and control, lacZ-treated populations had a higher percentage of homozygous survivors than would be expected for a lethal autosomal recessive disorder (table 5). The expected Mendelian ratio in this population is 2:1 for heterozygote/wild type genotypes. A small decrease in heterozygote survival was reported in the outbred S489×mouse strain (Snouwaert and Brigman, et al. 1992). The partial inbreeding of the strain used in this study (5th generation backcross to C57B1/6) resulted in a homozygote wild type to heterozygote ratio of nearly 1:1. The surgical procedure did not significantly alter the proportions of heterozygous and homozygous normal populations.

TABLE 5

Adult survivors of heterozygote/heterozygote matings.

|  | −/− Survivors (%) | −/+ Survivors (%) | +/+ Survivors (%) |
| --- | --- | --- | --- |
| Untreated Mice | 0 | 57 (52%) | 52 (48%) |
| Control (lacZ) Mice | 0 | 7 (43%) | 9 (57%) |
| Expected Frequency | 0 | 67% | 33% |

Homozygous normals are over-represented in both untreated and control-treated populations relative to the expectation for a lethal autosomal recessive disorder. The Mendelian ratio expected in this population is 2:1. This decrease in heterozygote survival has been noted previously (Snouwaert, 1992). The untreated and treated populations were not significantly different from each other.

The population ratios of adult survivors (>75 days) following in utero treatment with cftr were compared to the expected Mendelian ratio of 1:2:1 (Table 6). The expected ratio of the surviving population would obtain if all of the knockout (cftr−/−) pups were rescued and there were no affects of cftr on mortality of the heterozygote and homozygote wild type population. Remarkably, only 8% of the surviving adult population was cftr+/+. The resultant ratio varied significantly from the expected ratio (p<0.001). Intrauterine treatment of fetuses with cftr resulted in a two-fold increase of surviving knockouts as compared to treated wild type genotypes. Given that expression of cftr was transient and there was no protein or mRNA expressed after birth (Larson, Morrow et al. 1997), the perinatal death of these animals suggested that the treatment led to structural defects in the fetuses that were not compatible with life. These results confirm the previous observation that most of the neonatal mortality occurred in the cftr-treated homozygous wild type population. Evidence for lethal structural defects caused by cftr-treatment of cftr+/+ animals is shown in FIG. 16 and FIG. 18. These figures show H&E stained lung sections from cftr+/+ mice, either cftr-treated (FIG. 14) or treated with the lacZ vector (FIG. 15). The untreated mice show normal lung structure, including typical airways and alveoli. The treated mice exhibit hyperplasia with the alveoli and airways filled with hyperplastic clara cells. This structural abnormality is consistent with perinatal death and with symptoms of respiratory insufficiency displayed by the newborn animals.

The proportion of heterozygotes was also higher than the expected proportion of rescued homozygous knockout animals (Table 6). The absence of an expected portion of these animals suggested that some loss occurred prenatally and that intrauterine rescue was not perfect. Although we could not label individual fetuses in utero, a number of fetuses were identified by inspection during the injections as growth-retarded. These litters subsequently produced knockout (−/−) mice, confirmed by PCR analysis. The in utero cftr-treated knockout mice were smaller at weaning and remained so throughout adulthood.

EXAMPLE 6
Effect of Intrauterine cftr on Lung development in the Normal Mouse.

The poor survival and disproportionate number of neonatal deaths among in utero cftr-treated cftr+/+ animals suggested that the gene was causing detrimental changes. The transgene targets the intestine and the lung. Therefore, these organs could be affected by gene toxicity. As already discussed in connection to (FIG. 14 and FIG. 15, respiratory insufficiency of some type is the most likely explanation of the high neonatal mortality rate observed in the in utero cftr-treated, homozygous normal mice.

TABLE 6

Population ratios in adult survivors following in utero transfer of cftr.

|                   | −/− Survivors (%) | −/+ Survivors (%) | +/+ Survivors (%) |
|-------------------|-------------------|-------------------|-------------------|
| Treated (cftr) Mice | 11 (15%)        | 57 (77%)          | 6 (8%)            |
| Expected Frequency | 25%              | 50%               | 25%               |

Results were compared to expected frequencies of the expected Mendelian ratio of 1:2:1. Remarkably, only 8% of the surviving adult population was homozygous normal. This suggests that the developmental effects of CFTR overexpression are lethal. In addition to the eleven surviving knockout mice that are shown above, this laboratory has produced eight more adults that are the result of knockout/heterozygote breeding.

To test this hypothesis, animals homozygous for the normal cftr allele were bred. The fetuses were treated at 16 days gestation with either Ad5.CMVlacZ or Av1CF2. At birth, the lung and intestines were removed and weighed. Lung to total body weight and intestine to total body weight ratios were determined. Both the specific lung weights and lung to body weight ratios were significantly decreased in the in utero cftr-treated, cftr+/+ mice as compared to those treated with the lacZ gene (Table 7). In the intestines, however, no change was observed between the two groups.

TABLE 7

Effects of over expression of CFTR in homozygous (+/+) normal fetuses

|                   | Lung wt     | Lung wt/body wt | Intestine wt. | Intestine wt/body wt |
|-------------------|-------------|-----------------|---------------|----------------------|
| Control (lacZ) Mice | .026 + .004 | .020 + .003    | .036 + .003   | .029 + .010          |
| Treated (cftr) Mic | .021 + .003 | .018 + .002    | .042 + .004   | .035 + .009          |
| p value            | <.01        | <.05            | .21           | .32                  |

EXAMPLE 7
Altered Physiology of the Intestines Following in Utero cftr Gene Therapy.

Calcium plays an integral role in secretion. Because the studies presented thus far suggested that in utero cftr altered secretory cells and their function, intracellular calcium stores were evaluated. Calcium Green™, a flourescent stain for intracellular calcium, was applied to cross-sections of both control and in utero cftr-treated cftr−/− and cftr+/− mice. All samples were examined by confocal microscopy.

Knockout mouse intestines revealed little if any stores of intracellular Ca2+ (FIG. 16; Panel A). In contrast, the intestines from heterozygous animals showed extensive Ca2+ stores (Panel C). Cells of the of the villi did not stain in untreated cftr+/− mice, while those of the crypt strained intensely. In utero cftr-treatment of cftr−/− mice restored intracellular Ca2+ in cells of the crypt (Panel B). Importantly, the Ca2+-positive cells were clones rescued from the cell population, as shown by their focal distribution. In treated heterozygous animals (Panel D) the normal pattern of differentiation was disrupted, resulting in a loss of specificity for the crypt cells shown in the untreated, heterozygous intestines.

Such variation in intracellular calcium stores is surprising since others have indicated that Ca2+ does not have even a permissive role in the cyclic adenosine monophosphate-(cAMP)-mediated stimulation process (Kottra 1995). Moreover, it has been said that cAMP does not regulate intracellular calcium concentration in human tracheal epithelial cells (Davis, Silski et al. 1994).

EXAMPLE 8
Effect of in Utero cftr on Purinogenic Receptors in the Intestines

Multiple purinergic receptors and multiple signal transduction pathways are activated in different membrane domains of tracheal epithelia (Hwang, Schwiebert et al. 1996) (Devidas and Guggino 1997). Functional characterization of the P2 purinoceptor superfamily support a diverse functional role for ATP and related nucleotides in the regulation of tissue function (Williams 1996). To examine the possible role of these purinergic receptors, changes in UTP receptors in treated and normal intestines were examined using UTP labeled with fluorescent rhodamine green to stain sections of intestines.

Untreated, knockout mice showed little if any specific intestinal staining with the fluorescently labeled UTP (FIG. 18, Panel A). Intestinal villi of untreated heterozygous mice, however, bound the stain (Panel C). A marked decrease and/or absence of UTP receptors was evident in the untreated, knockout mouse. cftr rescue of knockout mice, however, restored the UTP receptors (Panel B). The purinogenic receptors were clonally distributed, similar to the intracellular Ca2+ restored to the crypt cells. Adenovirus mediated gene transfer to individual stem cells would produce this result. The disruption of normal cellular differentiation in treated heterozygous mice seen as changes in intracelluar Ca2+, was reprised with UTP receptors. UTP receptors in the normal heterozygote intestines are homogenously distributed throughout the intestines, not localized to the villi as in cftr-treated heterozygous mice (Panel D).

Blau and Baltimore (1991) suggested that an active control mechanism governs differentiation, resulting in the expression of specific genes through the dynamic interaction of regulator proteins at a given time. The rescue of the cftr knockout mouse by transient in utero cftr expression reported here and previously (Larson, Morrow et al. 1997) suggests the participation of CFTR at 15–16 days gestation in the developmental regulation of the intestine, the organ most affected in the knockout mouse model.

Cftr rescue corrected the regulation of secretion in the epithelium in both the lung and intestine, regardless of the phenotypic classification of the secretory cell type. The cells lining the airway begin to store glycoconjugate materials intracellularly. In the intestines, altered intracellular calcium stores and UTP receptors are clonally restored in the in utero cftr-treated, cftr-/- mice.

Intracellular Ca2+ is involved in maturation and packaging of glycoconjugates (Thorn 1996) and purinogenic receptors regulate mucous release (Conigrave and Jiang 1995). Thus, changes in the intestines and lungs of in utero cftr-treated cftr-/- mice are consistent with altered regulation of glycoconjugate secretions.

EXAMPLE 9
In Utero Treatment of Mice with ATP

In utero ATP-treatment improved the survival of cftr deficient mice, as shown in Table 8. the genotypic distribution of surviving mice matched the expected Mendelion genotypic ratio. This level of survival indicates that ATP treatment obliterates the selective disadvantage that is associated with cftr deficiency. Indeed, it indicates that after ATP treatment no progeny, regardless of genotype, have any selective advantage over any other progeny. In contrast, cftr-treated mice are under represented in both homozygous -/- and +/+ states, indicating that individuals with a heterozygous genotype have a selective advantage. Absence of selective advantage of any type among the ATP treated survivors strongly also suggests that ATP treatment is non-toxic, regardless of genotype.

TABLE 8

|  | +/+ Survivors | +/- Survivors | -/- Survivors |
| --- | --- | --- | --- |
| cftr Treated-Mice | 11 (15%) | 57 (77%) | 6 (8%) |
| ATP Treated Mice | 4 (25%) | 9 (56%) | 3 (19%) |
| Expected Frequency | 25% | 50% | 25% |

Mice were treated with either Adenovirus containing the cftr gene or with 20 ul of a 20 mM ATP in sterile physiological saline at 15–16 days gestation. Survival is defined as living greater than 60 days on regular lab chow and bedding.

EXAMPLE 10
Altered Physiology of the Intestines Following in Utero ATP Therapy Intracellular calcium stores were evaluated after in utero ATP rescue, as previously described.

Knockout mouse intestines revealed little if any stores of intracellular Ca2+ (FIG. 16; Panel A). In contrast, the intestines from heterozygous animals showed extensive Ca2+ stores (Panel C). Cells of the of the villi did not stain in untreated cftr+/- mice, while those of the crypt strained intensely. In utero ATP-treatment of cftr-/- mice restored intracellular Ca2+ in cells of the crypt (FIG. 19, Panel A) when examined at 65 days old. Importantly, the Ca2+-positive cells were clones rescued from the cell population, as shown by their focal distribution.

Such variation in intracellular calcium stores is surprising since others have indicated that Ca2+ does not have even a permissive role in the cyclic adenosine monophosphate-(cAMP)-mediated stimulation process (Kottra 1995). Moreover, it has been said that cAMP does not regulate intracellular calcium concentration in human tracheal epithelial cells (Davis, Silski et al. 1994).

EXAMPLE 11
Effect of in Utero ATP on Purinogenic Receptors in the Intestines Changes in UTP receptors in ATP-treated intestines were examined using UTP labeled with fluorescent rhodamine green to stain sections of intestines.

As previously discussed, untreated, knockout mice showed little if any specific intestinal staining with the fluorescently labeled UTP (FIG. 18, Panel A). Intestinal villi of untreated heterozygous mice, however, bound the stain (Panel C). ATP rescue of knockout mice, however, restored the UTP receptors FIG. 19, panel B, as seen in 65 day old mice. The purinogenic receptors were clonally distributed, similar to the cftr- rescued mice. Clonal distribution would be expected if the rescuing event comprised a cellular differentiation event.

Gene Transfer in Accordance with the Invention

Fetal Breathing

The unique strategy for gene delivery in accordance with one aspect of the present invention is further made possible through fetal breathing. That is, prenatal infant mammals "practice" breathing, in utero, thereby drawing in amniotic fluid from the uterus. Thus, we predicted that it would be possible to move a gene from the amniotic fluid into the developing lungs of the infant through the process of fetal breathing. Apparently, through instinct, an infant begins to fill its chest and expand its diaphragm and in the process drinks and breathes amniotic fluid. The fluid that is breathed into the developing lungs is the vehicle for delivering the gene into the lungs.

Most of our knowledge related to fetal breathing is provided by noninvasive means (i.e., ultrasound) in humans and large animals. Harding Fetal breathing movements in Crystal et al. "The Lung: Scientific Foundations" pp.663–666 (Raven Press, Ltd., New York (1991)), the disclosure of which is hereby incorporated by reference. We utilized a rat model in accordance with the present invention. There was limited knowledge about fetal breathing patterns in rats. Therefore, to determine the onset of fetal breathing movements in rats, we injected a vital dye (trypan blue 0.4%) into individual amniotic sacs, serially, from fourteen days gestation. Good uptake of the dye into the lungs was observed macroscopically at sixteen days gestation.

As mentioned, with larger mammals, such as humans, it is possible to monitor the onset of fetal breathing through noninvasive means, such as ultrasound. Thus, the onset of fetal breathing in larger mammals can be conveniently monitored and gene delivery into the amniotic fluid can be accomplished when fetal breathing is initiated.

Observations Related to Lung Delivery of Gene Constructs in Accordance with the Present invention When a gene construct is delivered into the amniotic fluid at a time where the airways are lined with pleuripotential stem cells, which developmental stage appears to coincide with the time that fetal breathing has been initiated, we observe significant expression of the gene in the bronchial epithelial cells of the infant lung. Although there are isolated cells in the periphery of the lungs, such as in the aveoli, maximum expression of the gene appears in the conducting airways and the proximal terminal bronchioles. This observation is consistent with a centripetal pattern of lung development, as discussed above, where the large conducting airways develop first from the endoderm of the diverticulum, Ten Have-Opbroek, supra, followed by continued distal branching of the airways, Hislop et al., supra.

Similarly, the pulmonary epithelium is undergoing a centripetal evolution, with epithelial cell differentiation occurring first in the trachea and then moving distally. Rapid proliferation occurs distally at the branching tips and differentiation occurs after proliferation has diminished. Ten Have-Opbroek, supra; Kaufman et al., supra.

Thus, the results demonstrate a strong correlation between cell cycle factors (including growth and differentiation) and ability of particular cells to uptake and express a gene.

Examples Related to Lung Delivery of Gene Constructs

Experimental

In connection with Examples (II)(C)(1) through (II)(C)(6), we performed the following general experiments:

We injected a replication-defective adenoviral vector into the amniotic fluid of rat pups on the 16th or 17th day of gestation. The adenoviral vector that we used contained the LacZ reporter gene and an *E. coli* β-galactosidase gene and is identified as the Ad5.CMVlacZ vector. The Ad5.CMVlacZ vector was obtained from Dr. Joseph Alcorn at University of Texas, Southwestern Medical School. The vector was prepared in accordance with Dr. Kolls procedures. See Kolls et al. "Prolonged and effective blockage of tumor necrosis factor activity through adenovirus-mediated gene transfer" *PNAS* 91:215–219 (1994), the disclosure of which is hereby incorporated by reference. The 16th or 17th day of gestation was chosen based on our experiment in Example (II)(C)(1). At days 16 and 17 of gestation, rat lungs are roughly equivalent in maturity to those of a 22-week human fetus as their airways are lined with undifferentiated multipotential stem cells. The pups showed high-level reporter gene expression in their airways a week following birth (13 days following infection). Amazingly, the expression was maintained during a time when the lung volume increased approximately 20-fold, alveolarization occurred, and the epithelial cells differentiated. The data, therefore, establishes gene targeting of undifferentiated fetal cells as an effective method of gene therapy.

EXAMPLE (II)(C)(1)
Determination of Fetal Breathing in Rats

As was discussed above, little was known about when in gestation fetal breathing in rats occurred. Therefore, to determine the onset of fetal breathing movements in rats, we injected a vital dye (trypan blue 0.4%) into individual amniotic sacs, serially, from fourteen days gestation. We observed good uptake of the dye into the lungs, through macroscopic evaluation, at days sixteen and seventeen gestation.

EXAMPLE (II)(C)(2)
Procedure for Delivering Gene Constructs in Utero

Timed-pregnant Sprague-Dawley rat litters were injected with a replication-defective adenoviral vector containing the lacZ reporter gene (Ad5.CMVlacZ). The rat model was chosen because of its well-defined lung development and short gestation. Using amniotic fluid volume as a standard, the vector was injected in doses ranging from $10^5$ through $10^8$ plaque forming units (PFU) $ml_{-1}$ amniotic fluid. Injection was accomplished into the individual amniotic sacs of each pup. One horn of the uterus was injected with the vector and the contralateral horn treated with a similar volume of saline.

Maternal anesthesia and analgesia, with their rapid transport across the placenta, are know to cause prolonged depression in the infant. See Moya et al. "Passage of drugs across the placenta" *Am. J. Obstet Gynecol.* 84:1778 (1962). This depression affects fetal movement and breathing patterns. Therefore, a short acting inhaled anesthesia was used.

The uterine horns were exposed and the amniotic sacs were injected with a fine gauge (32 gauge) needle at the anterior of the fetus, near the mouth. Such placement could be easily visualized via ultrasound in a human. A volume of no more than 10% of the known amniotic fluid volume, at the given point of gestation, was injected. This amount was well tolerated and there was little apparent leaking of amniotic fluid from the amniotic sac.

EXAMPLE (II)(C)(3)
Early Stage Examination of Fetuses and Mothers

In order to evaluate for toxicity, immune response, and infection of the mothers, certain litters of rat pups and mothers were killed and macroscopically evaluated. Upon our evaluation, the prenatal fetuses showed no evidence of increased fetal resorption rates, which indicated an absence of toxicity and immune system attack. Further evidence relating to the absence of an immune response was obtained through histologic examination of the fetal lungs. See FIGS. 1 and 2. The histologic evaluation showed no evidence of any inflammatory changes in the fetal lungs. Further, the mothers tolerated the procedure well, and histologic examination of their lungs showed no evidence of infection (data not shown).

EXAMPLE (II)(C)(4)
Post Delivery Examination of Fetus and Mother

We evaluated litters that were infected with (Ad5.CMVlacZ) in the entirety and allowed to deliver. There were no signs of any complications. Pups from the litters that were allowed to deliver were followed for up to one week after delivery (13 days after injection). The pups were healthy and appeared to be growing at a normal rate at the time they were killed.

EXAMPLE (II)(C)(5)
X-gal Staining and Histologic Evaluation of Lungs to Determine Expression In order to test for uptake and expression of Ad5.CMVlacZ vector in the lungs of the delivered pups, we stained the lungs with X-gal and examined sections of the tissues hisologically. X-gal staining was accomplished as follows:

Lungs were dissected and fixed in 4% paraformaldehyde in PBS for 30 min. After rinsing in PBS three times the lung tissues were incubated in 0.15% X-gal solution (5 mM Potassium Ferrocyanate, 5 mM potassium ferricyanate, 1 mM magnesium sulphate, 0.15% X-gal) overnight at room temperature. After embedding in ornithine carbamoly transferase (OCT), 8 μm thick sections were cut using a cryostat. The tissues were post-fixed in cold acetone and methanol, and counterstained with eosin.

We parallel processed the lungs from the virus-injected and saline-injected control animals for β-galactosidase expressing cells. The results from the immunohistochemistry would enable us to more accurately determine where, and in what cells the gene was taken up in and expressed most efficiently.

To this end, individual cells expressing the β-galactosidase gene were localized by immunohistochemistry with an antibody directed to *E. coli* β-galactosidase antibody (5 Prime—3 Prime, Inc., Boulder, Colo.). Indirect immunoperoxidase staining was accomplished using Vectastain ABC method (Vector Laboratories, Burlingame, Calif.) and developed with 3-amino-9-ethyl-carbazole (ABC) and counterstained with haematoxylon.

The individual cells expressing the enzyme could be identified by a red precipitate in their cytoplasm (FIG. 2*b*). Although there were isolated cells expressing β-galactosidase in the periphery of the infected lungs (alveoli), the maximal expression was in the conductiong airways and the proximal terminal bronchioles (FIGS. 1 and 2). Such data is consistent with a centripetal pattern of normal lung growth as discussed above. The animals were injected at a gestational age when their major air passages are formed but are blind tubules lined by columnar or cuboidal epithelium. After injection, extra generations of respiratory bronchioles or alveolar ducts arose from these always by centripetal growth. Consistent with normal development, the concentration of cells expressing β-galactosidase was highest in the conducting airways of the lung.

β-Galactosidase was expressed in fully differentiated cells of the infected rat lungs. At the time of infection, the respiratory portion of the epithelium was lined by a cuboidal precursor to the alveolar type I and II epithelium cells. Differentiation of the alveolar epithelium to surfactant-producing type II cells occurred at 20 days gestation, and cell kinetic studies show that the alveolar type I cells are derived from alveolar type II cells. The alveoli in the lungs of the pups did not develop until 11 days after infection (five days after birth). Compared with that of the controls, the histology of the alveoli was entirely normal in the treated pups.

The following experiments relate to the delivery of the CFTR gene to the lungs of the rats in accordance with the present invention. The CFTR gene is believed to be the gene that is defective in patients having CF. Current clinical trials in gene therapy for CF are being conducted in adults. In connection with those trials, it has been reported that immunologic responses limit the duration of the viral-mediated gene expression. McCray et al. "Adebivurak-mediated gene transfer to fetal pulmonare epithelia in vitro and in vivo" *J. Clin. Invst.* 9 5:2620–2632 (1995), the disclosure of which is hereby incorporated by reference. Through supplying the CFTR gene, in accordance with the present invention, it is expected that CF can be treated and, moreover, the immunologic response in connection with the treatment of adults can be avoided.

In connection with Examples (II)(C)(7) through (II)(C)(11), we performed the following general experiments:

We injected a replication-defective adenoviral vector into the amniotic fluid of rat pups on the 16th or 17th day of gestation. The adenoviral vector that we used contained the CFTR gene is identified as the Av1CF2 vector. The Av1CF2 vector was obtained from Genetic Therapy Inc., Gaithesberg, Md. The 16th or 17th day of gestation was chosen based on our experiment described above in connection with Example (II)(C)(1). At 16 and 17 days of gestation, rat lungs are roughly equivalent in maturity to those of a 22-week human fetus as their airways are lined with undifferentiated multipotential stem cells. The pups showed high-level CFTR protein expression in their airways and lungs more than a week following birth (i.e., more than 13 days following infection). Pups were continued to be followed for as long as 30 days post infection, and continued to show high levels of CFTR protein expression.

EXAMPLE (II)(C)(7)
Procedure for Delivering Gene Construct in Utero

Timed-pregnant Sprague-Dawley rat litters were injected with a replicaiton-defective adenoviral vector containing the CFTR gene (Av1CF2). The rat model was chosen because of its well-defined lung development and short gestation. Using amniotic fluid volume as a standard, the vector was injected in a dose of about $10^8$ through $10^9$ plaque forming units (PFU) $ml^{-1}$ amniotic fluid. Injection was accomplished into the individual amniotic sacs of each pup. All amniotic sacs containing pups were injected and mothers were allowed to deliver.

EXAMPLE (II)(C)(8)
Early Stage Examination of Fetuses and Mothers

In order to evaluate for toxicity, immune response, and infection of the mothers, certain litters of rat pups and mothers can be killed and macroscopically evaluated. Upon our evaluation, the prenatal fetuses showed we would expect to see no evidence of increased fetal resorption rates, which would indicate an absence of toxicity and immune system attack. Further evidence relating to the absence of an immune response could be obtained through histologic examination of the fetal lungs. The histologic evaluation would not be expected to show evidence of any inflammatory changes in the fetal lungs. Further, the mothers would be expected to tolerate the procedure well, and histologic examination of their lungs would show no evidence of infection.

EXAMPLE (II)(C)(9)
Post Delivery Examination of Fetus and Mother

We evaluated litters that were infected with (Ad5.CMVlacZ) in their entirety and allowed to deliver. There were no signs of any complications. Pups from the litters that were allowed to deliver were followed for up to 22 days after delivery (30 days after injection). The pups were healthy and appeared to be growing at a normal rate at the time they were killed.

EXAMPLE (II)(C)(10)
Evaluation of Lungs to Determine
Expression of CFTR Gene In order to test for uptake and expression of Av1CF2 vector in the lungs of the delivered pups, we confirmed protein expression by immunohistochemistry and visual inspection.

We parallel processed the lungs from the virus-injected and saline-injected control animals for CFTR expression through 22 days, as above. High-level CFTR expression was observed in the epithelium cells of the bronchi and bronchiolus.

Immunohistochemistry was conducted as follows. Frozen sections (8 μm thick) of lung tissue from infected pups were incubated overnight at 4 C. with a humanized mouse monoclonal antibody to the c-terminus of the CFTR protein. The antibody is available from Genzyme Corp. (Cambridge, Mass.) as mouse anti-human CFTR (c-terminus specific) monclonal antibody. Indirect immuno-peroxidase staining was accomplished using Vectastain ABC method (Vector Laboratories, Burlingame, Calif.) and developed with 3-amino-9-ethyl-carbazole (ABC) and counterstained with haematoxylon.

By way of comparison, the bronchial epithelium of a seven day old control pup that had been injected with normal saline at 16 days into the amniotic fluid showed minimal CFTR expression. In contrast, a seven day old pup infected with $10^9$ PFU $ml^{-1}$ amniotic fluid of Av1CF2 at 16 days gestation showed significant expression of CFTR in the lung epithelium. Pups infected at 16 days gestation showed high CFTR expression surrounding all of the large airways examined. Pups infected at 17 days gestation additionally showed peripheral tissue (aveolar expression). However, pups infected at either 16 or 17 showed substantially similar patterns of expression and each developed secretory cells in an apparently similar manner.

EXAMPLE (II)(C)(11)

Phenotypic Alteration of Stem Cells

In connection with our delivery of the CFTR gene through the in utero gene transfer methods of the present invention, we have surprisingly seen certain phenotypic alterations in progeny cells derived from stem cells infected with the virus in the pulmonary epithelium. Such cell appear to possess an altered function that may be related to the generation of glandular cells. In any case, such cells appear to be phenotypically altered based on their functional production of certain glycoproteins. The cells appear to possess secretory-type function. Whether such cells are glandular cells is not yet determined. Glycoconjugate production is evidenced by the fact that the cells stain positive in a Periodic Acid Stain (PAS) assay. See Theory and Practice of Histology, p. 172 (2d ed.). To conduct the PAS assay, we parallel processed the sectioned tissues discussed in Example (II)(C)(10).

Discussion of Experimental Results

From the time of injection to the time of evaluation, the lung volume in the pups injected with b-Gal increased approximately 20-fold. Depending on the day of gestation (16 or 17), pups infected with CFTR experienced lung volume increases of 20 to 50 fold. Despite this increase, the airways of the pups contained high concentrations of cells expressing b-galactosidase and/or the CFTR gene. The simple structure of the blind airways facilitated high-efficiency targeting, resulting in a large proportion of infected cells. Although the miotic index in the lung is almost 35% in the epithelium at day 17 of gestation in the rat, most of the proliferation occurs in the periphery. The already formed airways were slowly proliferating and differentiating at the time of infection. As the cells slowly divided and differentiated, adenoviral gene expression as continued through several generations. Early injection into the undifferentiated epithelium improved efficiency and provided good targeting.

Although one of the advantages adenovirus offered was the ability to target differentiated cells, previous reports indicate that the transfer efficiency was improved in neonates. Although the rapid period of growth in the lung affords the opportunity to use other vectors and gene constructs (for example, retroviral vectors, adeno-associated viral vectors, naked DNA, liposomes, DNA conjugates, and the like), the low frequency of adenoviral integration makes it a safe choice.

In accordance with the present invention, we have demonstrated that the fetus and newborn are immunotolerant, and this may explain the lack of inflammatory response that has been seen with other adenoviral infections. The ability to produce immune tolerance has a dear advantage, both from the perspective of safe delivery of genes, in utero, as well as the long term potential vaccine possibilities.

Further, the experimental results discussed in connection with Examples (II)(C)(10) and (11), provide certain indications that the replication defective adenoviral vector used in the experiments is actually becoming integrated into the cells, as opposed to simple expression in or from the cytoplasm of the cells. Such indication, however, has been disproven based on PCR studies that we have undertaken in which we have demonstrated that viral DNA expression and hCFTR gene plays a role in cellular differentiation, as is discussed in more detail below. Such results may vitiate the potential need to conduct follow-on therapies following delivery of infants.

The ability to target only the airway and not the alveolar epithelium offers a unique advantage in somatic gene therapy of the lung. The goals of somatic gene therapy are efficient and persistent transfer into a targeted tissue with minimal toxicity. The effects of cystic fibrosis (CF), the most common lethal autosomal disorder in the Caucasian population, are predominantly pulmonary. Replication-deficient recombinant adenovirus was used as a vehicle in the initial clinical trials both because of its ability to target slowly replicating and terminally differentiated cells and its natural tropism for the respiratory epithelium.

The initial results of clinical gene therapy trials in CF patients demonstrates that transfer into the epithelium is complicated by inflammatory cells, mucous, bacteria and other debris, as well as a mild to moderate inflammation in the airways. Also, attempts to target only the airways, and to avoid 'spillover' of the virus into the alveoli are complicated by the derangements of anatomy and frequent coughing in CF patients.

In addition, an interesting observation is that Roman et al. "Potential role of RGD binding integrins in mammalian lung branching morpogenesis" 112:551–558 (1991) (the disclosure of which is hereby incorporated by reference) suggest that RGD directed integrin receptors (i.e., VLA 5 and 3) are vital to normal mammalian airway function during early stages of lung development. The same integrins are viewed as facilitating the uptake of viral vectors, particularly adenoviral vectors. Such integrins are expected to be active at the very stages of lung development during which fetal breathing is commenced. Thus, the present invention, in connection with lung delivery and gene transfer represents a culmination of three important events: (i) the presence of pluripotential stem cells, (ii) that are presumably actively expressing RGD integrins, (iii) at a stage of development that the fetus is drawing amniotic fluid into the developing lungs.

The goal of one aspect of the present invention is to improve the delivery efficiency of genes to the pulmonary epithelium, at a time when the airways are simple, cells are mainly undifferentiated, and before alveoli are formed. Through the careful selection of vectors, it is expected that even better targeting and more sustained expression can be achieved through the use of the in utero gene therapy methods of the present invention.

CFTR Gene Therapy and Cellular Development/Differentiation

As discussed above, our method for the in utero adenoviral-mediated LacZ(Ad5.CMVLacZ) gene transfer to infect rat fetuses (19) was used with a replication-defective adenoviral vector containing the CFTR gene (av1CF2, Genetic Therapy, Inc.). See Experiment (II)(C)(7)-(11). In connection therewith, timed-pregnant Sprague-Dawley rat litters were injected with either Ad5.CMVLacZ or Av1CF2 vector on day 17 gestation. A final concentration of $10^8$ pfu·ml$^{-1}$ amniotic fluid was injected into the individual amniotic sacs and the mothers were allowed to deliver. As consistently seen in our previous experiments, all 34 injected pups delivered without complication and showed no increased resorption rate as compared to controls. All the pups were healthy at the time of sacrifice, and there was no growth difference between litters. We evaluated the pups at serial time points and compared their lungs to age-matched controls.

The pups were evaluated at one, five, twelve, and twenty-two days of age. These ages select and typify the various stages of lung development. At one day of age the lung development of the rat pup is in the saccular phase prior to alveolarization. Days five and twelve select the beginning and the end of peak alveolarization. At the time of infection, the respiratory portion of the epithelium was lined by a cuboidal precursor to the alveolar type I and II epithelial cells. Differentiation of the alveolar epithelium to surfactant-producing type II cells occurred at 20 days gestation. Cell kinetic studies show that the alveolar type I cells are derived from alveolar type II cells (29). The alveoli in these lungs did not develop until ten days after infection (five days after birth).

The histologic examination of the lungs from Av1CF2 infected pups revealed a population of cells not present in the control lungs (FIG. 3; arrows). The cells in the Av1CF2 treated lungs appeared to have increased adherent properties. The lungs did not have the characteristic structural features that suggested a type I or II cell and their presence altered the architecture of the lung. These unique cells were present in localized areas throughout the parenchyma of the lungs, and at all time points examined. There was no evidence of inflammatory infiltrate in the lungs examined from either the animals receiving the CFTR gene or the LacZ gene. This was confirmed by the independent observations of three pathologists.

Immunohistochemical localization of hCFTR protein with a monoclonal antibody specific for CFTR (obtained from Genzyme Diagnostics) revealed positive clusters of cells identified by a red precipitate on the cell surface (FIGS. 4 and 5). Staining was concentrated in the areas of altered lung architecture. FIG. 4 shows immuno-histochemical localization of hCFTR in a five day old pup. FIG. 5 shows localization of the protein in a twelve day old pup (FIG. 5b) and a twenty-two day old pup (FIG. 5d). Each are shown with their parallel processed aged-matched, Ad5.CMVLacZ infected pups (FIGS. 5a and 5c).

The hCFTR protein was present at all points and in all lung tissue examined. At twenty-two days of age, the positive cells were more localized and distinct. Their numbers were decreased in relative proportion to the cells in the unaffected lung parenchyma. This was not surprising as the lung volume increases approximately fifty-fold from the time of infection to twenty-two days of age. At the time of targeting, the infected cells were multipotential and fated for lung development.

FIG. 5d also confirms our previously observed results from LacZ expression. In utero gene transfer and expression of a foreign protein does not result in any inflammatory response and the animals are healthy. Importantly, it also results in entirely normal lung development.

In order to access for functional changes in a phenotypically altered cell (the secretion of glycoconjugates and lipids), tissues were stained with alcian blue/periodic acid schiff (PAS) stain. Alcian blue reacts with compounds containing anionic groups, such as acid mucosubstances and acidic mucins. PAS stains magenta for neutral mucosubstances and neutral glycolipids. In FIG. 6, lungs from normal, Ad5.CMVLacZ infected, five day old rats are compared to age-matched Av1CF2 infected rats. The controls showed only background levels of PAS positive material throughout the lung, while the Av1CF2 infected lungs stained strongly for neutral glycoconjugates. There was little change in the alcian blue staining. Therefore, the cells modified by CFTR expression during development produce large quantities of glycoconjugates throughout the lung. The global presence of these glycoconjugates throughout the lung suggested that these substances were secreted.

Frozen sections of the lungs from the Av1CF2 infected, five day old rats revealed a large amount of neutral lipids (shown by red droplets) present throughout the lung (FIG. 7). Oil Red O is specific for neutral lipids but will not stain phospholipids. The pattern of staining indicated that this lipid (or lipids) was secreted throughout the lung parenchyma and in areas consistent with that previously seen in the immunohistochemical staining of the hCFTR transgene-induced cells (FIGS. 4 and 5).

The secretion of glycoconjugates and lipids is associated with resistance of the lung to infection, however, paradoxically, mucous is increased in patients with CF disease (30). To evaluate whether the altered cells and secreted glycoconjugates and lipids were involved in host defense to infection, adult rats at three months of age, that were infected previously with either Ad5.CMVLacZ or Av1CF2 in utero at 17 days gestation, were challenged by an intratracheal injection of a lethal dose of *Pseudomonas aeruginosa*. The dose chosen to infect the rats was selected so as to be 100% lethal within 12 hours in the rats.

The infection resulted in the death of the first control rat (LacZ infected) at 6 hours post-infection. At that time all of the surviving animals were sacrificed to evaluate bacterial replication in the lungs. There was a marked difference in the weight, bacterial counts and histologic appearance between the lungs of the control animals (LacZ infected) and hCFTR modified animals. FIG. 8 compares the histology of the control (LacZ infected) animals to the Av1CF2 infected animals. The control lungs had a marked acute inflammatory exudate throughout all lung fields. Such exudate was suggestive of fulminant pneumonia. Although there were isolated areas of consolidation in the hCFTR infected lungs, there were entire lobes of the lungs that were normal in appearance. These differences were further documented by the approximately two-fold increase in the lung weights of the control animals over that of the hCFTR-treated animals as shown in Table I, below (p=0.0193).

The lungs were then homogenized and aliquots plated on bacterial culture media to determine the number of colony forming units (CPU) in these *Pseudomonas aeruginosa* infected lungs. As shown in Table 1, there was a significant decrease in bacterial replication in the hCFTR treated lungs. An average of $28 \times 10^9$, or an 85% decrease. Such decrease was statistically significant (p=0.0242).

TABLE 1

| Treatment | Animal | Lung Weight (grams) | Total Colony forming Units |
| --- | --- | --- | --- |
| LacZ | 1 | 5.058 | $2.4 \times 10^{10}$ |
| LacZ | 2 | 6.615 | $3.8 \times 10^{10}$ |

TABLE 1-continued

| Treatment | Animal | Lung Weight (grams) | Total Colony forming Units |
|---|---|---|---|
| LacZ | 3 | 6.6 | $2.2 \times 10^{10}$ |
|  | Average | 6.091 | $2.8 \times 10^{10}$ |
|  | S.D. | 0.895 | $4.56 \times 10^{9}$ |
| CFTR | 1 | 3.31 | $6.8 \times 10^{9}$ |
| CFTR | 2 | 3.15 | $1.3 \times 10^{9}$ |
| CFTR | 3 | 3.0 | $2.4 \times 10^{8}$ |
|  | Average | $3.15^{(1)}$ | $2.76 \times 10^{9(2)}$ |
|  | S.D. | 0.155 | $3.53 \times 10^{9}$ |

$^{(1)}$P = 0.0193
$^{(2)}$P = 0.0242

Despite its altered appearance, the Av1CF2 infected lung function was not grossly compromised. The infected animals did not appear to be affected by the expression of the hCFTR gene. As demonstrated in FIGS. 9 and 10, CFTR expression in the fetal lung differed significantly from that seen with Ad5.CMVLacZ and resulted in some unique structures.

Immunohistochemical identification of hCFTR in 12 day old rats (FIGS. 9a and 9b), revealed that the protein was associated with dilated areas around either major airways and/or vessels. These structures appear to be vesicular in nature. Red blood cells were not present. This distribution of transgene expression was completely different then that observed with LacZ expression. As shown in FIG. 7C the type I and II cells lining the major airways was the primary site of expression of the reporter gene LacZ.

Individual nests of cells were identified in paraffin fixed tissues. Groups of cells appeared to organize into acini-like structures in the day 12 and 22 CFTR treated lungs. This is demonstrated in FIG. 10 by a PAS stain with hematoxylin counterstain. These distinct areas (indicated by arrow) were readily seen in the paraffin thin sections of Av1CF2 infected pups, but were not present in lungs from the Ad5.CMVLacZ animals.

As will be appreciated, cellular differentiation is defined as the process by which cells acquire their specialized phenotypes (25). In the development of the lung parenchyma, two epithelial cell types, the alveolar type I and type II cells, are the most abundant. In this work, we targeted stem cells fated for lung parenchyma. When targeted with the LacZ reporter gene, expression remained confined to the epithelium and the lung had no functional changes. However, targeting the same cells with the CFTR gene resulted in altered patterns of expression, phenotypic changes, and altered function in the lung. Neither set of animals showed any inflammatory response.

Immunohistochemistry, as shown in FIGS. 4 and 5, demonstrated that in utero modification of stem cells in the lungs was extremely effective at inserting the transgene and maintaining its expression. The PAS and Oil red O stains (FIGS. 6 and 7) revealed that the Av1CF2 infected fetuses had global changes in their lung architecture and function. The widespread effect on the lung and the long term change in function is illustrated by the enhanced resistance to Pseudomonas aeruginosa infection three months after infection with the hCFTR recombinant adenovirus.

It has been estimated that the lifespan of the epithelial cell in the rat lung at this age ranges from 60–90 days (28). The continued changes in function of the lung after the expected lifespan of the infected cells pose several interesting possibilities. Integration of Av1CF2 would maintain continued expression of CFTR. Our preliminary data indicates that there is no integration of the virus.

As mentioned above, at the time of birth, there is no detectable viral DNA expression by PCR and no hCFTR expression by RT-PCR. This is consistent with the extensive work with adenovirus revealing that it remains largely episomal.

A second possibility is that the changes observed may be due solely to the effects of transient, ectopic hCFTR. While these effects may or may not be amplified by enhanced endogenous production of rCFTR, our preliminary results by PCR indicate that rCFTR is not upregulated. Thus, it is expected that the changes seen in the lungs of these animals reflect more functions of CFTR than its role as a cAMP regulated chloride channel. It has been suggested that the abnormal viscolelastic properties of the respiratory tract mucous from CF patients is largely due to lung fluid imbalances in the lung that result from a defective chloride channel (30). This abnormal mucous increases the susceptibility of patients having CF disease to bacterial infection. However, the chloride channel function of CFTR does not explain the secreted glycoconjugates and lipids demonstrated throughout the parenchyma of the infected lungs that have been observed in connection with the present invention. Although it is possible that these may be a normal lung response to the presence of the exogenous protein, there is no other evidence of inflammatory reaction throughout any of the tissues examined, including the control animals treated with the LacZ containing adenovirus.

We have also preliminarily tested the hypothesis by delivering df508 in accordance with the invention, a mutated form of the CFTR gene containing changes to the portion of the gene encoding the nucleotide binding region (NB-1). df508 produces none of the changes observed with CFTR treatment.

Thus, it is expected that the secreted substances are involved in primary lung defense and are produced by secretory cells that are produced by hCFTR's role in development and differentiation of pleuripotential stem cells that are infected in accordance with the invention. Fung et al. (30) demonstrated the production of glycoconjugates and lipid complexes in a mucin-like substance in response to challenge with a Pseudomonas aeruginosa toxin. The demonstrated resistance of in utero hCFTR modified lungs to bacterial infection implies a role of these substances. Typically gram negative bacteria require an inflammatory response to eradicate the infection. Interestingly, the lungs in the hCFTR treated animals were less infected and had no inflammation. See FIG. 8. These results may have several explanations: 1) "antibacterial" properties in the materials secreted by the cells; 2) neutralization of virulence factors of Pseudomonas aeruginosa; or 3) enhanced clearance from the lung by increased function of alveolar macrophages or other cell types.

However, such explanations do not appear to fully take into account the results that we have observed in connection with the present invention, particularly the fact that these effects were seen three months after birth. Therefore, it is expected that additional mechanisms are involved in the "immunoprotection" of the lungs that were treated with the hCFTR gene. In particular, it is expected that the CFTR gene influences cellular differentiation of a stem cell during development that results in the overproduction of secretory cell population that is directly involved in host defense to Pseudomonas aeruginosa, other bacterial, and other infectious or pathenogenic agents.

CFTR, mRNA and CFTR protein have been demonstrated to be present in fetal lung tissue. Its role, however, other than in cAMP regulated chloride channeling, has remained unclear. Our data strongly indicates a previously unknown and highly useful new role of CFTR in cellular development and differentiation. Such paradigm can be summarized as follows: CFTR is a necessary protein in the development of a secretory cell type(s) in the lung. Moreover, such secretory cell type(s) appear involved in primary host defense to bacterial, viral, and other pathogenic infection. One aspect, if not the primary or sole aspect of such defense, is the secretion of "immunoprotectant factors" comprising glycoconjugates and lipids which act to protect the lung, and presumably other organs, tissues, and cells from pathogenic infection.

An interesting additional fact that supports the role of CFTR in cellular development and differentiation is the demonstrated sequence homology between nucleotide binding regions of the CFTR protein product and the a-subunits of G-protein (6). One of the conserved sequences, GGQR, within which a number of CF mutations occur, forms part of the nucleotide binding pocket. Such sequence morphology serves as an ON/OFF switch in GTP-binding proteins. There are many regulatory peptides that influence cell growth and act to bind specific receptors coupled to G proteins. Indeed, certain work has demonstrated that G-proteins may influence the effects of growth factors to direct a cell along a particular developmental pathway (26).

Accordingly, it will be appreciated that mutations in the CFTR gene that altered or eliminated this function during development of the lung would prevent the development of the cell type(s) required for production of normal lung secretions, as our work with df508 has indicated. Thus, the paradox of increased mucous, altered glycosylation, and changes in sialyation seen in CF disease may be due to the lungs efforts to compensate for the lack of normal secretory function and production of glycoconjugates and lipids. These changes would not be readily apparent with overexpression in an in vitro model unless one were to happen to transfect the correct plueripotential stem cells.

Based on this new paradigm for a developmental role of CFTR, in utero expression of the hCFTR gene in plueripotential stem cells causes an increase in the number of cells committed to the secretory cell differentiation (FIGS. 3–7). The abnormal lung architecture and secreted proteins observed reflect this increased population of cells. Because these cells are now committed to the secretory function, their progeny cells continue to function enhancing the resistance of the animals to infectious and pathogenic agents, such as *Pseudomonas aeruginosa* infection (Table I; FIG. 8). Thus, the recombinant adenovirus that is lost in progeny generation is no longer required, since the cells have developed the function through cellular development and differentiation as directed by CFTR. Alternatively, the rat CFTR may be activated during the differentiation process and maintain function in succeeding generations.

Applications

From the foregoing, it will be appreciated that a variety of highly useful cell culture and therapeutic applications become evident in accordance with the present invention. Such applications will be discussed in greater detail below.\
Isolation, Purification, Characterization of Secretory Cells and Cellular Products Applications related to screening can take several forms. In particular, we expect that it will be useful to screen for secretory cells in patients lungs in order to ascertain susceptibility of patients lungs to infection. A primary method through which screening can be conducted is through the use of antibodies. In addition, antibodies can also be utilized for the isolation and purification of secretory cells and their cellular products (i.e., glycoconjugates and lipids), particularly those that are acting as immunoprotectant factors.

As will be appreciated, antibodies can be raised against various epitopes of secretory cells or cellular products. Such antibodies can be utilized for the diagnosis of CF disease, or other secretory cellular dysfunction, and, in certain applications, targeting of affected tissues. Thus, in accordance with another aspect of the present invention a kit is provided that is suitable for use in screening and assaying for the presence of the above-epitopes by an immunoassay through use of an antibody which specifically binds to epitope containing products in combination with a reagent for detecting the binding of the antibody to the product.

Antibodies raised in accordance with the invention can also be utilized to provide extensive information on the characteristics of the protein and of the disease process and other valuable information which includes but is not limited to:

1. Antibodies can be used for the immunostaining of cells and tissues to determine the precise localization of the protein. Immuno-fluorescence and immuno-electron microscopy techniques which are well known in the art can be used for this purpose. Defects in cells or cellular products which cause an altered localization of the proteins are expected to be localizable by this method.

2. Antibodies can also be used as tools for affinity purification of cells of protein products. Methods such as immunoprecipitation or column chromatography using immobilized antibodies are well known in the art.

3. Immunoprecipitation with specific antibodies is useful in characterizing the biochemical properties of the cells and protein products. Modifications of the protein products (i.e., phophorylation, glycosylation, ubiquitization, and the like) can be detected through use of this method. Immunoprecipitation and Western blotting are also useful for the identification of associating molecules that are involved in signal transduction processes which regulate transport or other metabolic functions important in the disease process.

4. Antibodies can also be utilized in connection with the isolation and characterization of tissues and cells which express the protein products. For example, immunoprotectant protein expressing cells can be isolated from the lungs, gut, other tissues, or from cultured cells by fluorescence activated cell sorting (FACS) ("Antibodies" Cold Spring Harbor Press). Cells can be mixed with antibodies (primary antibodies) with or without conjugate dies. If non-conjugate antibodies are used, a second dye-conjugated antibody (secondary antibody) which binds to the primary antibody can be added. This process allows the specific staining of cells or tissues which express the immunoprotectant proteins.

Antibodies against the secretory cells or immunoprotectant protein products can be prepared by several methods that are well known in the art which include, but are not limited to:

1. The potentially immunogenic domains of the cells or immunoprotectant proteins are predicted from hydropathy and surface probability profiles. Then oligopeptides which span the predicted immunogenic sites are chemically synthesized. These oligopeptides can also be designed to contain the specific mutant amino acids to allow the detection of the specific epitopes. Rabbits or other animals are immunized with the synthesized oligopeptides coupled to a carrier such as KLH to produce polyclanal antibodies. Alternatively, monoclonal antibodies can be produced against the synthesized oligopeptides using conventional techniques that are well known in the art ("Antibodies" Cold Spring Harbor Press). Both in vivo and in vitro immunization techniques can be used. For therapeutic applications, "humanized" monoclonal antibodies having humas constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525–535 (1995).

2. Antibodies can also be raised against expressed immunoprotectant factor products from cells. Such expression products can include the fall length expression product or parts or fragments thereof. Expression can be accomplished using conventional expression systems, such as bacterial, baculovirus, yeast, mammalian, and other overexpression systems using conventional recombinant DNA techniques. The proteins can be expressed as fusion proteins with a histidine tag, glutathione-S-transferase, or other moieties, or as nonfused proteins. Expressed proteins can be purified using conventional protein purification methods or affinity purification methods that are well known in the art. Purified proteins are used as immunogens to generate polyclonal or monoclonal antibodies using methods similar to those described above for the generation of antipeptide antibodies.

In each of the techniques described above, once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

As mentioned, a principle utility of antibodies in accordance with the present invention is for use in the isolation, separation, and/or purification of secretory cells of the invention and/or their cellular products, and in particular isolation and purification of immunoprotectant products from the secretory cells, such as glycoconjugates and lipids.

Isolated secretory cells can be utilized to generate cell cultures of secretory cells. Such cell lines can thereafter be used for the production and isolation of immunoprotectant factors. In accordance with the present invention, there are essentially two routes that are utilized in connection with the isolation and culturing of secretory cells. First, secretory cells can be isolated from mature lung tissues, for example, following in utero gene transfer in accordance with the invention. Typically, this approach is useful in smaller animals, such as rats, mice, pigs, sheep, primates, and the like. Where larger animal secretory cells (such as humans) are desired to be formed, or even in the case of smaller animals, it is possible to directly culture pleuripotential stem cells from such animals, and transfect the cultured pleuripotential stem cells with the hCFTR gene under conditions designed to allow expression of the hCFTR gene and development and differentiation of the pleuripotential stem cells. In this manner, it is expected that a culture of secretory cells will be formed.

In certain instances, it may be advantageous to include other lung cells in the culture with the pleuripotential stem cell culture. Such cells may beneficially assist in differentiation and development of the pleuripotential stem cells into secretory cells in accordance with the present invention. In other instances, it may prove beneficial to include certain growth factors and/or certain chemokines, cytokines, lympokines, or the like within the culture with the pleuripotential stem cells in order to assist in cellular development and differentiation.

While for human therapeutic and other applications, it would be most desirable to generate cultures of human pleuripotential stem cells, which could then be processed in accordance with the invention to form human secretory cells, as will be appreciated, it may also be possible to culture pleuripotential stem cells from animals that are genetically similar to humans. For example, certain primates, such as baboons, apes, and orangutans, and certain other mammals, such as pigs, possess relative genetic similarities to humans in certain contexts. Thus, it is expected that pleuripotential stem cell cultures can be prepared from such animals and the cultures transfected with hCFTR, allowed to develop and differentiate to form secretory cells with greater genetic similarity to human secretory cells.

Upon generation of secretory cell lines, whether through direct isolation from mature lung tissue following in utero gene transfer in accordance with the invention, or through preparation of such cultures from pleuripotential stem cells in vitro, it will be appreciated that such cell lines are useful for the production, isolation, purification, and characterization of cellular products of such cells, and particularly the immunoprotectant factors produced by such cells.

Glycoconjugate and lipid isolation, purification and characterization can be accomplished through use of techniques that are well known in the art. For example, crude fractions can be processed through non-denaturing (i.e., polyacrylamide) or denaturing gel electrophoresis (i.e., SDS-PAGE), bands cut and suspended and characterized. Alternatively, various types of chromatographic techniques can be employed, such as column chromatography, affinity chromatography (using ligands specific for glycoconjugates or lipids), high performance liquid chromatography, and the like. Purified fractions can be utilized for the preparation of polyclonal or monoclonal antibodies as discussed above.

Characterization of the isolated fractions can be accomplished using protein chemical techniques that are well known in the art. For example, inununohisto-chemistry using lectins for carbohydrate detection and characterization, immunoblotting in order to compare the products in samples from normal, non-CFTR treated mammals, versus CFTR treated mammals, neutral lipid detection techniques, and the like, can each be utilized, without undue experimentation, to characterize the cellular products that are unique to the CFTR gene treated secretory cells. Following gross characterization, specific structural studies can be undertaken, including mass spectroscopy, nuclear magnetic resonance, circular dichromism, electron scattering spectroscopy, and if desired, x-ray crystallography.

Even without exhaustive characterization, the crude or partially purified cellular expression products from the secretory cells are highly useful. Crude or partially purified expression products can be readily screened in vitro for their immunoprotectant properties toward other cells in culture, for example, upon challenge with low, moderate, or high doses of *Pseudomonas aeruginosa*. Fractions yielding the highest viable cell counts in culture, following challenge, can be subjected to additional purification and characterization, if desired, or used neat in certain therapeutic procedures. Further, such fractions can be utilized for the generation of polyclonal or monoclonal antibodies. Polyclonal or monoclonal antibodies so generated can be utilized in connection with certain affinity purification procedures, such as affinity chromatography, to isolate and purify immunoprotectant factors from fully crude fractions derived from secretory cells.

Therapeutic Applications

Immunoprotectant factors in accordance with the invention are expected to be highly useful in connection with protecting cells and tissues from opportunistic infections, such as bacterial, viral, and others. In connection with our discussion above, we have demonstrated that through treating a neonatal mammal with a viral vector including the hCFTR gene in utero at a time when the prenate is practicing fetal breathing and the respiratory epithelium is lined with pleuripotential stem cells, a secretory cell type can be formed, which cell type secretes immunoprotectant factors. Similar pleuripotential stem cells also line the gut, during its development and we expect that it will be possible to target the gut in a similar manner in which the lung has been targeted. It is expected that the gut, so treated, will be resistant to opportunistic infections, such as E. Coli infection. Thus, two broad therapeutic applications of the present invention are in the generation of immunoprotectant factor generation in the lungs and in the gut of neonates, which immunoprotectant factors are continued to be generated while the mammal matures.

Yet, the secretory cells generated through the above-discussed treatment and the immunoprotectant factors produced by such cells are believed to be unique and valuable therapeutic targets as well. It is envisioned in accordance with the present invention that fully isolated, purified, and characterized immunoprotectant factors, and even less purified fractions containing immunoprotectant factors, will be useful in the mitigation or treatment of infection of cells or tissues by opportunistic organisms, such as bacteria, virus, and/or the like.

Isolated secretory cells, isolated from in vivo or in vitro sources, for example, can be infused or implanted in proximity to cells or tissues in need of immunoprotection from opportunistic infection. For instance, it is expected that such cells could be infused, or implanted, into the lungs of a patient suffering from CF disease to immunoprotect the patient's lungs from opportunistic infection. Similarly, such cells, or similar cells, could be infused or implanted into the gut of a patient suffering from toxic E. Coli or other opportunistic infection.

Immunoprotectant factors, isolated from secretory cells (either in vivo or in vitro) can be utilized in therapies to immunoprotect patient's cells from opportunistic infections. Purified factors, in particular, can be utilized in a lung lavage, for example, in assisting patients with CF disease substantially avoid respiratory distress. Similarly, certain opportunistic infections in the gut might similarly be mitigated through the use of immunoprotect factors in accordance with the invention.

Isolated and characterized immunoprotectant factors can be utilized in the design of drugs to immunoprotect cells. This can be accomplished through gathering knowledge of the structure and function correlations of the immunoprotectant factors. Further, knowledge of the structure and function of the immunoprotectant factors can be assessed in relation to structure and function of factors present in the lungs or other tissues of CF patients to determine the missing molecules or differences between the molecules. As will be appreciated, rational drug design through the use of X-ray crystallography, computer-aided molecular modeling (CAMM), QSAR and similar technologies can provide significant information and assist in further focusing drug discovery efforts. Rational design allows prediction of protein or synthetic structures which can act as immunoprotectant factors in accordance with the invention. Such structures may be synthesized chemically or expressed in biological systems. This approach has been reviewed in Capsey et al., Genetically Engineered Human Therapeutic Drugs, Stockton Press, New York (1988). Further, combinatorial libraries composed of either piptidic or small molecule targets can be designed, synthesized, and used in screening programs, such as high throughput screens. As will be appreciated, synthesis of molecular targets for use in combinatorial libraries, whether peptidic or small molecules, can be obtained on a contract basis through a variety of companies. Further, several companies also offer high throughput screening on a contract basis.

It is expected that certain of the immunoprotectant factors of the present invention are peptidic in backbone. Thus, gene therapeutic and protein replacement therapies become possible and are envisioned in accordance with the present invention. As will be appreciated, peptides can be expressed by genes. It is routine to develop gene expression cassettes designed to express peptides of known structures. Such cassettes can be included in an expression system, such as a viral vector, under the control of appropriate promoters, regulators, and the like, for delivery to patients to cause expression of the immunoprotectant factors in vivo. Tissue specific promoters, i.e., lung (the SP-C promoter sequence), gut, liver, and the like, can be included in the expression system in order to more particularly target affected tissues. Immunoprotectant peptides/proteins can thus be produced in vivo and utilized to mitigate or prevent opportunistic infections. In certain instances, post-translational events, such as glycosylation, phosphorylation, and other events may be necessary to lend additional therapeutic value to such peptides/proteins. In such event, helper or regulatory sequences may need to be included in the expression cassette to ensure proper post-translational processing of the peptide/protein.

Alternatively, proteins/peptides, glycoconjugates, and even lipids, acting as immunoprotectant factors, can be utilized directly in "replacement" therapies. In such a case, such proteins, lipids, or other agent can be produced, for example, isolated and purified from a secretory cell line in vitro or synthesized, and delivered to affected tissues of cells directly.

Diseases, particularly those in which there is substantial bacterial colonization, are particularly amenable to treatment in accordance with the invention. Lung and gut infections, especially, are amenable for this reason. In connection with lung infections, sprays, aerosols, and lavages are preferred delivery modes. In the guts, pills and lavages can be utilized.

Gene Constructs

In addition to the relatively straightforward goal of treating CF in accordance with the present invention, it will be appreciated that a variety of delivery vehicles can be utilized to effect delivery of any particular gene and enhance uptake and expression.

The term "gene" or "gene construct" as used in connection with the present invention can include virtually any gene that is desired to be delivered into cells of an infant mammal. Particularly preferred categories of genes in accordance with the present invention, where the present invention is used to transfer a gene into the lungs of an infant, include genes that are capable of treating a genetic defect that affects the lungs, genes that will assist the lung in maturing, genes that are capable of treating a genetic defect that is present in another part of the body, such as an enzymatic deficiency, and the like. For example, immediately useful genes in accordance with this aspect of the invention include the class of genes that are defective in CF (i.e., the CFTR gene), the class of genes encoding surfactant proteins (i.e., the SP-C gene (see Glasser et al. "Structure and expression of pulmonary surfactant protein SP-C gene in the mouse", *JBC* 265:21986–21991), the genes that are involved in diseases related to enzymatic deficiencies (i.e., the ADA gene, the AAT gene and others), the class of genes that encode particular growth factors that aid in lung growth and development (e.g., EGF,TGB-beta, FGF, PDGF, and others).

Where the present invention is used to deliver a gene to tissues other than the lung, a variety of genes become especially applicable. For instance in connection with the gut, where expression is also observed (presumably when an animal swallows amniotic fluid containing the vector) there are a variety of genes that can be used to treat conditions and maladies afflicting the gut. Certain immnune regulator proteins, such as chemokines, cytokines, and, particularly, interleukins ("IL") (i.e., IL-1, IL-2, IL-3,IL-4, IL-5, . . . IL-13, and the like) can be useful.

As was mentioned above, in connection with fetal breathing, fetal animals also "swallow" amniotic fluid. Generally, the swallowing of amniotic fluid occurs at a time earlier than true fetal breathing. Thus, during development of the gut, genes can be targeted thereto to aid in development thereof or prevent future diseases. Delivery is accomplished in a manner identical to lung delivery, however, the time for delivery will generally proceed the time for lung delivery (i.e., before day 16 in rats). Techniques such as that described in connection with Example (II)(C)(1), above, can be utilized to visualize the optimum date for gut targeting.

Another highly accessible tissue to the gene transfer methods of the present invention is the skin. Delivery in accordance with the present invention is relatively simpler in that the gene does not need to access the internal tissues of the fetus. Rather, the skin is direct contact with the amniotic fluid. However, delivery needs to be accomplished at a time when the gene can be effectively uptaken in the appropriate skin cells through the use of appropriate delivery agents. For example, adenoviral vectors do not target skin cells very effectively; however, liposomes appear to be far more effective in targeting skin. Yet, even through the use of adenoviral vectors, we, in some instances see expression in the skin. See also McCray et al. "Adenoviral-mediated gene transfer to fetal pulmonary epithelia in vitro and in vivo" *J. Clin. Invest* 95:2620–2632 (1995), the disclosure of which is hereby incorporated by reference. Theoretically, many genetic defects of the skin could be treated, such as causing skin cells to produce pigment in albinism through the inclusion of pigmentation proteins. One could also add curative genes to prevent melanoma, i.e., akin to a "mosaic" cancer therapy approach. See Moolten *Med Hypotheses* 24:43 (1987), the disclosure of which is hereby incorporated by reference.

In theory, the present gene therapeutic approaches can be used far earlier in development of a fetus than were the cells are as differentiated as in the case in connection with lung, gut and skin. Thus, the present gene transfer techniques can be used in connection with delivery of genes very early in gestation, i.e., where the fetus is in blastula form. As will be appreciated, in this phase, it may be possible to deliver a gene to virtually all of the cells of an infant. This technique might prove useful in delivery of a therapeutic gene to the embryo of an AIDS infected mother, for example. Or, might prove useful in connection with attainment of the "mosaic" approach to cancer therapy. In addition, the technique might be useful in the preparation of transgenic animals or "knock-out" animals.

Thus, the term gene in accordance with the present invention can relate to any expressible message encoded in a oligo or polynucleotide sequence including antisense message, where appropriate.

The term construct is intended to cover both the base message as well as peripheral message that may be appropriate to a particular therapeutic scheme. For example, promoter sequences, including tissue specific promoters, can be utilized to enhance a particular therapeutic scheme. Markers, such as positive selectable markers (i.e., the neomycin resistance gene (the neo gene) and negative selectable markers (i.e., the herpes simplex thymidine kinase gene (the TK gene or the cytosine deaminase gene) can be utilized to allow, for example, separation of gene construct in vitro or in vivo, respectively. Those of ordinary skill in the art will readily comprehend the use of these peripheral messages in attaining particular results in accordance with the present invention.

It will further be appreciated that the gene can be a native or full-length gene product of can be a recombinant or modified gene product. In many situations, it is desirable to deliver less than the full, natural gene, both from the perspective of delivery and efficiency of expression. For example, with respect to the ATT gene, a gene construct including all of the expressed sequences and the non-expressed Intron II sequence is more efficiently expressed than a construct that merely includes the expressed sequences. See Brantly et al. U.S. Pat. No. 5,439,824, the disclosure of which is hereby incorporated by reference. Thus, the term gene, as used herein, is intended to cover the various modifications to genes that can enhance delivery and/or facilitate expression of the gene.

Further, the gene or gene construct can be carried or delivered in virtually any form, such as through use of a viral vector, naked DNA, as a conjugate (DNA, liposomal, or the like), and many other forms.

Appropriate viral vectors include adenoviral vectors, adeno-associated viral vectors, retroviral vectors, other DNA virus vectors, as well as others. Such vectors, can, as will be understood, be fully capable of replication or can be replication defective. Where a vector that is fully capable of replication is utilized, it is expected that follow-on treatment may not be necessary. In contrast, where a replication defective vector is utilized, further treatment may be necessary. With the potential for immunotolerization of fetuses in accordance with the invention, follow-on therapies could be well tolerated without the observation of the immune response that is observed over time where therapy is initiated in an adult.

In particular gene transfer techniques, naked DNA introduced into an animal has been shown to be uptaken be cells and expressed therein. Therefore, it is expected that in certain gene transfer strategies in accordance with the present invention, naked DNA can be provided, uptaken by cells of the fetus, and expressed therein. Where naked DNA, however, is utilized, it is expected that follow-on therapies, may be necessitated. Yet, as discussed in connection with vector based therapies, immunotolerization in fetuses may minimize the negative impacts therein.

In connection with any viral vector based gene and naked DNA based gene transfer strategies, certain delivery agents have been shown to enhance targeting, uptake, and expression of protein by cells. Such delivery agents include liposomes (such as LIPOFECTIN™ available commercially from Life Technologies, Inc., Bethesda, Md., and DNA conjugates which are under experimental development by several groups. Other groups have reported the development of delivery enhancing moieties that can be attached to DNA messages that enhance delivery of the DNA across cell membranes and into cells. Such delivery enhancing moieties were developed principally with the delivery of antisense oligonucleotides in mind. However, it is expected that they will also be useful in connection with other gene products. Therefore, such moieties can be used in accordance with particular delivery schemes in accordance with the invention.

Accordingly, delivery agents, such as the foregoing, as well as others, are contemplated in accordance with the present invention.

Dosing in accordance with the present invention is preferably on the order of $10^2$ through $10^9$ PFU ml-1 amniotic fluid, when using viral vectors. It is expected that where viral vectors are used in doses $10^{12}$ PFU ml-1 amniotic fluid, and above, immune responses in patients are observed. This is believed to have contributed to the response seen in McCray et al. "Adenoviral-mediated gene transfer to fetal pulmonary epithelia in vitro and in vivo" J. Glin. Invest. 95:2620–2632 (1995). Thus, doses of between about $10^2$ and less than about $10^{12}$ PFU ml-1 amniotic fluid are highly preferred in accordance with the invention. And, doses between about $10^2$ through $10^9$ PFU ml-1 amniotic fluid are most highly preferred.

Those of ordinary skill in the art will understand how to apply the dosage information relating to viral vectors to the delivery of other gene constructs and will be able to arrive at appropriate dosing without undue experimentation.

From the foregoing, it will be appreciated that a significant variety of diseases can be fought through use of this present invention. As well, a variety of fundamental genetic manipulations can be accomplished through use of the present invention. Thus, while the invention has been described with reference to certain particular embodiments, the scope of the present invention should be construed broadly and to cover equivalents of the subject matter described. The following references are hereby incorporated by reference in their entirety:

The following references are hereby incorporated by reference in their entirety:

1. Rommens et al. "Identification of the cystic fibrosis gene: chromosome walking and jumping" Science 245:1059–1065 (1989)
2. Guggino et al. "Mechanisms for interaction of CFTR with other secretory CL-channels" Pedatric Pulmonology S12:239 (1995)
3. Bradberry et al. "Regulation of plasma membrane recycling by CFTR" Science 256:530–531 (1992)
4. Kube et al. "Quantitative floursecent microscopy reveals altered cell surface glycoconjugates on 9HTEo cells transfected with the regulatory domain of CFTR or DF508 CFTR" Pediatric Pulmonology S12:238, 1995.
5. Weyer et al. "Immunolocalization of two sialytransferases is altered in polarized LLC-PK1 epithelial cells expressing DF508 CFTR" Pediatric Pulmonology S12:238, 1995.
6. Monavalin et al. "Sequence homologies between nucleotide binding regions of CFTR and G-proteins suggest strucutral and functional similarities" FEBS Letters 366:87–91, 1995.
7. McGrath et al. "Cystic fibrosis gene and protein expression during fetal lung development" Am. J. Respir. Cell Mol. Biol. 8:201–208, 1993.
8. Tizano et al. "Regional expression of CFTR in developing human respiratory tissues" Am. J. Respir. Cell Mol. Biol. 10:355–362, 1994.
9. Gaillard et al. "Immunohistochemical localization of cystic fibrosis transmembrane conductance regulator in human fetal airway and digestive mucosa" Pediatr Res 36:137–143, 1994.
10. McCray et al. "Localization of cystic fibrosis transmembrane conductance regulator mRNA in human fetal lung tissue by in situ hybridization" J. Clin. Invest. 90:619–625, 1992.
11. Harris et al. "Expression of the cystic fibrosis gene in human development" Development 113:305–310 (1991).
12. Koch et al. "Pathogenesis of cystic fibrosis" Lancet 341:1065–1069 (1993)
13. Gilligan et al. "Microbiology of airway disease in patients with cystic fibrosis" Clin. Microbiol. Rev. 4:35–51 (1991)
14. Deretic et al. "Conversion of Pseudomonas aeruginosa to mucoidy in cystic fibrosis: Environmental stress and regulation of bacterial virulence by alternative sigma factors" J. Bacteriol. 176:2773–2780 (1994).
15. Plotkowshi et al. "Cellular and molecular mechanisms of bacterial adhesion to respiratory mucosa" Eur. Respir. J. 6:903–916 (1993)
16. Berger, M. "Inflammation in the lung in cystic fibrosis: a vicious cycle that does more harm than good?" Clin. Rev. Allergy 9:119–142 (1991).
17. Marshall E. "Gene therapy's growing pains" Science 269:1050–1055 (1995).
18. Wilson J M. Pediatric Pulmonology S12 (1995)
19. Knowles et al. "A controlled study of adenoviral-vector-mediated gene transfer in the nasal epithelium of patients with cystic fibrosis" N. ENg. J Med 333:823–831 (1995).
20. Crystal et al. "Administration of an adenovirus containing the human CFTR cDNA to the respiratory tract of individuals with cystic fibrosis" Nature Genetics 8:42–51 (1994).
21. Snouwaert et al. "A murine model of cystic fibrosis" Am. J. Respir. Crit. Care Med. 151:S59-S64, 1995.
22. Ballard et al. "Adenovirus-mediated gene transfer to human fetal lung ex vivo" Am. J. Physiol. 268:L839-L845, 1995.
23. Ragot et al. "Efficient adenovirus-mediated transfer of a human minidystrophin gene to skeletal muscle of mdx mice" Nature 361:647–650
24. Sekhon H S, and Larson, J E. "In utero gene transfer into the pulmonary epithelium" Nature Medicine 1:1201–1203, 1995.
25. Ten Have-Opbroek A. A. W. "The development of the lung in mammals: An analysis of concepts and findings" Am. J. Anat. 162:201–219 (1981).
26. Hislop et al. "Development of the acinus in the human lung" Thorax 29:90–94 (1974)
27. Adamson, I. Y. R. "Development of Lung Structure. The Lung: Scientific Foundations by R. G. Crystal. J. B. West et al. Raven Press, Ltd., New York. 663–666 (1991).
28. Kauffman, S. L. "Cell proliferation in the mammalian lung" Int. Rev. of Exp. Path. 22:131–191 (1980).
29. Adamson et al. "Derivation of Type 1 Epithelium from Type 2 Cells in the Developing Rat Lung" Lab. Invest. 32(6):736–745 (1975).

30. Fung et al. "Mucus glycoconjugate complexes released from feline trachea by a bacterial toxin" *Am. J. Respir Cell Mol Biol* 12:296–306 (1995)
31. Margraf et al. "Morphometric analysis of the lung in bronchopulmonary dysplasia." *Am. Rev. Respir. Dis.* 143, 391–400 (1991).
32. Sobonya et al. "Morphometric analysis of the lung in prolonged bronchopulrnonary dysplasia." *Pediatr. Res.* 16, 969–972 (1982).
33. Harding, R. "Fetal breathing movements." *The lung: Scienific Foundations Eds,* R G Crystal, J B West, et al. Raven Press, Ltd., New York. 1655–1656 (1991).
34. Ten Have-Opbrock A. A. W. "The development of the lung in mammals: An analysis of concepts and findings." *Am. J. Anat.* 162, 201–219 (1981).
35. Kauffinan, S. L. "Cell proliferation in the mammalian lung." *Int. Rev. of Exp. Path.* 22, 131–191 (1980).
36. Winick et al. "Quantitative changes in DNA, RNA, and protein during prenatal and postnatal growth in the rat." *Devel. Biol.* 12, 451–466 (1965).
37. Stratford-Perricaudet et al. "Widespread long-term gene transfer to mouse skeletal muscles and heart." *J. Clin. Invest.* 90, 626–630 (1992).
38. Mastrangeli et al. "Diversity of airway epithelial cell targets for in vivo recombinant adenovirus-mediated gene transfer." *J. Clin. Invest.* 91, 225–234 (1993).
39. Crystal et al. "Administration of an adenovirus containing the human CFTR cDNA to the respiratory tract of individuals with cystic fibrosis." *Nature Genetics* 8, 42–51 (1994).
40. Kolls et al. "Prolonged and effective blockade of tumor necrosis factor activity through adenovirus-mediated gene transfer." *Proc. Natl. Acad. Sci.* 91, 215–219 (1994).
41. Hislop et al. "Development of the acinus in the human lung." *Thorax* 29, 90–94 (1974).
42. Adamson. "Development of Lung Structure." *The Lung: Scientific Foundations* by R. G. Crystal, J. B. West et al., Raven Press, Ltd., New York. 663–666 (1991).
43. Adamson et al. "Sex-related differences in cellular composition and surfactant synthesis of developing fetal rat lungs." *Am. Rev. Respir. Dis.* 129, 130–134 (1984).
44. Adamson et al. "Derivation of Type 1 Epithelium from Type 2 Cells in the Developing Rat Lung." *Lab. Invest.* 32(6), 736–745 (1975).
45. Bolduc et al. "Mitotic index of the bronchial and alveolar lining of the normal rat lung." *Am. Rev. Resp. Dis.* 114, 1121–1128 (1976).
46. Adamnson et al. "Sex differences in development of fetal rat lung." *Lab. Invest.* 50(4), 456–460 (1984).
47. Yang et al. "Cellular immunity to viral antigens limits El-deleted adenoviruses for gene therapy." *Proc. Natl. Acad. Sci.* 91, 4407–4411 (1994).

In addition, any references that are cited in the present text that are not already specifically incorporated by reference, are herein incorporated by reference in their entirety.

48 Ackerman, M. J. and D. E. Clapham (1997). "Ion channels—basic science and clinical disease [published erratum appears in N Engl J Med Aug. 21, 1997;337(8) :579]." *N Engl J Med* 336(22): 1575–86.
49 Arispe, N., J. Ma, et al. (1998). "Direct activation of cystic fibrosis transmembrane conductance regulator channels by 8-cyclopentyl-1,3-dipropylxanthine (CPX) and 1,3-diallyl-8-cyclohexylxanthinc (DAX)." *J Biol Chem* 273(10): 5727–34.
50 Berger, H. A., S. M. Travis, et al. (1998). "Fluoride stimulates cystic fibrosis transmembrane conductance regulator Cl- channel activity [In Process Citation]." *Am J Physiol* 274(3 Pt 1): L305–12.
51 Bianchet, M. A., Y. H. Ko, et al. (1997). "Modeling of nucleotide binding domains of ABC transporter proteins based on a F1-ATPasc/recA topology: structural model of the nucleotide binding domains of the cystic fibrosis transmembrane conductance regulator (CFTR) [In Process Citation]." *J Bioenerg Biomembr* 29(5): 503–24.
52 Blau, H. M. (1985) Hierarchies of regulatory genes may specify mammalian development. Cell 53: 673–674.
53 Blau, H. M., and Baltimore D. (1991) Differentiation requires continuous regulation. J. Cell Biol. 112:781–783,.
54 Bradbury N A, Jilling T, Berta G, Sorscher E J, Bridges R J, Kirk K L. (1992) Regulation of plasma membrane recycling by CFTR. Science 256:530–531.
55 Boucher, R. C. (1994). "Human airway ion transport. Part two." *Am J Respir Crit Care Med* 150(2): 581–93.
56 Briel, M., R. Greger, et al. (1998). "Cl-transport by cystic fibrosis transmembrane conductance regulator (CFTR) contributes to the inhibition of epithelial Na+ channels (ENaCs) in Xenopus oocytcs co-expressing CFTR and ENaC." *J Physiol (Lond)* 508(Pt 3): 825–36.
57 Brown, C. R., L. Q. Hong-Brown, et al. (1996). "Chemical chaperones correct the mutant phenotype of the delta F508 cystic fibrosis transmembrane conductance regulator protein." *Cell Stress Chaperones* 1(2): 117–25.
58 Becq, F., B. Verrier, et al. (1996). "cAMP- and Ca2+ independent activation of cystic fibrosis transmembrane conductance regulator channels by phenylimidazothiazole drugs." *J Biol Chem* 271(27): 16171–9.
59 Bennett, W. Δ., K. N. Olivier, et al. (1996). "Effect of uridine 5'-triphosphate plus amiloride on mucociliary clearance in adult cystic fibrosis." *Am J Respir Crit Care Med* 153(6 Pt 1): 1796–801.
60 Boasquevisque, C. H., B. N. Mora, et al. (1998). "Ex vivo liposome-mediated gene transfer to lung isografts." *J Thorac Cardiovase Surg* 115(1): 38–44.
61 Bradbury, N. A., J. A. Cohn, et al. (1994). "Biochemical and biophysical identification of cystic fibrosis transmembrane conductance regulator chloride channels as components of endocytic clathrin-coated vesicles." J Biol Chem 269(11): 8296–302.
62 Brezillon, S., J. M. Zahm, et al. (1997). "ATP depletion induces a loss of respiratory epithelium functional integrity and down-regulates CFTR (cystic fibrosis transmembrane conductance regulator) expression." *J Biol Chem* 272(44): 27830–8.
63 Brown, C. R., L. Q. Hong-Brown, et al. (1996). "Chemical chaperones correct the mutant phenotype of the Δ F508 cystic fibrosis transmembrane conductance regulator protein." *Cell Stress Chaperones* 1(2): 117–25.
64 Byk, G., C. Dubertret, et al. (1998). "Synthesis, activity, and structure—activity relationship studies of novel cationic lipids for DNA transfer." J Med Chem 41(2): 229–35.
65 Cantiello, H. F., G. R. Jackson, Jr., et al. (1998). "Electrodiffusional ATP movement through the cystic fibrosis transmembrane conductance regulator" *Am J Physiol* 274(3 Pt 1): C799–809.
66 Cantiello, H. F. (1996). "Role of the actin cytoskeleton in the regulation of the cystic fibrosis transmembrane conductance regulator." *Exp Physiol* 81(3): 505–14.
67 Carson, M. R., M. C. Winter, et al. (1995). "Pyrophosphate stimulates wild-type and mutant cystic fibrosis transmembrane conductance regulator Cl- channels." *J Biol Chem* 270(35): 20466–72.
68 Carnoy C. Ramphal R. Scharfman A. Lo-Guidice J M. Houdret N. Klein A. Galabert C. Lamblin G. Roussel P.

(1993) Altered carbohydrate composition of salivary mucins from patients with cystic fibrosis and the adhesion of *Pseudomonas aeruginosa*. Amer J of Resp Cell & Mol Biol. 9(3):323–34.

69 Castells, M. T., Ballesta, J., Madrid, J. F., Aviles, M., and Martinez-Menarguez, J. A.,(1991) Characterization of glycoconjugates in developing rat respiratory system by means of conventional and lectin biochemistry. Histochemistry 95: 419–426.

70 Chao, A. C., F. J. de Sauvage, et al. (1994). "Activation of intestinal CFTR Cl- channel by heat-stable enterotoxin and guanylin via cAMP-dependent protein kinase." *Embo J* 13(5): 1065–72.

71 Chao, A. C., K. Kouyama, et al. (1995). "Calcium- and CaMKII-dependent chloride secretion induced by the microsomal Ca(2)-ATPase inhibitor 2,5-di-(tert-butyl)-1, 4-hydroquinone in cystic fibrosis pancreatic epithelial cells." *J Clin Invest* 96(4): 1794–801.

72 Clarke, L. L., B. R. Grubb, et al. (1994). "Relationship of a non-cystic fibrosis transmembrane conductance regulator-mediated chloride conductance to organ-level disease in Cftr(-/-) mice." *Proc Natl Acad Sci USA* 91(2): 479–83.

73 Colledge, W. H., B. S. Abella, et al. (1995). "Generation and characterization of a delta F508 cystic fibrosis mouse model." *Nat Genet* 10(4): 445–52.

74 Conigrave, A. D. and Jiang, L. (1995) Review: $Ca^{2+}$-mobilizing receptors for ATP and UTP. Cell Calcium 17:111–119.

75 Conigrave, A. Δ. and L. Jiang (1995). "Review: Ca(2+)-mobilizing receptors for ATP and UTP." *Cell Calcium* 17(2): 111–9.

76 Cuppens, H., W. Lin, et al. (1998). "Polyvariant mutant cystic fibrosis transmembrane conductance regulator genes. The polymorphic (Tg)m locus explains the partial penetrance of the T5 polymorphism as a disease mutation." *J Clin Invest* 101(2): 487–96.

77 Davies, J. C., M. Stern, et al. (1997). "CFTR gene transfer reduces the binding of *Pseudomonas aeruginosa* to cystic fibrosis respiratory epithelium." *Am J Respir Cell Mol Biol* 16(6): 657–63.

78 Davis, P., C. Silski, et al. (1994). "cAMP does not regulate (Ca2]i in human tracheal epithelial cells in primary culture." *J Cell Sci* 107(10): 2899–907.

79 Delaney, S. J., E. W. Alton, et al. (1996). "Cystic fibrosis mice carrying the missense mutation G551D replicate human genotype-phenotype correlations." *Embo J* 15(5): 955–63.

80 Devidas, S. and W. B. Guggino (1997). "The cystic fibrosis transmembrane conductance regulator and ATP." *Curr Opin Cell Biol* 9(4): 547–52.

81 Devor, D. C., A. K Singh, et al. (1996). "Modulation of Cl- secretion by benzimidazolones. II. Coordinate regulation of apical GCl and basolateral GK." *Am J Physiol* 271(5 Pt 1): L785–95.

82 Devor, D. C., A. K. Singh, et al. (1997). "Psoralens: novel modulators of Cl- secretion." *Am J Physiol* 272(3 Pt 1): C976–88.

83 Dickinson, P., J. R. Dorin, et al. (1995). "Modelling cystic fibrosis in the mouse." *Mol Med Today* 1(3): 140–8.

84 Eastman, S. J., J. D. Tousignant, et al. (1998). "Aerosolization of cationic lipid:pDNA complexes—in vitro optimization of nebulizer parameters for human clinical studies." *Hum Gene Ther* 9(1): 43–52.

85 Egan, M. E., E. M. Schwiebert, et al. (1995). "Differential expression of ORCC and CFTR induced by low temperature in CF airway epithelial cells." *Am J Physiol* 268(1 Pt 1): C243–51.

86 Escriou, V., C. Ciolina, et al. (1998). "Cationic lipid-mcdiated gene transfer: effect of serum on cellular uptake and intracellular fate of lipopolyaminc/DNA complexes." *Biochim Biophys Acta* 1368(2): 276–88.

87 Everson Pearce, A. C. (1985.) Histochemistry theoretical and applied. Vol. 2. Analytical Technology, Churchhill Livingstone, NY N.Y., 88 FitzSimmons, S. C. (1994). "The changing epidemiology of cystic fibrosis." *Curr Probl Pediatr* 24(5): 171–9.

89 Fulmer, S. B., E. M. Schwiebert, et al. (1995). "Two cystic fibrosis transmembrane conductance regulator mutations have different effects on both pulmonary phenotype and regulation of outwardly rectified chloride currents." *Proc Natl Acad Sci USA* 92(15): 6832–6.

90 Gadsby, D. C. and A. C. Nairn (1994). "Regulation of CFTR channel gating." *Trends Biochem Sci* 19(11): 513–8.

91 Gaillard, D., S. Ruocco, et al. (1994). "Immunohistochemical localization of cystic fibrosis transmembrane conductance regulator in human fetal airway and digestive mucosa." *Pediatr Res* 36(2): 137–43.

92 Gaillard, D., S. Ruocco, et al. (1994). "Immunohistochemical localization of cystic fibrosis transmembrane conductance regulator in human fetal airway and digestive mucosa." *Pediatr Res* 36(2): 137–43.

93 Guggino, W. B., Egan, M. & Schwicbert, E.(1995). Mechanisms for the interaction of CFTR with other secretory Cl- channels. *Pedatric Pulmonology* S12, 115

94 Guay-Broder, C., K. A. Jacobson, et al. (1995). "A1 receptor antagonist 8-cyclopentyl-1,3-dipropylxanthine selectively activates chloride efflux from human epithelial and mouse fibroblast cell lines expressing the cystic fibrosis transmembrane regulator Δ F508 mutation." *Biochemistry* 34(28): 9079–87.

95 Heilbronn, E., B. H. Knoblauch, et al. (1997). "Uridine nucleotide receptors and their ligands: structural, physiological, and pathophysiological aspects, with special emphasis on the nervous system." *Neurochem Res* 22(8): 1041–50.

96 Ho, K. (1998). "The ROMK-cystic fibrosis transmembrane conductance regulator connection: new insights into the relationship between ROMK and cystic fibrosis transmembrane conductance regulator channels." *Curr Opin Nephrol Hypertens* 7(1): 49–58.

97 Hwang, T. H., E. M. Schwiebert, et al. (1996). "Apical and basolateral ATP stimulates tracheal epithelial chloride secretion via multiple purinergic receptors." *Am J Physiol* 270(6 Pt 1): C1611–23.

98 Ishikawa, S., M. Higashiyama, et al. (1997). "Extracellular ATP promotes cellular growth of renal inner medullary collecting duct cells mediated via P2u receptors." *Nephron* 76(2): 208–14.

99 Ismailov, II, M. S. Awayda, et al. (1996). "Regulation of epithelial sodium channels by the cystic fibrosis transmembrane conductance regulator." *J Biol Chem* 271(9): 4725–32.

100 Ismailov, II, B. K. Berdiev, et al. (1997). "Role of actin in regulation of epithelial sodium channels by CFTR." *Am J Physiol* 272(4 Pt 1): C1077–86.

101 Jia, Y., C. J. Mathews, et al. (1997). "Phosphorylation by protein kinase C is required for acute activation of cystic fibrosis transmembrane conductance regulator by protein kinase A." *J Biol Chem* 272(8): 4978–84.

102 Jiang, Q. and J. F. Engelhardt (1998): "Cellular heterogeneity of CFTR gene expression and function in the lung: implications for gene therapy for cystic fibrosis." *Eur. J. Hum. Gen.* 6:12–31.

103 Johnson, L. G., R. J. Pickles, et al. (1996). "In vitro assessment of variables affecting the efficiency and efficacy of adenovirus-mediated gene transfer to cystic fibrosis airway epithelia" *Hum Gene Ther* 7(1): 51–9.

104 Kerem, E. and B. Kerem (1995). "The relationship between genotype and phenotype in cystic fibrosis." *Curr Opin Pulm Med* 1(6): 450–6.

105 Knowles, M. R., K. N. Olivier, et al. (1995). "Pharmacologic treatment of abnormal ion transport in the airway epithelium in cystic fibrosis." *Chest* 107(2 Suppl): 71S-76S.

106 Knowles, M. R., A. M. Paradiso, et al. (1995). "In vivo nasal potential difference: techniques and protocols for assessing efficacy of gene transfer in cystic fibrosis." *Hum Gene Ther* 6(4): 445–55.

107 Knowles, M. R., P. G. Noone, et al. (1998). "A double-blind, placebo controlled, dose ranging study to evaluate the safety and biological efficacy of the lipid-DNA complex GR213487B in the nasal epithelium of adult patients with cystic fibrosis [In Process Citation]." *Hum Gene Ther* 9(2): 249–69.

108 Kottra G. (1995). "Calcium is not involved in the cAMP-mediated stimulation of Cl- conductance in the apical membrane of Necturus gallbladder epithelium." *Pflugers Arch* 429(5): 647–58.

109 Kube, D., Perez, A. & Davis, P. B. (1995). Quantitative fluorescent microscopy reveals altered cell surface glycoconjugates on 9HTEo_cells transfected with the regulatory domain of CFTR or F508 CFTR. *Pediatric Pulmonology* S12, 238

110 Lansdell, K. A., S. J. Delaney, et al. (1998). "Comparison of the gating behaviour of human and murine cystic fibrosis transmembrane conductance regulator Cl- channels expressed in mammalian cells." *J Physiol (Lond)* 508(Pt 2): 379–92.

111 Lansdell, K. A., S. J. Delaney, et al. (1998). "Comparison of the gating behaviour of human and murine cystic fibrosis transmembrane conductance regulator Cl- channels expressed in mammalian cells." *J Physiol (Lond)* 508(Pt 2): 379–92.

112 Lambin G., Lhermitte, M., Klein, A., Houdret, N., Scharfman, A., Ramplhal, R., and Roussel, P.(1991) The carbohydrate diversity of human respiratory mucins: a protection for the underlying mucosa? Am. Rev. Respir. Dis. 144: S19-S24

113 Larson, J. E., S. L. Morrow, et al. (1997). "Reversal of cystic fibrosis phenotype in mice by gone therapy in utero [letter] [see comments]." *Lancet* 349(9052): 619–20.

114 Lazarowski, E. R, A. M. Paradiso, et al. (1997). "UDP activates a mucosal-restricted receptor on human nasal epithelial cells that is distinct from the P2Y2 receptor." *Proc Natl Acad Sci USA* 94(6): 2599–603.

115 Leung, A. Y., P. Y. Wong, et al. (1996). "cAMP- but not Ca(2)-regulated Cl- conductance is lacking in cystic fibrosis mice epididymides and seminal vesicles." *Am J Physiol* 271(1 Pt 1): C188–93.

116 Linsdell, P. and J. W. Hanrahan (1998). "Adenosine Triphosphate-dependent Asymmetry of Anion Permeation in the Cystic Fibrosis Transmembrane Conductance Regulator Chloride Channel." *J Gen Physiol* 111(4): 601–14.

117 Lohmann, S. M., A. B. Vaandrager, et al. (1997). "Distinct and specific functions of cGMP-dependent protein kinass." *Trends Biochem Sci* 22(8): 307–12.

118 Ma, J., J. E. Tasch, et al. (1996). "Phosphorylation-dependent block of cystic fibrosis transmembrane conductance regulator chloride channel by exogenous R domain protein." *J Biol Chem* 271(13): 7351–6.

119 MacVinish, L. J., D. R Gill, et al. (1997). "Chloride secretion in the trachea of null cystic fibrosis mice: the effects of transfection with pTrial10-CFTR2." *J Physiol (Lond)* 499(Pt 3): 677–87.

120 Marcel, T. and J. D. Grausz (1997). "The TMC Worldwide Gene Therapy Enrollment Report, end 1996." *Hum Gene Ther* 8(6): 775–800.

121 Mazzuca, M., Lhermitte, M., Lafitte, J-J., and Roussel, P. (1982) Use of lectins for detection of glyconjugates in the glandular cells of the human bronchial mucosa J. Histochem and Cytochem 30:956–966.

122 McCray P B, Reenstra W W, Louie E, Johnson J, Bettencourt J D, Bastacky J. (1992) Expression of CFTR and presence of cAMP-mediated fluid secretion in human fetal lung. Am. J. Physiol 262:L472-L481.

123 McCray, P. B., Jr., W. W. Reenstra, et al. (1992). "Expression of CFTR and presence of cAMP-mediated fluid secretion in human fetal lung." *Am J Physiol* 262(4 Pt 1): L472–81.

124 McCray, P. B., Jr., C. L. Wohlford-Lenane, et al. (1992). "Localization of cystic fibrosis transmembrane conductance regulator mRNA in human fetal lung tissue by in situ hybridization." *J Clin Invest* 90(2): 619–25.

125 McGrath, S A, Basu A, Zeitlin P L.(1989) Cystic fibrosis gene and protein expression duering fetal lung development. Am. J. Respir. Cell Mol. Biol. 8: 201–208, 1993. *Science* 245, 1066–1073.

126 McGrath, S. A., A. Basu, et al. (1993). "Cystic fibrosis gene and protein expression during fetal lung development" *Am J Respir Cell Mol Biol* 8(2): 201–8.

127 McDonald, R. A., R. P. Matthews, et al. (1995). "Basal expression of the cystic fibrosis transmembrane conductance regulator gene is dependent on protein kinase A activity." *Proc Natl Acad Sci USA* 92(16): 75604.

128 Mercola, M. and Stiles C. D. (1988)Growth factor superfamilics and mammalian embryogenesis. Development 102: 451–460.

129 Monavalin, P., Dearborn, D. G., McPherson, J. M., Smith, A. E. (1995) Sequence homologies between nucleotide binding regions of CFTR and G-proteins suggest structural and functional similarities. *FEBS Letters* 366, 87–91

130 Merten, M. D., A. Saleh, et al. (1998). "Characterization of two distinct P2Y receptors in human tracheal gland cells." *Eur J Biochem* 251(1–2): 19–24.

131 Mickle, J. E., M. Macek Jr, et al. (1998). "A mutation in the cystic fibrosis transmembrane conductance regulator gene associated with elevated sweat chloride concentrations in the absence of cystic fibrosis." *Hum Mol Genet* 7(4): 715–27.

132 Mills, C. L., J. R. Dorin, et al. (1995). "Decreased beta-adrenergic stimulation of glycoprotein secretion in CF mice submandibular glands: reversal by the methylxanthine, IBMX." *Biochem Biophys Res Commun* 215(2): 674–81.

133 Mittereder, N., S. Yei, et al. (1994). "Evaluation of the efficacy and safety of in vitro, adenovirus-mediated transfer of the human cystic fibrosis transmembrane conductance regulator cDNA." *Hum Gene Ther* 5(6): 717–29.

134 Murphy, J. E., T. Uno, et al. (1998). "A combinatorial approach to the discovery of efficient cationic peptoid reagents for gene delivery." *Proc Natl Acad Sci USA* 95(4): 1517–22.

135 North, R. A. and E. A. Barnard (1997). "Nucleotide receptors." *Curr Opin Neurobiol* 7(3): 346–57.

136 Ostedgaard, L. S., D. P. Rich, et al. (1997). "Association of domains within the cystic fibrosis transmembrane conductance regulator." *Biochemistry* 36(6): 1287–94.

137 Parr, C. E., D. M. Sullivan, et al. (1994). "Cloning and expression of a human P2U nucleotide receptor, a target for cystic fibrosis pharmacotherapy [published erratum appears in Proc Natl Acad Sci USA Dec. 20, 1994;91(26): 13067]." *Proc Natl Acad Sci USA* 91(8): 3275–9.

138 Pasyk, E. A. and J. K. Foskett (1995). "Mutant (Δ F508) cystic fibrosis transmembrane conductance regulator Cl-channel is functional when retained in endoplasmic reticulum of mammalian cells." *J Biol Chem* 270(21): 12347–50.

139 Pier, G. B., M. Grout, et al. (1996). "How mutant CFTR may contribute to *Pseudomonas aeruginosa* infection in cystic fibrosis." *Am J Respir Crit Care Med* 154(4 Pt2): S175–82.

140 Plotkowski, M. C., O. Bajolet-Laudinat, et al. (1993). "Cellular and molecular mechanisms of bacterial adhesion to respiratory mucosa." *Eur Respir J* 6(6): 903–16.

141 Porteous, D. J., J. R. Dorin, et al. (1997). "Evidence for safety and efficacy of DOTAP cationic liposome mediated CFTR gene transfer to the nasal epithelium of patients with cystic fibrosis." *Gene Ther* 4(3): 210–8.

142 Ramjeesingh, M., L. J. Huan, et al. (1998). "Assessment of the efficacy of in vivo CFTR protein replacement therapy in CF mice [In Process Citation]." *Hum Gene Ther* 9(4): 521-S.

143 Ramphal, R., Houdret, N., Koo, L., Lambin, G., and Roussel, P (1989). Differences in adhesion of *Pseudomonas aeruginosa* to mucin glycopeptides from sputa of patients with cystic fibrosis and chronic bronchitis. Infect and Immun 57: 3066–3071.

144 Ripoll, P. J., A. Cowper, et al. (1998). "A new yeast artificial chromosome vector designed for gene transfer into mammalian cells." *Gene* 210(1): 163–72.

145 Riordan, J. R., Rommens, J. M., Kerem B., Alon, N., Rozmahel, R., Grzelczak, Z., Zielenski, J., Lok, S., Plavsic, N., Chou, J., Drumm, M. L., Iannuzzi, M. C., Collins, F. S. & Tsui, L. C. (1989) Identification of the cystic fibrosis gene: cloning and characterization of complementary DNA. Science 245:1059–1065.

146 Robbins, P. D., H. Tahara, et al. (1998). "Viral vectors for gene therapy." *Trends Biotechnol* 16(1): 35–40.

147 Rongen, G. A., J. S. Floras, et al. (1997). "Cardiovascular pharmacology of purines [editorial]." *Clin Sci (Colch)* 92(1): 13–24.

148 Rosenstein, B. J. and P. L. Zeitlin (1998). "Cystic fibrosis." *Lancet* 351(9098): 277–82.

149 Rubenstein, R. C., M. E. Egan, et al. (1997). "In vitro pharmacologic restoration of CFTR-mediated chloride transport with sodium 4-phenylbutyrate in cystic fibrosis epithelial cells containing Δ F508-CFTR." *J Clin Invest* 100(10): 2457–65.

150 Rubenstein, R. C. and P. L. Zeitlin (1998). "A pilot clinical trial of oral sodium 4-phenylbutyrate (Buphenyl) in ΔF508-homozygous cystic fibrosis patients: partial restoration of nasal epithelial CFTR function." *Am J Respir Crit Care Med* 157(2): 484–90.

151 Sato, S., C. L. Ward, et al. (1996). "Glycerol reverses the misfolding phenotype of the most common cystic fibrosis mutation." *J Biol Chem* 271(2): 635–8.

152 Schiedner, G., N. Morral, et al. (1998). "Genomic DNA transfer with a high-capacity adenovirus vector results in improved in vivo gene expression and decreased toxicity." *Nat Genet* 18(2): 180–3.

153 Schwiebert, E. M., L. P. Cid-Soto, et al. (1998). "Analysis of ClC-2 channels as an alternative pathway for chloride conduction in cystic fibrosis airway cells." *Proc Natl Acad Sci USA* 95(7): 3879–84.

154 Schwicbert, E. M., M. M. Morales, et al. (1998). "Chloride channel and chloride conductance regulator domains of CFTR, the cystic fibrosis transmembrane conductance regulator [In Process Citation]." *Proc Natl Acad Sci USA* 95(5): 2674–9.

155 Scars, C. L., F. Firoozmand, et al. (1995). "Genistein and tyrphostin 47 stimulate CFTR-mediated Cl- secretion in T84 cell monolayers." *Am J Physiol* 269(6 Pt 1): G874-82.

156 Sekhon, H. S. and J. E. Larson (1995). "In utero gene transfer into the pulmonary epithelium." *Nat Med* 1(11): 1201–3.

157 Shalom, S., A. Strinkovski, et al. (1997). "An optical submicrometer calcium sensor with conductance sensing capability." *Anal Biochem* 244(2): 256–9.

158 Snouwaert, J. N., K K. Brigman, et al. (1992). "An animal model for cystic fibrosis made by gene targeting." *Science* 257: 1083–8.

159 Stern, R. C. (1997). "The diagnosis of cystic fibrosis." *N Engl J Med* 336(7): 487–91.

160 Stutts, M. J., B. C. Rossier, et al. (1997). "Cystic fibrosis transmembrane conductance regulator inverts protein kinase A-mediated regulation of epithelial sodium channel single channel kinetics." *J Biol Chem* 272(22): 14037–40.

161 Sugita, M., Y. Yue, et al. (1998). "CFTR Cl- channel and CFTR-associated ATP channel: distinct pores regulated by common gates [In Process Citation]." *Embo J* 17(4): 898–908.

162 Teem, J. L., M. R. Carson, et al. (1996). "Mutation of R555 in CFTR-delta F508 enhances function and partially corrects defective processing." *Receptors Channels* 4(1): 63–72.

163 Ten Have-Opbroek A. A. W. (1981) The development of the lung in mammals: An analysis of concepts and findings. Am. J. Anat. 162: 201–219.

164 Teng, H., M. Jorissen, et al. (1997). "Increased proportion of exon 9 alternatively spliced CFTR transcripts in vas deferens compared with nasal epithelial cells." *Hum Mol Genet* 6(1): 85–90.

165 Thorn, P. (1996). "Spatial domains of Ca2+ signaling in secretory epithelial cells." *Cell Calcium* 20(2): 203–14.

166 Tizzano, E. F., H. O'Brodovich, et al. (1994). "Regional expression of CFTR in developing human respiratory tissues." *Am J Respir Cell Mol Biol* 10(4): 355–62.

167 Tizzano, E F., O'Brodovich, H., Chitayat D., Benichou, J-C, Buchwald M. (1994) Regional expression of CFTR in developing human respiratory tissues. Am. J. Respir. Cell Mol. Biol. 10: 355–362.

168 Thorn, P. (1996) Spatial domians for $Ca^{2+}$ signaling in secretory epithelial cells. Cell Calcium 20: 203–214.

169 Tummler, B., J. Bosshammer, et al. (1997). "Infections with *Pseudomonas aeruginosa* in patients with cystic fibrosis." *Behring Inst Mitt*(98): 249–55.

170 Welch, W. J. and C. R. Brown (1996). "Influence of molecular and chemical chaperones on protein folding [published erratum appears in Cell Stress Chaperones September 1996;1(3):207]." *Cell Stress Chaperones* 1(2): 109–15.

171 Wersto, R. P., E. R. Rosenthal, et al. (1996). "Uptake of fluorescent dyes associated with the functional expression of the cystic fibrosis transmembrane conductance regulator in epithelial cells." *Proc Natl Acad Sci USA* 93(3): 1167–72.

172 Weyer, P., Barasch, J., Al Awqati, Q., Ausiello, D. A. & Brown, D. (1995) Immunolocaliztion of two sialytransferases is altered in polarized LLC-PK1 epithelal cells expressing F508 CFTR. *Pediatric Pulmonology* S12,238.

173 Wigglesworth, J. S., Hislop, A. A., Desai, R., (1991) Biochemical and morphometric analyses in hypoplastic lung. Pediatric Pathology 11: 537–549.

174 Williams, M. (1996). "Challenges in developing P2 purinoceptor-based therapeutics." *Ciba Found Symp* 198: 309–21.

175 Wilmott, R. W., R. S. Amin, et al. (1996). "Safety of adenovirus-mediated transfer of the human cystic fibrosis transmembrane conductance regulator cDNA to the lungs of nonhuman primates." *Hum Gene Ther* 7(3): 301–18.

176 Wine, J. J., D. Glavac, et al. (1998). "Genomic DNA sequence of Rhesus (M. mulatta) cystic fibrosis (CFTR) gene [In Process Citation]." *Mamm Genome* 9(4): 301–5.

177 Yei, S., N. Mittereder, et al. (1994). "Adenovirus-mediated gene transfer for cystic fibrosis: quantitative evaluation of repeated in vivo vector administration to the lung." *Gene Ther* 1(3): 192–200.

178 Yei, S., N. Mittereder, et al. (1994). "In vivo evaluation of the safety of adenovirus-mediated transfer of the human cystic fibrosis transmembrane conductance regulator cDNA to the lung." *Hum Gene Ther* 5(6): 731–44.

179 Zhang, F., N. Kartner, et al. (1998). "Limited proteolysis as a probe for arrested conformational maturation of delta F508 CFTR [letter] [In Process Citation]." *Nat Struct Biol* 5(3): 180–3.

180 Zhou, L., C. R. Dey, et al. (1994). "Correction of lethal intestinal defect in a mouse model of cystic fibrosis by human CFTR." *Science* 266(5191): 1705–8.

181 Zhou, S. S., A. Takai, et al. (1997). "Phosphatase-mediated enhancement of cardiac cAMP-activated Cl- conductance by a Cl- channel blocker, anthracene-9-carboxylate." *Circ Res* 81(2): 219–28.

Equivalents

It will be appreciated that the methods and compositions of the present invention are capable of being incorporated in the form of a variety of embodiments, only a few of which have been illustrated and described above. While specific examples have been provided, the above description is illustrative and not restrictive. The invention may be embodies in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within the scope of the invention.

All publications and patent documents cited in this application are incorporated by reference in their entirety for all purposes to the same extent as if each individual publication or patent document were so individually denoted.

What we claim is:

1. A method of treating CFTR functional deficiency, comprising the steps of: providing a mammalian fetus having the deficiency, and injecting into amniotic fluid surrounding the fetus an adenoviral vector comprising a gene encoding a functional CFTR protein in operable linkage with a promoter, wherein the fetus is either a non-human fetus at a stage of gestation comparable to that of a 10–20 week human fetus or is a human fetus at 10–20 week gestation, and wherein the CFTR gene is expressed at a level sufficient for amelioration of the deficiency such that the fetus survives through development into adulthood.

2. The method of claim 1 wherein the vector is Av1CF2.

3. A cell population isolated from a population of cells in a developing respiratory epithelium of a mammalian fetus,
   wherein the fetus is deficient in CFTR function; wherein the cells are transfected with an adenoviral vector comprising a gene encoding a functional CFTR protein in operable linkage with a promoter; and
   wherein the mammalian fetus is comparable to that of a 10–20 week human fetus or is a human fetus at 10–20 week gestation; and
   wherein the CFTR gene is expressed at a level sufficient for amelioration of the deficiency such that the fetus survives through development into adulthood.

4. The cell population of claim 3 wherein the vector is Av1CF2.

5. A kit for in utero treatment of a CFTR-deficient mammalian fetus comprising:
   a container holding an amount of an adenoviral vector comprising a gene encoding a functional CFTR protein in operable linkage with a promoter, and
   wherein the CFTR gene is expressed at a level sufficient for amelioration of the deficiency such that a fetus so treated survives into adulthood; and
   instructions for administering the vector to a mammalian fetus having the deficiency; and wherein the fetus is a non-human mammalian fetus at a stage of gestation comparable to that of a 10–20 week human fetus or is a human fetus at 10–20 week gestation; and
   wherein the instructions direct that the vector be injected into amniotic fluid surrounding the fetus;
   such that the treated fetus will survive into adulthood.

6. The kit of claim 5 wherein the vector is Av1CF2.

* * * * *